US008609710B2

(12) United States Patent
Nagata et al.

(10) Patent No.: US 8,609,710 B2
(45) Date of Patent: Dec. 17, 2013

(54) CYCLOALKYL-SUBSTITUTED IMIDAZOLE DERIVATIVE

(75) Inventors: Tsutomu Nagata, Ichikawa (JP);
Masahiro Inoue, Shinagawa (JP); Yuka Ashida, Itabashi (JP); Kengo Noguchi, Shinagawa (JP); Makoto Ono, Toshima (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/550,366

(22) Filed: Jul. 16, 2012

(65) Prior Publication Data

US 2013/0022587 A1 Jan. 24, 2013
US 2013/0230501 A9 Sep. 5, 2013

Related U.S. Application Data

(63) Continuation of application No. PCT/JP2011/055953, filed on Mar. 14, 2011.

(30) Foreign Application Priority Data

Mar. 18, 2010 (JP) ................................. 2010-062155

(51) Int. Cl.
*A01N 43/50* (2006.01)
*A61K 31/4164* (2006.01)

(52) U.S. Cl.
USPC ............ 514/399; 514/385; 514/396; 514/397

(58) Field of Classification Search
USPC .................. 514/385, 396, 397, 399
See application file for complete search history.

(56) References Cited

U.S. PATENT DOCUMENTS

| | | | | |
|---|---|---|---|---|
| 6,713,496 | B2 * | 3/2004 | Allerton et al. | 514/341 |
| 6,897,208 | B2 * | 5/2005 | Edwards et al. | 514/183 |
| 6,949,577 | B2 * | 9/2005 | Allerton et al. | 514/396 |
| 6,958,402 | B2 * | 10/2005 | Allerton et al. | 548/340.1 |
| 8,288,425 | B2 * | 10/2012 | Edwards et al. | 514/397 |
| 2003/0199522 | A1 | 10/2003 | Allerton et al. | |
| 2007/0129341 | A1 | 6/2007 | Kallus et al. | |
| 2008/0262028 | A1 | 10/2008 | Kallus et al. | |
| 2011/0213143 | A1 * | 9/2011 | Amada et al. | 540/579 |

FOREIGN PATENT DOCUMENTS

| | | |
|---|---|---|
| JP | 2004-506044 | 2/2004 |
| JP | 2005-516972 | 6/2005 |
| JP | 2005-520811 | 7/2005 |
| WO | WO 02/14285 | 2/2002 |
| WO | WO 03/013526 | 2/2003 |
| WO | WO 03/061652 | 7/2003 |
| WO | WO 03/061653 | 7/2003 |
| WO | WO 2005/105781 | 11/2005 |
| WO | WO 2007/045339 A1 | 4/2007 |

OTHER PUBLICATIONS

Nantermet et al., "Imidazole acetic acid TAFIa inhibitors; SAR studies centered around the basic P1 group"; 2004; Bioorganic & Medicinal Chemistry Letters; 14 (9); p. 2141-2145.*
Bunnage et al. "Discovery of Potent & Selective Inhibitors of Activated Thrombin-Activatable Fibrinolysis Inhibitor for the Treatment of Thrombosis"; 2007; J. Med. Chem.; 50(24); pp. 6095-6103.*
Nagata, T., et al., U.S. Appl. No. 13/634,678, filed Sep. 13, 2012, entitled "Cyclopropanecarboxylic Acid Derivative," 322 pages.
English translation of International Preliminary Report on Patentability, Application No. PCT/JP2011/055953, Filed Mar. 14, 2011, Issued Oct. 23, 2012, 9 pages.
English translation of International Search Report, Application No. PCT/JP2011/055954, Filed Mar. 14, 2011, Mailed May 10, 2011, 3 pages.
English translation of International Preliminary Report on Patentability, Application No. PCT/JP2011/055954, Filed Mar. 14, 2011, Issued Oct. 23, 2012, 7 pages.
Bunnage, Mark E., et al., "Discovery of Potent & Selective Inhibitors of Activated Thrombin-Activatable Fibrinolysis Inhibitor for the Treatment of Thrombosis," *Journal of Medicinal Chemistry*, vol. 50, pp. 6095-6103 (2007).
Muto, Yuko, et al., "EF6265, a novel inibitor of activated thrombin-activatable fibrinolysis inhibitor, protects against sepsis-induced organ dysfunction in rats," *Critical Care Medicine*, vol. 37, No. 5, pp. 1744-1749 (2009).
Suzuki, Kokichi, et al., "Enhancement of Fibrinolysis by EF6265 [(S)-7-Amino-2-[[[(R)-2-methyl-1-(3-phenylpropanoylamino)propyl]hydroxyphosphinoyl]methyl]heptanoic Acid], a Specific Inhibitor of Plasma Carboxypeptidase B," *Journal of Pharmacology and Experimental Therapeutics*, vol. 309, No. 2, pp. 607-615 (2004).
Wang, X., et al., "Murine model of ferric chloride-induced vena cava thrombosis: evidence for effect of potato carboxypeptidase inhibitor," *Journal of Thrombosis and Haemostasis*, vol. 4, pp. 403-410 (2006).
Willemse, J. L., et al., "Carboxypeptidase U (TAFIa): a new drug target for fibrinolytic therapy?," *Journal of Thrombosis and Haemostasis*, vol. 7, pp. 1962-1971 (2009).
International Search Report, Application No. PCT/JP2011/065953, Filed Mar. 14, 2011, Mailed May 10, 2011, 5 pages.

* cited by examiner

*Primary Examiner* — My-Chau T Tran
(74) *Attorney, Agent, or Firm* — Dorsey and Whitney LLP

(57) ABSTRACT

A compound represented by the following general formula (I) or a pharmacologically acceptable salt thereof, wherein A represents a C3 to C12 cycloalkyl group which may be substituted by one to three selected from a fluoro group, a hydroxy group, a C1 to C6 alkyl group, etc; $R^1$, $R^2$, and $R^3$ each independently represent a hydrogen atom, a fluoro group, or a C1 to C6 alkyl group; $R^4$ represents a hydrogen atom or a prodrug group; and Y represents —$CH_2$—$CHR^5$—$CH_2$—$NHR^6$ (wherein $R^5$ represents a hydrogen atom, a C1 to C6 alkyl group, or a C1 to C6 alkoxy group, and $R^6$ represents a hydrogen atom or a prodrug group), or the like exhibits excellent TAFIa inhibitory activity and is useful as a therapeutic drug for myocardial infarction, angina pectoris, acute coronary syndrome, cerebral infarction, deep vein thrombosis, pulmonary embolism, and the like.

21 Claims, 4 Drawing Sheets

CYCLOALKYL-SUBSTITUTED IMIDAZOLE DERIVATIVE

This application claims the benefit under 35 U.S.C. §111(a) as a continuation application of International Application No. PCT/JP2011/055953, filed Mar. 14, 2011, entitled "Cycloalkyl-Substituted Imidazole Derivative," which claims priority to Japanese Patent Application No. 2010-062155, filed Mar. 18, 2010, the contents of all of which are hereby incorporated in their entirety by reference.

TECHNICAL FIELD

The present invention relates to a novel cycloalkyl-substituted imidazole derivative having excellent TAFIa inhibitory activity.

BACKGROUND ART

When disorders in blood vessels occur in vivo, platelets and/or coagulation cascades are activated for preventing blood leakage to form thrombi, which in turn suppress hemorrhage. Thrombin formed by the coagulation cascade activation cleaves fibrinogen to form insoluble fibrin. Fibrin is present in the form of a network in thrombi and works to strengthen the thrombi. This reaction is called coagulation. The formed fibrin is then degraded through in-vivo reaction. This reaction is fibrinolysis. Under normal conditions, coagulation and fibrinolysis are balanced, and abnormal amounts of thrombi do not accumulate in blood vessels. However, once the balance is disrupted to accelerate coagulation, it may come into a state that a thrombus is likely to be formed in blood vessels, leading to various diseases attributed to thrombosis. The thrombus formation is caused by three factors (Virchow's triad: change in the properties of vascular walls, change in blood components, and change in blood flow). Diseases attributed to the thrombus formation are one of the most general causes of death among advanced nations.

TAFI (thrombin-activatable fibrinolysis inhibitor) is a carboxypeptidase that is produced in the liver and secreted into blood. This enzyme is activated through the cleavage of N-terminal 92 amino acid residues by thrombin or thrombin/thrombomodulin complexes. TAFI is also called procarboxypeptidase U, procarboxypeptidase R, or plasma procarboxypeptidase B.

The activated TAFI is called TAFIa. TAFIa inhibits fibrinolysis by removing the C-terminal Lys or Arg residue of fibrin or fibrin degradation products (FDPs), which are main components of thrombi. Two enzymes, tPA (tissue-type plasminogen activator) and plasminogen, which induce and promote fibrinolysis, bind to the Lys residue of fibrin or FDPs via their Lys-binding sites. On the surface of the fibrin molecule, tPA subsequently activates plasminogen and converts it into plasmin to initiate fibrinolysis. Plasmin cleaves fibrin, and a Lys or Arg residue appears at the C-termini of the formed FDPs. The continuation of fibrinolysis allows plasminogen and tPA to newly bind to the Lys residues of the FDPs to further form plasmin. This efficiently promotes fibrinolysis (positive feedback mechanism of fibrinolysis). TAFIa inhibits the plasminogen activation of tPA on the fibrin molecule by removing the C-terminal Lys residues of FDPs. As a result, efficient fibrinolysis does not occur. TAFIa suppresses the positive feedback mechanism of fibrinolysis. These findings are described in detail in a review on TAFI and its inhibitors (Non Patent Literature 1).

As described above, the fine balance between coagulation and fibrinolysis is achieved in vivo. When coagulation is accelerated by diseases or the like, thrombi come to be likely to be formed, developing various diseases. Such diseases include myocardial infarction, angina pectoris, acute coronary syndrome, cerebral infarction, deep vein thrombosis, pulmonary embolism, peripheral arterial occlusion, sepsis, disseminated intravascular coagulation syndrome, and pulmonary fibrosis.

The previous treatment of thrombosis has often targeted enzymes in the coagulation cascades. These enzymes include activated coagulation factor X (Xa), thrombin, and the like. Inhibitors against these enzymes have the risk of potential adverse reaction such as hemorrhage. Heparin or low-molecular-weight heparin cannot be expected to exert drug efficacy in oral administration and requires administration in hospitals. Warfarin is orally administrable but requires periodic blood tests by reason of interaction with other drugs, etc. Aspirin is an orally administrable drug that inhibits thrombus formation by suppressing the activation of platelets, but has adverse reaction such as gastrorrhagia. A goal for further improving the current therapies is to prevent bleeding time from being prolonged while maintaining high therapeutic effect by drug administration. TAFIa inhibitors are thought to have a small risk of hemorrhage, because they do not influence the process of hemostasis involving coagulation and platelets.

In pathologies where it may arise that a thrombus is likely to be formed due to accelerated coagulation reactions, thrombi can be removed more quickly by making fibrinolysis efficient through the inhibition of TAFIa. This can be expected to exert excellent effects on the treatment/prevention of diseases attributed to thrombi. Some cases of animal experiments that showed an antithrombotic effect by inhibiting TAFIa have been reported so far.

There is a report that the intravenous administration of a TAFIa-inhibiting polypeptide consisting of 39 amino acids (potato carboxypeptidase inhibitor (PCI)) to mice showed an antithrombotic effect in iron chloride-induced thrombus models (Non Patent Literature 2).

A low-molecular-weight TAFIa inhibitor reduced the amount of thrombi by approximately 35% in intravenous administration to rabbit models of venous thrombosis (Non Patent Literature 3)

A low-molecular-weight TAFIa-inhibiting compound showed, in rat models of thromboembolism, a reduction in the amount of thrombus deposits in the kidney with the effect of increasing a fibrinolysis marker D-dimer as well as comparable antithrombotic effect at a reduced dose of tPA in combined use with tPA (Non Patent Literatures 4 and 5).

Patent Literatures 1 to 5 disclose compounds that exhibit TAFIa inhibitory activity.

CITATION LIST

Patent Literature

Patent Literature 1: Pamphlet of International Publication No. WO 2002/014285
Patent Literature 2: Pamphlet of International Publication No. WO 2003/061652
Patent Literature 3: Pamphlet of International Publication No. WO 2003/061653
Patent Literature 4: Pamphlet of International Publication No. WO 2005/105781
Patent Literature 5: Pamphlet of International Publication No. WO 2003/013526

Non Patent Literature

Non Patent Literature 1: Willemse J L, Journal of Thrombosis and Haemostasis, 2009, 7, 1962-71
Non Patent Literature 2: Wang X. et al., Journal of Thrombosis and Haemostasis, 2006, 3, 403-410
Non Patent Literature 3: Bunnage M E., et al., Journal of Medicinal Chemistry, 2007, 50, 6095-6103
Non Patent Literature 4: Muto, Y., et al., Critical Care Med., 2009, 37, 1744-1749
Non Patent Literature 5: Suzuki, K., The Journal of Pharmacology and Experimental Therapeutics, 2004, 309, 607-615

SUMMARY OF INVENTION

Technical Problem

Currently known compounds having TAFIa inhibitory activity are less than satisfactory in terms of efficacy or safety such as the risk of hemorrhage, and there is a great demand for a TAFIa inhibitor excellent in safety and efficacy.

Solution to Problem

The present inventors have conducted various syntheses and studies with the aim of obtaining a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis having excellent TAFIa inhibitory activity. As a result, the present inventors have completed the present invention by finding that a cycloalkyl-substituted imidazole derivative having a particular structure or a pharmacologically acceptable salt thereof exhibits excellent TAFIa inhibitory activity.

The present invention provides a cycloalkyl-substituted imidazole derivative or a pharmacologically acceptable salt thereof, which exhibits excellent TAFIa inhibitory activity, and a pharmaceutical drug containing the same.

Specifically, the present invention provides:

(1) a compound represented by the general formula (I) or a pharmacologically acceptable salt thereof:

[Formula 1]

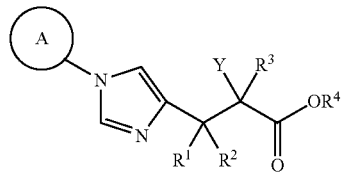

(I)

wherein A represents a C3 to C12 cycloalkyl group which may be substituted by one to three identical or different groups selected from a fluoro group, a hydroxy group, a C1 to C6 alkyl group, a C1 to C6 alkoxy group, an aryloxy group, and a heterocyclyloxy group; $R^1$, $R^2$, and $R^3$ each independently represent a hydrogen atom, a fluoro group, or a C1 to C6 alkyl group; $R^4$ represents a hydrogen atom or a prodrug group; and Y represents a group: —$CH_2$—$CHR^5$—$CH_2$—$NHR^6$ (wherein $R^5$ represents a hydrogen atom, a C1 to C6 alkyl group, or a C1 to C6 alkoxy group, and $R^6$ represents a hydrogen atom or a prodrug group), —O—$CHR^7$—$CH_2$—$NHR^8$ (wherein $R^7$ represents a hydrogen atom, a C1 to C6 alkyl group, or a C1 to C6 alkoxy group, and $R^8$ represents a hydrogen atom or a prodrug group), or

[Formula 2]

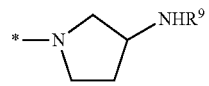

(wherein $R^9$ represents a hydrogen atom or a prodrug group, and * represents the position for substitution);

(2) the compound according to (1) or a pharmacologically acceptable salt thereof, wherein A is a cyclobutyl group, a cyclohexyl group, a cycloheptyl group, a bicyclo[3.1.0]hexyl group, a bicyclo[2.2.1]heptyl group, or an adamantyl group, each of which may be substituted by one to three identical or different groups selected from a fluoro group, a hydroxy group, a C1 to C6 alkyl group, a C1 to C6 alkoxy group, an aryloxy group, and a heterocyclyloxy group;

(3) the compound according to (1) or a pharmacologically acceptable salt thereof, wherein A is a cyclobutyl group, a cyclohexyl group, a cycloheptyl group, a bicyclo[3.1.0]hexyl group, a bicyclo[2.2.1]heptyl group, or an adamantyl group, each of which may be substituted by one to three identical or different groups selected from a hydroxy group, a methyl group, and an ethyl group;

(4) the compound according to (1) or a pharmacologically acceptable salt thereof, wherein A is a cyclohexyl group which may be substituted by one to three identical or different groups selected from a fluoro group, a hydroxy group, a C1 to C6 alkyl group, a C1 to C6 alkoxy group, an aryloxy group, and a heterocyclyloxy group;

(5) the compound according to (1) or a pharmacologically acceptable salt thereof, wherein A is a C3 to C12 cycloalkyl group substituted by one or two identical or different C1 to C6 alkyl groups;

(6) the compound according to (1) or a pharmacologically acceptable salt thereof, wherein A is a C3 to C12 cycloalkyl group substituted by a methyl group or an ethyl group;

(7) the compound according to (1) or a pharmacologically acceptable salt thereof, wherein A is a cyclohexyl group substituted by one or two identical or different C1 to C6 alkyl groups;

(8) the compound according to (1) or a pharmacologically acceptable salt thereof, wherein A is a cyclohexyl group substituted by a methyl group or an ethyl group;

(9) the compound according to (1) or a pharmacologically acceptable salt thereof, wherein A is a group:

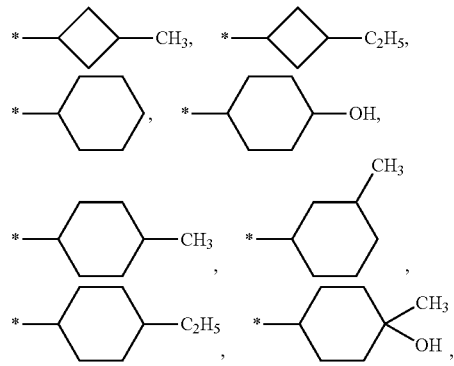

-continued

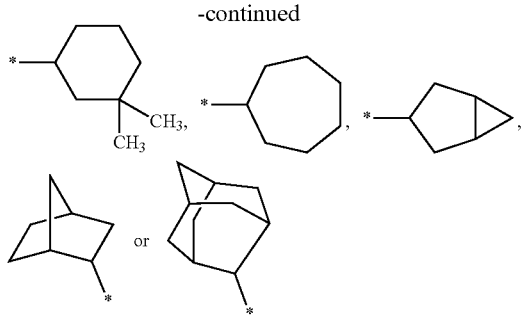

(wherein * represents the position for substitution);

(10) the compound according to (1) or a pharmacologically acceptable salt thereof, wherein A is a group:

[Formula 4]

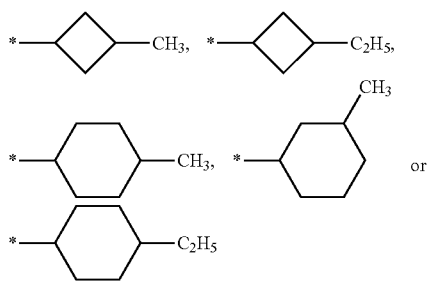

(wherein * represents the position for substitution);

(11) the compound according to (1) or a pharmacologically acceptable salt thereof, wherein A is the group:

[Formula 5]

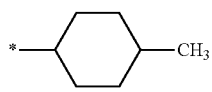

(wherein * represents the position for substitution);

(12) the compound according to (1) or a pharmacologically acceptable salt thereof, wherein A is the group:

[Formula 6]

(wherein * represents the position for substitution);

(13) the compound according to any one of (1) to (12) or a pharmacologically acceptable salt thereof, wherein Y is the group: —$CH_2$—$CHR^5$—$CH_2$—$NHR^6$ (wherein $R^5$ represents a hydrogen atom, a C1 to C6 alkyl group, or a C1 to C6 alkoxy group, and $R^6$ represents a hydrogen atom or a prodrug group);

(14) the compound according to (13) or a pharmacologically acceptable salt thereof, wherein $R^5$ is a hydrogen atom;

(15) the compound according to (13) or (14) or a pharmacologically acceptable salt thereof, wherein $R^6$ is a hydrogen atom;

(16) the compound according to (13) or (14) or a pharmacologically acceptable salt thereof, wherein $R^6$ is a prodrug group;

(17) the compound according to (16) or a pharmacologically acceptable salt thereof, wherein the prodrug group represented by $R^6$ is a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group;

(18) the compound according to (16) or a pharmacologically acceptable salt thereof, wherein the prodrug group represented by $R^6$ is a phenylalanyl group, an L-norleucyl group, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, ({1-[(cyclohexylcarbonyl)oxy]ethoxy}carbonyl) group, or a (1-acetoxyethoxy)carbonyl group;

(19) the compound according to any one of (1) to (12) or a pharmacologically acceptable salt thereof, wherein Y is the group: —O—$CHR^7$—$CH_2$—$NHR^8$ (wherein $R^7$ represents a hydrogen atom, a C1 to C6 alkyl group, or a C1 to C6 alkoxy group, and $R^8$ represents a hydrogen atom or a prodrug group);

(20) the compound according to (19) or a pharmacologically acceptable salt thereof, wherein $R^7$ is a hydrogen atom;

(21) the compound according to (19) or (20) or a pharmacologically acceptable salt thereof, wherein $R^8$ is a hydrogen atom;

(22) the compound according to (19) or (20) or a pharmacologically acceptable salt thereof, wherein $R^8$ is a prodrug group;

(23) the compound according to (22) or a pharmacologically acceptable salt thereof, wherein the prodrug group represented by $R^8$ is a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group;

(24) the compound according to any one of (1) to (12) or a pharmacologically acceptable salt thereof, wherein Y is the group:

[Formula 7]

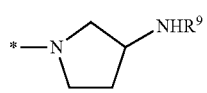

(wherein $R^9$ represents a hydrogen atom or a prodrug group, and * represents the position for substitution);

(25) the compound according to any one of (1) to (12) or a pharmacologically acceptable salt thereof, wherein Y is the group:

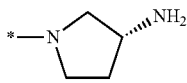

[Formula 8]

(wherein * represents the position for substitution);

(26) the compound according to any one of (1) to (12) or a pharmacologically acceptable salt thereof, wherein Y is the group:

*—CH$_2$—CH$_2$—CH$_2$—NH$_2$   [Formula 9]

(wherein * represents the position for substitution);

(27) the compound according to any one of (1) to (26) or a pharmacologically acceptable salt thereof, wherein all of R$^1$, R$^2$, and R$^3$ are a hydrogen atom;

(28) the compound according to any one of (1) to (27) or a pharmacologically acceptable salt thereof, wherein R$^4$ is a hydrogen atom;

(29) the compound according to any one of (1) to (27) or a pharmacologically acceptable salt thereof, wherein R$^4$ is a prodrug group;

(30) the compound according to (29) or a pharmacologically acceptable salt thereof, wherein the prodrug group represented by R$^4$ is a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group;

(31) the compound according to (29) or a pharmacologically acceptable salt thereof, wherein the prodrug group represented by R$^4$ is a benzyl group or a [(isopropoxycarbonyl)oxy]ethyl group;

(32) a compound represented by the general formula (I-1) or a pharmacologically acceptable salt thereof:

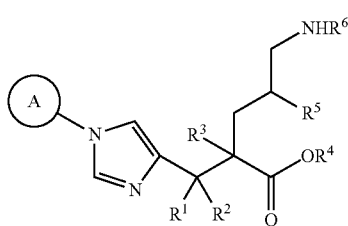

(I-1)

wherein A represents a C3 to C12 cycloalkyl group which may be substituted by one to three identical or different groups selected from a fluoro group, a hydroxy group, a C1 to C6 alkyl group, a C1 to C6 alkoxy group, an aryloxy group, and a heterocyclyloxy group; R$^1$, R$^2$, and R$^3$ each independently represent a hydrogen atom, a fluoro group, or a C1 to C6 alkyl group; R$^4$ represents a hydrogen atom or a prodrug group; R$^5$ represents a hydrogen atom, a C1 to C6 alkyl group, or a C1 to C6 alkoxy group; and R$^6$ represents a hydrogen atom or a prodrug group;

(33) the compound according to (32) or a pharmacologically acceptable salt thereof, wherein A is a cyclobutyl group, a cyclohexyl group, a cycloheptyl group, a bicyclo[3.1.0]hexyl group, a bicyclo[2.2.1]heptyl group, or an adamantyl group, each of which may be substituted by one to three identical or different groups selected from a hydroxy group, a methyl group, and an ethyl group; all of R$^1$, R$^2$, and R$^3$ are a hydrogen atom; R$^4$ is a hydrogen atom; a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group; R$^5$ is a hydrogen atom; and R$^6$ is a hydrogen atom; a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group;

(34) the compound according to (32) or a pharmacologically acceptable salt thereof, wherein A is a cyclohexyl group substituted by one or two identical or different C1 to C6 alkyl groups; all of R$^1$, R$^2$, and R$^3$ are a hydrogen atom; R$^4$ is a hydrogen atom, a benzyl group, or an [(isopropoxycarbonyl)oxy]ethyl group; R$^5$ is a hydrogen atom; and R$^6$ is a hydrogen atom, a phenylalanyl group, an L-norleucyl group, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a ({1-[(cyclohexylcarbonyl)oxy]ethoxy}carbonyl) group, or a (1-acetoxyethoxy)carbonyl group;

(35) a compound represented by the general formula (I-1a) or a pharmacologically acceptable salt thereof:

[Formula 11]

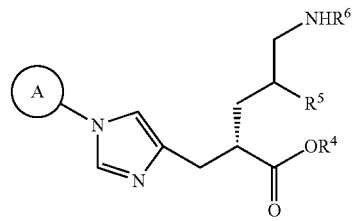

(I-1a)

wherein A represents a cyclobutyl group, a cyclohexyl group, a cycloheptyl group, a bicyclo[3.1.0]hexyl group, a bicyclo[2.2.1]heptyl group, or an adamantyl group, each of which may be substituted by one to three identical or different groups selected from a hydroxy group, a methyl group, and an ethyl group; R$^4$ represents a hydrogen atom; a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group; R$^5$ represents a hydrogen atom, a C1 to C6 alkyl group, or a C1 to C6 alkoxy group; and R$^6$ represents a hydrogen atom; a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group;

(36) the compound according to (35) or a pharmacologically acceptable salt thereof, wherein A is a cyclohexyl group substituted by one or two identical or different C1 to C6 alkyl groups; $R^1$, $R^2$, and $R^3$ are all hydrogen atoms; $R^4$ is a hydrogen atom, a benzyl group, or an [(isopropoxycarbonyl)oxy] ethyl group; $R^5$ is a hydrogen atom; and $R^6$ is a hydrogen atom, a phenylalanyl group, an L-norleucyl group, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a ({1-[(cyclohexylcarbonyl)oxy]ethoxy}carbonyl) group, or a (1-acetoxyethoxy)carbonyl group;

(37) the compound according to (35) or a pharmacologically acceptable salt thereof, wherein A is a cyclohexyl group substituted by a methyl group or an ethyl group; and all of $R^4$, $R^5$, and $R^6$ are a hydrogen atom;

(38) a compound represented by the general formula (I-2) or a pharmacologically acceptable salt thereof:

[Formula 12]

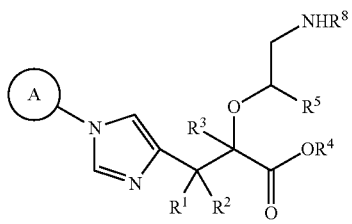

(I-2)

wherein A represents a C3 to C12 cycloalkyl group which may be substituted by one to three identical or different groups selected from a fluoro group, a hydroxy group, a C1 to C6 alkyl group, a C1 to C6 alkoxy group, an aryloxy group, and a heterocyclyloxy group; $R^1$, $R^2$, and $R^3$ each independently represent a hydrogen atom, a fluoro group, or a C1 to C6 alkyl group; $R^4$ represents a hydrogen atom or a prodrug group; $R^7$ represents a hydrogen atom, a C1 to C6 alkyl group, or a C1 to C6 alkoxy group; and $R^8$ represents a hydrogen atom or a prodrug group;

(39) the compound according to (38) or a pharmacologically acceptable salt thereof, wherein A is a cyclobutyl group, a cyclohexyl group, a cycloheptyl group, a bicyclo[3.1.0] hexyl group, a bicyclo[2.2.1]heptyl group, or an adamantyl group, each of which may be substituted by one to three identical or different groups selected from a hydroxy group, a methyl group, and an ethyl group; all of $R^1$, $R^2$, and $R^3$ are a hydrogen atom; $R^4$ is a hydrogen atom; a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group; $R^7$ is a hydrogen atom; and $R^8$ is a hydrogen atom; a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group;

(40) the compound according to (38) or a pharmacologically acceptable salt thereof, wherein A is a cyclohexyl group substituted by one or two identical or different C1 to C6 alkyl groups; all of $R^1$, $R^2$, and $R^3$ are a hydrogen atom; $R^4$ is a hydrogen atom, a benzyl group, or an [(isopropoxycarbonyl) oxy]ethyl group; and both of $R^7$ and $R^8$ are a hydrogen atom;

(41) a compound represented by the general formula (I-2a) or a pharmacologically acceptable salt thereof:

[Formula 13]

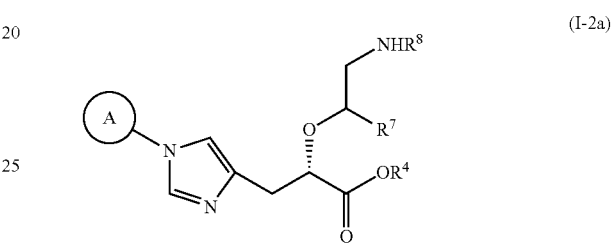

(I-2a)

wherein A represents a cyclobutyl group, a cyclohexyl group, a cycloheptyl group, a bicyclo[3.1.0]hexyl group, a bicyclo[2.2.1]heptyl group, or an adamantyl group, each of which may be substituted by one to three identical or different groups selected from a hydroxy group, a methyl group, and an ethyl group; $R^4$ represents a hydrogen atom; a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group; $R^7$ represents a hydrogen atom, a C1 to C6 alkyl group, or a C1 to C6 alkoxy group; and $R^8$ represents a hydrogen atom or a prodrug group;

(42) the compound according to (41) or a pharmacologically acceptable salt thereof, wherein A is a cyclohexyl group substituted by one or two identical or different C1 to C6 alkyl groups; all of $R^1$, $R^2$, and $R^3$ are a hydrogen atom; $R^4$ is a hydrogen atom, a benzyl group, or an [(isopropoxycarbonyl) oxy]ethyl group; $R^7$ is a hydrogen atom; and $R^8$ is a hydrogen atom; a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group;

(43) the compound according to (41) or a pharmacologically acceptable salt thereof, wherein A is a cyclohexyl group substituted by a methyl group or an ethyl group; and all of $R^4$, $R^7$, and $R^8$ are a hydrogen atom;

(44) a compound represented by the general formula (I-3) or a pharmacologically acceptable salt thereof:

[Formula 14]

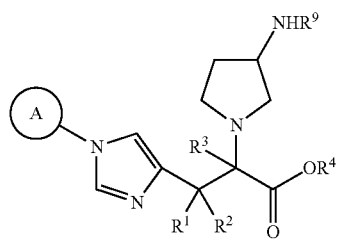

(I-3)

wherein A represents a C3 to C12 cycloalkyl group which may be substituted by one to three identical or different groups selected from a fluoro group, a hydroxy group, a C1 to C6 alkyl group, a C1 to C6 alkoxy group, an aryloxy group, and a heterocyclyloxy group; $R^1$, $R^2$, and $R^3$ each independently represent a hydrogen atom, a fluoro group, or a C1 to C6 alkyl group; $R^4$ represents a hydrogen atom or a prodrug group; and $R^9$ represents a hydrogen atom or a prodrug group;

(45) the compound according to (44) or a pharmacologically acceptable salt thereof, wherein A is a cyclobutyl group, a cyclohexyl group, a cycloheptyl group, a bicyclo[3.1.0]hexyl group, a bicyclo[2.2.1]heptyl group, or an adamantyl group, each of which may be substituted by one to three identical or different groups selected from a hydroxy group, a methyl group, and an ethyl group; all of $R^1$, $R^2$, and $R^3$ are a hydrogen atom; $R^4$ is a hydrogen atom; a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group; and $R^9$ is a hydrogen atom; a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group;

(46) the compound according to (44) or a pharmacologically acceptable salt thereof, wherein A is a cyclohexyl group substituted by one or two identical or different C1 to C6 alkyl groups; all of $R^1$, $R^2$, and $R^3$ are a hydrogen atom; $R^4$ is a hydrogen atom, a benzyl group, or an [(isopropoxycarbonyl)oxy]ethyl group; and $R^9$ is a hydrogen atom;

(47) a compound represented by the general formula (I-3a) or a pharmacologically acceptable salt thereof:

[Formula 15]

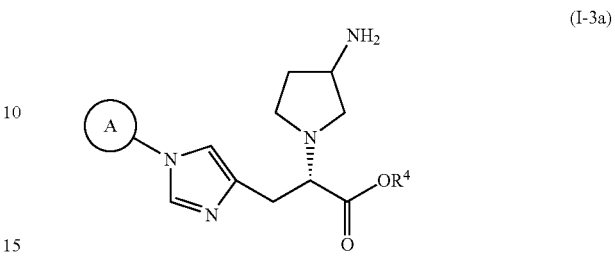

(I-3a)

wherein A represents a cyclobutyl group, a cyclohexyl group, a cycloheptyl group, a bicyclo[3.1.0]hexyl group, a bicyclo[2.2.1]heptyl group, or an adamantyl group, each of which may be substituted by one to three identical or different groups selected from a hydroxy group, a methyl group, and an ethyl group; and $R^4$ represents a hydrogen atom; a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group;

(48) the compound according to (47) or a pharmacologically acceptable salt thereof, wherein A is a cyclohexyl group substituted by one or two identical or different C1 to C6 alkyl groups; and $R^4$ is a hydrogen atom, a benzyl group, or an [(isopropoxycarbonyl)oxy]ethyl group;

(49) the compound according to (48) or a pharmacologically acceptable salt thereof, wherein A is a cyclohexyl group substituted by a methyl group or an ethyl group; and $R^4$ is a hydrogen atom;

(50) the compound according to (1) or a pharmacologically acceptable salt thereof, wherein the compound is selected from the group consisting of 5-amino-2-[(1-cyclohexyl-1H-imidazol-4-yl)methyl]valeric acid, 5-amino-2-{[1-(4-methylcyclohexyl)-1H-imidazol-4-yl]methyl}valeric acid, 5-amino-2-{[1-(4-ethylcyclohexyl)-1H-imidazol-4-yl]methyl}valeric acid, 5-amino-2-{[1-(3-ethylcyclobutyl)-1H-imidazol-4-yl]methyl}valeric acid, 5-amino-2-{[1-(3-methylcyclobutyl)-1H-imidazol-4-yl]methyl}valeric acid, 5-amino-2-({1-[(1R,3s,5S)-bicyclo[3.1.0]hexan-3-yl]-1H-imidazol-4-yl}methyl)valeric acid, 5-amino-2-{[1-(4-hydroxycyclohexyl)-1H-imidazol-4-yl]methyl}valeric acid, 5-amino-2-{[1-(4-hydroxy-4-methylcyclohexyl)-1H-imidazol-4-yl]methyl}valeric acid, 5-amino-2-{[1-(3-methylcyclohexyl)-1H-imidazol-4-yl]methyl}valeric acid, 5-amino-2-[(1-cycloheptyl-1H-imidazol-4-yl)methyl]valeric acid, 5-amino-2-({1-[exo-bicyclo[2.2.1]hept-2-yl]-1H-imidazol-4-yl}methyl)valeric acid, 5-amino-2-({1-[endo-bicyclo[2.2.1]hept-2-yl]-1H-imidazol-4-yl}methyl)valeric acid, 2-[(1-adamantan-2-yl-1H-imidazol-4-yl)methyl]-5-aminovaleric acid, 5-amino-2-{[1-(4-phenoxycyclohexyl)-1H-imidazol-4-yl]methyl}valeric acid, Benzyl 5-amino-2-{[1-(4-methylcyclohexyl)-1H-imidazol-4-yl]methyl}valerate, 2-{[1-(4-methylcyclohexyl)-1H-imidazol-4-yl]methyl}-5-(L-phenylalanylamino)valeric acid, 2-{[1-(4-methylcyclohexyl)-1H-imidazol-4-yl]methyl}-5-(L-norleucylamino)valeric acid, 2-{[1-(4-methylcyclohexyl)-1H-imidazol-4-yl]methyl}-5-({[(5-methyl-2-oxo-1,3-dioxol-4-yl)methoxy]carbonyl}amino)valeric acid, 5-({[1-(isobutyryloxy)ethoxy]carbonyl}amino)-2-{[1-(4-methylcyclohexyl)-1H-imidazol-4-yl]methyl}valeric acid, 1-[(isopropoxycarbonyl)oxy]ethyl 5-({[1-(isobutyryloxy)ethoxy]carbonyl}amino)-2-{[1-(4-methylcyclohexyl)-1H-imidazol-4-yl]methyl}valerate, 5-({[1-(2,2-dimethylpropanoyloxy)ethoxy]carbonyl}amino)-2-{[1-(4-methylcyclohexyl)-1H-imidazol-4-yl]methyl}valeric acid, 5-[({1-[(cyclohexylcarbonyl)oxy]ethoxy}carbonyl)amino]-2-{[1-(4-methylcyclohexyl)-1H-imidazol-4-yl]methyl}valeric acid, 2-(2-aminoethoxy)-3-[1-(4-methylcyclohexyl)-1H-imidazol-4-yl]propionic acid, 2-[(1R)-2-amino-1-methylethoxy]-3-[1-(4-methylcyclohexyl)-1H-imidazol-4-yl]propionic acid, and 2-[(3S)-3-aminopyrrolidin-1-yl]-3-[1-(4-methylcyclohexyl)-1H-imidazol-4-yl]propionic acid;

(51) 5-amino-2-{[1-(4-methylcyclohexyl)-1H-imidazol-4-yl]methyl}valeric acid or a pharmacologically acceptable salt thereof;

(52) 5-amino-2-{[1-(trans-4-methylcyclohexyl)-1H-imidazol-4-yl]methyl}valeric acid or a pharmacologically acceptable salt thereof;

(53) (2S)-5-amino-2-{([1-(trans-4-methylcyclohexyl)-1H-imidazol-4-yl]methyl}valeric acid or a pharmacologically acceptable salt thereof;

(54) a pharmacologically acceptable salt of the compound according to any one of (1) to (53), wherein the pharmacologically acceptable salt is p-toluenesulfonate or benzenesulfonate;

(55) (2S)-5-amino-2-{[1-(trans-4-methylcyclohexyl)-1H-imidazol-4-yl]methyl}valeric acid;

(56) (2S)-5-amino-2-{[1-(trans-4-methylcyclohexyl)-1H-imidazol-4-yl]methyl}valeric acid benzenesulfonate;

(57) (2S)-5-amino-2-{[1-(trans-4-methylcyclohexyl)-1H-imidazol-4-yl]methyl}valeric acid p-toluenesulfonate;

(58) (2S)-5-amino-2-{[1-(trans-4-methylcyclohexyl)-1H-imidazol-4-yl]methyl}valeric acid p-toluenesulfonate anhydrate;

(59) the (2S)-5-amino-2-{[1-(trans-4-methylcyclohexyl)-1H-imidazol-4-yl]methyl}valeric acid p-toluenesulfonate anhydrate according to (58), which is in crystalline form exhibiting main peaks at interplanar spacings d of 23.9, 11.9, 4.5, 4.3, and 3.6 angstroms in powder X-ray diffraction obtained by copper Kα radiation;

(60) (2S)-5-amino-2-{[1-(trans-4-methylcyclohexyl)-1H-imidazol-4-yl]methyl}valeric acid p-toluenesulfonate monohydrate;

(61) the (2S)-5-amino-2-{[1-(trans-4-methylcyclohexyl)-1H-imidazol-4-yl]methyl}valeric acid p-toluenesulfonate monohydrate according to (60), which is in crystalline form exhibiting main peaks at interplanar spacings d of 22.9, 5.0, 4.9, 4.7, and 4.0 angstroms in powder X-ray diffraction obtained by copper Kα radiation;

(62) a pharmaceutical drug containing a compound according to any one of (1) to (61) or a pharmacologically acceptable salt thereof as an active ingredient;

(63) a TAFIa inhibitor containing a compound according to any one of (1) to (61) or a pharmacologically acceptable salt thereof as an active ingredient;

(64) a fibrinolysis promoter containing a compound according to any one of (1) to (61) or a pharmacologically acceptable salt thereof as an active ingredient;

(65) a preventive or therapeutic drug for a disease caused by inhibition of fibrinolysis containing a compound according to any one of (1) to (61) or a pharmacologically acceptable salt thereof as an active ingredient;

(66) a preventive or therapeutic drug for thrombosis or embolism or a sequela thereof including: acute coronary syndrome such as myocardial infarction and angina pectoris (stable angina and unstable angina); venous thromboembolism such as deep vein thrombosis and pulmonary embolism; thrombosis or embolism occurring in the cardiovascular system after surgical operation such as vessel revascularization, angioplasty, stent placement, and bypass surgery; thrombosis or embolism after artificial joint replacement operation such as knee joint replacement operation and hip joint replacement operation; inflammation-related intravascular disease such as sepsis and disseminated intravascular coagulation syndrome (DIC); peripheral vascular disorder-derived or -related disease such as peripheral arterial occlusion (PAO), arteriosclerosis, and diabetes mellitus; tumor-related disease such as solid cancer and blood cancer; and organ disorder attributed to thrombus or embolus such as pulmonary embolus, cerebral infarction, and renal infarction, containing a compound according to any one of (1) to (61) or a pharmacologically acceptable salt thereof as an active ingredient;

(67) a preventive or therapeutic drug for thrombosis or embolism including: disease caused by contact with foreign matter in the body, the foreign matter including a medical device such as a joint prosthesis used in joint replacement, a vascular catheter, a blood prosthesis, a blood stent, and prosthetic valve; and disease caused by contact between blood and a medical device outside the body, the medical device including a pump oxygenator used in cardiac operation and a medical device used in hemodialysis, containing a compound according to any one of (1) to (61) or a pharmacologically acceptable salt thereof as an active ingredient;

(68) a preventive or therapeutic drug for a disease related to thrombosis or embolism or accompanied by fibrin deposition or fibrosis including: pulmonary disease such as pulmonary hypertension, adult respiratory distress syndrome, pulmonary fibrosis, and chronic thromboembolic pulmonary hypertension; renal disease such as glomerulonephritis (including acute glomerulonephritis, chronic glomerulonephritis, nephrotic nephritis, and rapidly progressive glomerulonephritis), renal infarction, and diabetic nephritis; hepatic disease such as hepatic fibrosis, hepatitis, and hepatic cirrhosis; eye disease associated with fibrin deposition in the eye; organ dysfunction after organ transplantation or resection; microcirculatory disorder caused by microthrombus, including thrombotic microangiopathy; and disease or symptoms associated with cancer cell migration or metastasis, containing a compound according to any one of (1) to (61) or a pharmacologically acceptable salt thereof as an active ingredient.

(69) a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis, containing a compound according to any one of (1) to (61) or a pharmacologically acceptable salt thereof as an active ingredient;

(70) a pharmaceutical composition containing a compound according to any one of (1) to (61) or a pharmacologically acceptable salt thereof and a pharmacologically acceptable carrier;

(71) a method for treating myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis, comprising administering a pharmaceutical composition containing a compound according to any one of (1) to (61) or a pharmacologically acceptable salt thereof as an active ingredient;

(72) the compound according to any one of (1) to (61) or a pharmacologically acceptable salt thereof for use in the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis;

(73) a pharmaceutical drug for injection containing a compound according to any one of (1) to (61) or a pharmacologically acceptable salt thereof as an active ingredient;

(74) a TAFIa inhibitor for injection containing a compound according to any one of (1) to (61) or a pharmacologically acceptable salt thereof as an active ingredient;

(75) a therapeutic drug for injection for myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis containing a compound according to any one of (1) to (61) or a pharmacologically acceptable salt thereof as an active ingredient;

(76) a therapeutic drug for injection for a thromboembolism-derived disease containing a compound according to any one of (1) to (61) or a pharmacologically acceptable salt thereof as an active ingredient;

(77) a pharmaceutical composition for injection containing a compound according to any one of (1) to (61) or a pharmacologically acceptable salt thereof and a pharmacologically acceptable carrier;

(78) a method for treating myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis, comprising administering a pharmaceutical composition for injection containing a compound according to any one of (1) to (61) or a pharmacologically acceptable salt thereof as an active ingredient;

(79) the compound according to any one of (1) to (61) or a pharmacologically acceptable salt thereof for use in the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis by injection; and

(80) a pharmaceutical composition containing a compound according to any one of (1) to (61) or a pharmacologically acceptable salt thereof and one or two or more drugs selected from an anticoagulant, an antiplatelet drug, an enzyme related to fibrinolysis, an anticancer drug, an anti-inflammatory drug, an antifibrotic drug, a hypotensive drug, an anti-pulmonary hypertension drug, and an immunosuppressive drug as active ingredients.

The present invention also provides as production intermediates of a cycloalkyl-substituted imidazole derivative having the general formula (I) or a pharmacologically acceptable salt thereof:

(81) a compound represented by the following general formula or a salt thereof:

[Formula 16]

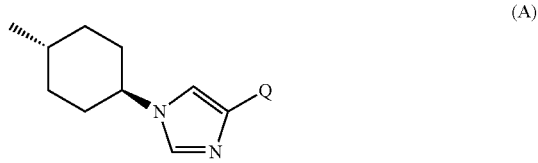

(A)

wherein Q represents a group COOR, a hydroxymethyl group, or a formyl group, and R represents a C1 to C6 alkyl group;

(82) a compound represented by the following general formula or a salt thereof:

[Formula 17]

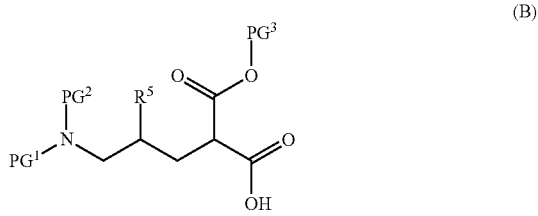

(B)

wherein $R^5$ is as defined above; $PG^1$ represents a protective group for the amino group; $PG^2$ represents a hydrogen atom or a protective group for the amino group; and $PG^3$ represents a protective group for the carboxy group; and

(83) a compound represented by the following general formula or a salt thereof:

[Formula 18]

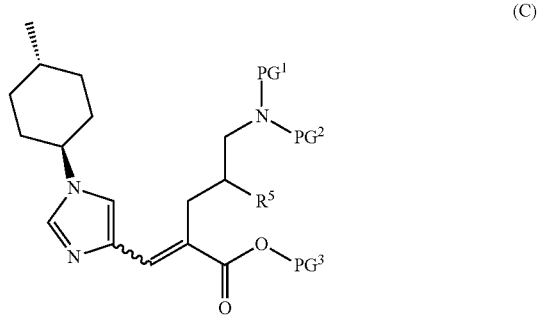

(C)

wherein $R^5$, $PG^1$, $PG^2$, and $PG^3$ are as defined above.

Advantageous Effects of the Invention

A cycloalkyl-substituted imidazole derivative of the present invention represented by the general formula (I) or a pharmacologically acceptable salt thereof has excellent TAFIa inhibitory activity and exhibits good oral absorbability, plasma concentration, and retention in blood, and excellent pharmacological effect. Moreover, the compound of the general formula (I) of the present invention or the pharmacologically acceptable salt thereof is excellent in disposition such as biodistribution and retention in blood, free from prolongation of bleeding time, and also highly safe.

Therefore, the cycloalkyl-substituted imidazole derivative of the present invention represented by the general formula (I) or the pharmacologically acceptable salt thereof is useful as a pharmaceutical drug (particularly, a preventive or therapeutic drug, preferably a therapeutic drug, for a disease caused by inhibition of fibrinolysis) and particularly useful as a preventive or therapeutic drug (preferably a therapeutic drug) for thrombosis or embolism or a sequela thereof including: acute coronary syndrome such as myocardial infarction and angina pectoris (stable angina and unstable angina); venous thromboembolism such as deep vein thrombosis and pulmonary embolism; thrombosis or embolism occurring in the cardiovascular system after a surgical operation such as vessel revascularization, angioplasty, stent placement, and bypass surgery; thrombosis or embolism after an artificial joint replacement operation such as a knee joint replacement operation and a hip joint replacement operation; inflammation-related intravascular disease such as sepsis and disseminated intravascular coagulation syndrome (DIC); peripheral vascular disorder-derived or -related disease such as peripheral arterial occlusion (PAO), arteriosclerosis, and diabetes mellitus; tumor-related disease such as solid cancer and blood cancer; and organ disorder attributed to thrombus or embolus such as pulmonary embolus, cerebral infarction, and renal infarction. Moreover, the compound of the present invention is useful as a preventive or therapeutic drug (preferably a therapeutic drug) for thrombosis or embolism including: disease caused by contact with foreign matter in the body, for example, a medical device such as a joint prosthesis used in joint replacement, a vascular catheter, a blood prosthesis, a blood stent, and prosthetic valve; and disease caused by contact between blood and a medical device outside the body, for example, a pump oxygenator used in cardiac operations and a medical device used in hemodialysis. Furthermore, the compound of the present invention is useful as a preventive or therapeutic drug (preferably a therapeutic drug) for a disease related to thrombosis or embolism or accompanied by fibrin deposition or fibrosis, for example, a preventive or therapeutic drug (preferably a therapeutic drug) for pulmonary disease such as pulmonary hypertension, adult respiratory distress syndrome, pulmonary fibrosis, and chronic thromboembolic pulmonary hypertension; renal disease such as glomerulonephritis (acute glomerulonephritis, chronic glomerulonephritis, nephrotic nephritis, rapidly progressive glomerulonephritis, etc.), renal infarction, and diabetic nephritis; hepatic disease such as hepatic fibrosis, hepatitis, and hepatic cirrhosis; eye disease associated with fibrin deposition in the eye; organ dysfunction after organ transplantation or resection; microcirculatory disorder caused by microthrombus, including thrombotic microangiopathy; and disease or symptoms associated with cancer cell migration or metastasis.

DESCRIPTION OF EMBODIMENTS

Figure 1:
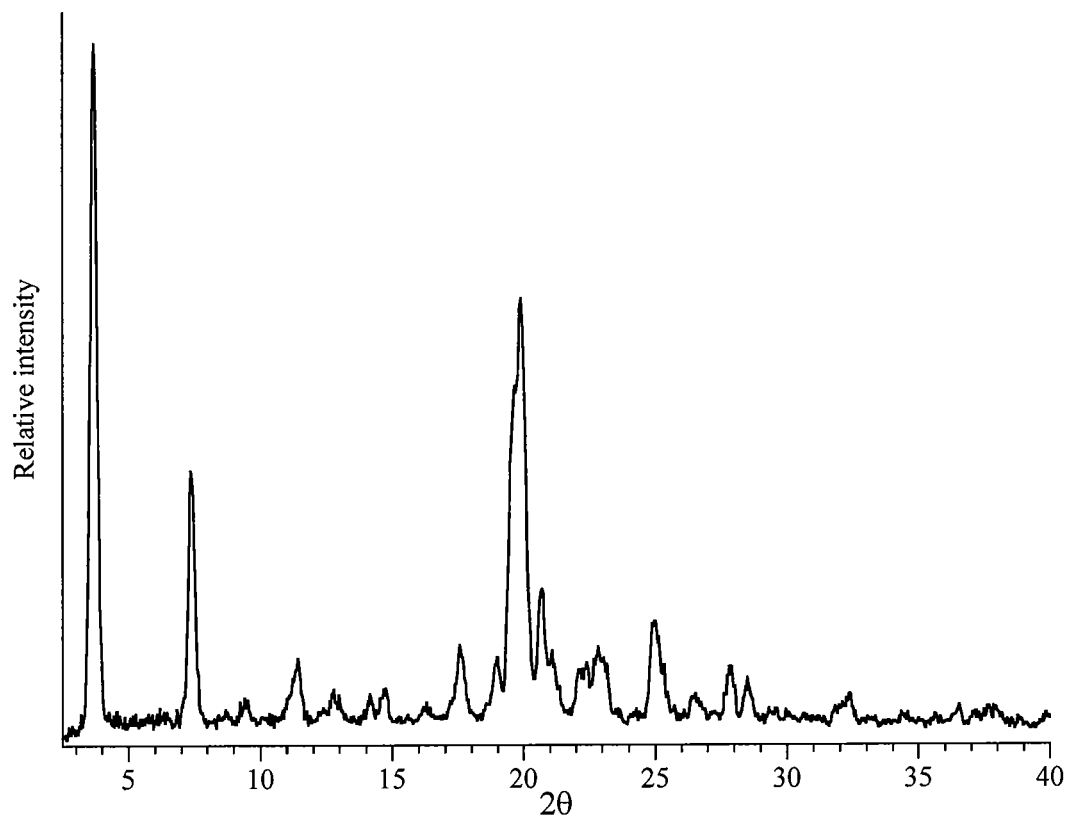
FIG. 1 shows the results of irradiating type I crystals of (2S)-5-amino-2-{[1-(trans-4-methylcyclohexyl)-1H-imidazol-4-yl]methyl}valeric acid p-toluenesulfonate anhydrate with Cu Kα X-rays of 1.54 angstroms in a Bruker transmission-type HT-compatible powder X-ray diffractometer equipped with a two-dimensional detector, D8 DISCOVER with GADDS CST, and measuring powder X-ray diffraction data using a Mylar film. In this powder X-ray diffraction pattern, the ordinate represents diffraction intensity indicated in count/second (cps) units, and the abscissa represents diffraction angles indicated in 2θ values. Peak position is within the range of 2θ±0.2°.

Hereinafter, substituents in the present specification will be described.

A "halogeno group" means a fluoro, chloro, bromo, or iodo group, i.e., a fluorine, chlorine, bromine, or iodine atom.

A "C1 to C6 alkyl group" means a linear or branched saturated hydrocarbon group having 1 to 6 carbon atoms. Examples thereof include methyl, ethyl, propyl, isopropyl, n-butyl, sec-butyl, tert-butyl, isobutyl, n-pentyl, n-hexyl, 1-ethylpropyl, and 2,2-dimethylpropyl groups.

A "C1 to C6 alkoxy group" means a linear or branched alkyloxy group having 1 to 6 carbon atoms. Examples thereof include methoxy, ethoxy, propoxy, isopropoxy, and tert-butoxy groups.

A "(C1 to C6 alkoxy)carbonyl group" means a group consisting of the C1 to C6 alkoxy group and a carbonyl group. Examples thereof include methoxycarbonyl, ethoxycarbonyl, and isopropoxycarbonyl groups.

A "C1 to C6 alkanoyl group" means a linear or branched alkanoyl group having 1 to 6 carbon atoms. Examples thereof include formyl, acetyl, propionyl, butyryl, isobutyryl, valeryl, isovaleryl, pivaloyl, and hexanoyl groups.

A "C2 to C6 alkanoyloxy group" means a group consisting of a linear or branched alkanoyl group having 2 to 6 carbon atoms, and an oxy group. Examples thereof include acetyloxy, propionyloxy, and hexanoyloxy groups.

A "C3 to C12 cycloalkyl group" means a saturated hydrocarbon ring having 3 to 12 carbon atoms and encompasses: monocycloalkyl groups exemplified by cyclopropyl, cyclobutyl, cyclopentyl, cyclohexyl, cycloheptyl, and cyclooctyl groups as well as polycycloalkyl groups, for example, bicycloalkyl and tricycloalkyl groups. Examples of the bicycloalkyl group include norbornyl groups, for example, exo-2-norbornyl, endo-2-norbornyl, 3-pinanyl, bicyclo[3.1.0]hexyl, bicyclo[2.2.1]heptyl, and bicyclo[2.2.2]

oct-2-yl groups. Examples of the tricycloalkyl group include adamantyl groups, for example, 1-adamantyl and 2-adamantyl groups.

A "(C3 to C6 cycloalkyl)carbonyloxy group" means a group consisting of a saturated hydrocarbon ring having 3 to 6 carbon atoms, and a carbonyloxy group. Examples thereof include cyclopropylcarbonyloxy and cyclohexylcarbonyloxy groups.

An "aryl group" means an aryl group having 6 to 14 carbon atoms. Examples thereof include phenyl, naphthyl, anthryl, and phenanthryl groups.

A "heterocyclyl group" means a monocyclic or bicyclic 3- to 10-membered saturated or unsaturated heterocyclic group containing 1 to 3 atoms selected from the group consisting of nitrogen, oxygen, and sulfur atoms. Examples thereof include aziridinyl, azetidinyl, pyrrolidinyl, morpholinyl, pyrrolyl, furyl, thienyl, pyrazolyl, imidazolyl, oxazolyl, isothiazolyl, pyranyl, pyridyl, pyridazinyl, pyrimidinyl, pyrazinyl, benzimidazolyl, benzoxazolyl, quinolyl, pyrrolinyl, imidazolinyl, pyrazolinyl, dihydropyridyl, and tetrahydropyridyl groups.

An "aryloxy group" means a group consisting of the aryl group and an oxy group. Examples thereof include phenoxy and naphthoxy groups.

A "heterocyclyloxy group" means a group consisting of the heterocyclyl group and an oxy group. Examples thereof include pyrrolidin-3-yloxy and pyridin-4-yloxy groups.

A "heterocyclylalkyl group" means a group consisting of the heterocyclyl group and the C1 to C6 alkyl group. Examples thereof include a 1,3-dioxol-4-ylmethyl group.

A "heterocyclylalkyloxycarbonyl group" means a group consisting of the heterocyclyl group, the C1 to C6 alkoxy group, and a carbonyl group. Examples thereof include a 1,3-dioxol-4-ylmethoxycarbonyl group.

A "prodrug group" means a group that is converted through reaction with an enzyme, gastric acid, or the like under physiological conditions in vivo to produce a compound (I) serving as an active ingredient of a pharmaceutical composition of the present invention, i.e., a group that is converted to produce the compound (I) through enzymatic oxidation, reduction, hydrolysis, or the like, or a group that is converted to produce the compound (I) through hydrolysis or the like caused by gastric acid or the like. Examples thereof include phenylalanyl, L-norleucyl, [(5-methyl-2-oxo-1,3-dioxol-4-yl)methoxy]carbonyl, [1-(isobutyryloxy)ethoxy]carbonyl, [1-(2,2-dimethylpropanoyloxy)ethoxy]carbonyl, {1-[(cyclohexylcarbonyl)oxy]ethoxy}carbonyl, (1-acetoxyethoxy)carbonyl, benzyl, and [(isopropoxycarbonyl)oxy]ethyl groups. The prodrug group represented by $R^4$ is a prodrug group for a carboxy group and is preferably a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group; more preferably a benzyl group or an [(isopropoxycarbonyl)oxy]ethyl group. The prodrug group represented by $R^6$, $R^8$, or $R^9$ is a prodrug group for an amino group and is preferably a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy) carbonyl group which may be substituted by one to three identical or different groups selected from a C1 to C6 alkyl group, a C2 to C6 alkanoyloxy group, a (C3 to C6 cycloalkyl) carbonyloxy group, and an aryl group; or a heterocyclylalkyloxycarbonyl group which may be substituted by one to three identical or different groups selected from an oxo group and a C1 to C6 alkyl group; more preferably a phenylalanyl group, an L-norleucyl group, a [(5-methyl-2-oxo-1,3-dioxol-4-yl) methoxy]carbonyl group, a [1-(isobutyryloxy)ethoxy]carbonyl group, a [1-(2,2-dimethylpropanoyloxy)ethoxy]carbonyl group, a ({1-[(cyclohexylcarbonyl)oxy]ethoxy}carbonyl) group, or a (1-acetoxyethoxy)carbonyl group.

Hereinafter, the compound of the general formula (I) will be described in detail.

[Formula 19]

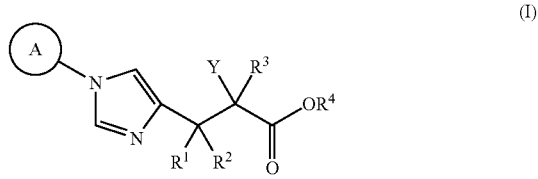

(I)

wherein A represents a C3 to C12 cycloalkyl group which may be substituted by one to three identical or different groups selected from a fluoro group, a hydroxy group, a C1 to C6 alkyl group, a C1 to C6 alkoxy group, an aryloxy group, and a heterocyclyloxy group; $R^1$, $R^2$, and $R^3$ each independently represent a hydrogen atom, a fluoro group, or a C1 to C6 alkyl group; $R^4$ represents a hydrogen atom or a prodrug group; and Y represents a group: —$CH_2$—$CHR^5$—$CH_2$—$NHR^6$ (wherein $R^5$ represents a hydrogen atom, a C1 to C6 alkyl group, or a C1 to C6 alkoxy group, and $R^6$ represents a hydrogen atom or a prodrug group), —O—$CHR^7$—$CH_2$—$NHR^8$ (wherein $R^7$ represents a hydrogen atom, a C1 to C6 alkyl group, or a C1 to C6 alkoxy group, and $R^8$ represents a hydrogen atom or a prodrug group), or

[Formula 20]

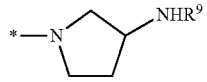

(wherein $R^9$ represents a hydrogen atom or a prodrug group, and * represents the position for substitution).

A represents a C3 to C12 cycloalkyl group which may be substituted by one to three identical or different groups selected from a fluoro group, a hydroxy group, a C1 to C6 alkyl group, a C1 to C6 alkoxy group, an aryloxy group, and a heterocyclyloxy group. A is preferably a cyclobutyl group, a cyclohexyl group, a cycloheptyl group, a bicyclo[3.1.0] hexyl group, a bicyclo[2.2.1]heptyl group, or an adamantyl group, each of which may be substituted by one to three identical or different groups selected from a fluoro group, a hydroxy group, a C1 to C6 alkyl group, a C1 to C6 alkoxy group, an aryloxy group, and a heterocyclyloxy group; more preferably a cyclobutyl group, a cyclohexyl group, a cycloheptyl group, a bicyclo[3.1.0]hexyl group, a bicyclo[2.2.1] heptyl group, or an adamantyl group, each of which may be substituted by one to three identical or different groups selected from a hydroxy group, a methyl group, and an ethyl group.

Moreover, A is preferably a cyclohexyl group which may be substituted by one to three identical or different groups selected from a fluoro group, a hydroxy group, a C1 to C6 alkyl group, a C1 to C6 alkoxy group, an aryloxy group, and a heterocyclyloxy group.

Moreover, A is preferably a C3 to C12 cycloalkyl group which may be substituted by one or two identical or different C1 to C6 alkyl groups, more preferably a C3 to C12 cycloalkyl group substituted by one C1 to C6 alkyl group, even more preferably a C3 to C12 cycloalkyl group substituted by a methyl group or an ethyl group.

Moreover, A is preferably a cyclohexyl group which may be substituted by one or two identical or different C1 to C6 alkyl groups, more preferably a cyclohexyl group substituted by one C1 to C6 alkyl group, even more preferably a cyclohexyl group substituted by a methyl group or an ethyl group.

Specifically, A is preferably a group:

[Formula 21]

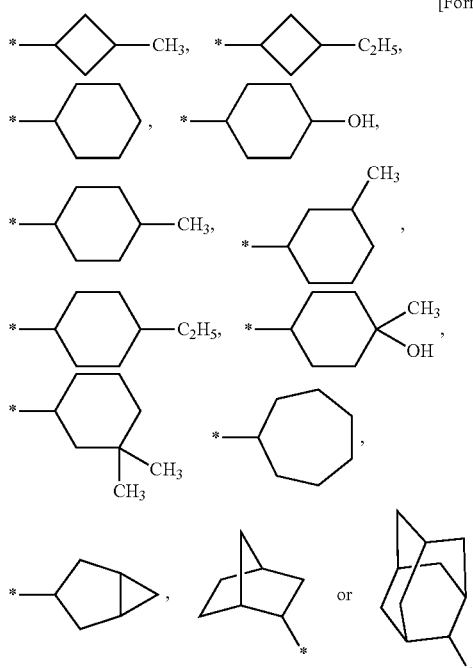

more preferably a group:

[Formula 22]

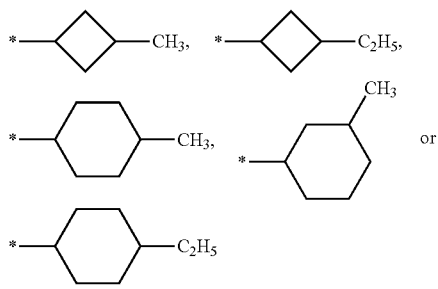

even more preferably the group:

[Formula 23]

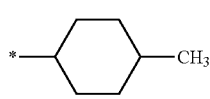

particularly preferably the group:

[Formula 24]

Y represents a group: —CH$_2$—CHR$^5$—CH$_2$—NHR$^6$ (wherein R$^5$ represents a hydrogen atom, a C1 to C6 alkyl group, or a C1 to C6 alkoxy group, and R$^6$ represents a hydrogen atom or a prodrug group), —O—CHR$^7$—CH$_2$—NHR$^8$ (wherein R$^7$ represents a hydrogen atom, a C1 to C6 alkyl group, or a C1 to C6 alkoxy group, and R$^8$ represents a hydrogen atom or a prodrug group), or

[Formula 25]

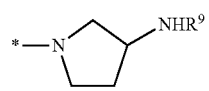

(wherein R$^9$ represents a hydrogen atom or a prodrug group, and * represents the position for substitution).

Hereinafter, the case where Y is the group: —CH$_2$—CHR$^5$—CH$_2$—NHR$^6$ (wherein R$^5$ represents a hydrogen atom, a C1 to C6 alkyl group, or a C1 to C6 alkoxy group, and R$^6$ represents a hydrogen atom or a prodrug group) will be described in detail.

R$^5$ represents a hydrogen atom, a C1 to C6 alkyl group, or a C1 to C6 alkoxy group and is preferably a hydrogen atom or a methyl group, more preferably a hydrogen atom.

R$^6$ represents a hydrogen atom or a prodrug group. In this context, the prodrug group is a prodrug group for an amino group and is preferably a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group; more preferably a phenylalanyl group, an L-norleucyl group, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a {1-[(cyclohexylcarbonyl)oxy]ethoxy}carbonyl group, or a (1-acetoxyethoxy)carbonyl group.

Y is preferably the group:

*—CH$_2$—CH$_2$—CH$_2$—NH$_2$     [Formula 26]

(wherein * represents the position for substitution).

Hereinafter, the case where Y is the group: —O—CHR$^7$—CH$_2$—NHR$^8$ (wherein R$^7$ represents a hydrogen atom, a C1 to C6 alkyl group, or a C1 to C6 alkoxy group, and R$^8$ represents a hydrogen atom or a prodrug group) will be described in detail.

R$^7$ represents a hydrogen atom, a C1 to C6 alkyl group, or a C1 to C6 alkoxy group and is preferably a hydrogen atom or a methyl group, more preferably a hydrogen atom.

R$^8$ represents a hydrogen atom or a prodrug group. In this context, the prodrug group is a prodrug for an amino group and is preferably a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group; more preferably a phenylalanyl group, an L-norleucyl group, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a {1-[(cyclohexylcarbonyl)oxy]ethoxy}carbonyl group, or a (1-acetoxyethoxy)carbonyl group. $R^8$ is preferably a hydrogen atom.

Hereinafter, the case will be described in detail where Y is the group:

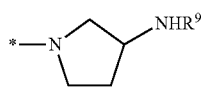

[Formula 27]

(wherein $R^9$ represents a hydrogen atom or a prodrug group, and * represents the position for substitution).

$R^9$ represents a hydrogen atom or a prodrug group. In this context, the prodrug group is a prodrug group for an amino group and is preferably a C1 to C6 alkanoyl group which may be substituted by one to three identical or different groups selected from an amino group, a halogeno group, a hydroxy group, a carboxy group, a carbamoyl group, a C1 to C6 alkoxy group, an aryl group, and a heterocyclyl group; a (C1 to C6 alkoxy)carbonyl group which may be substituted by one to three identical or different groups selected from a C1 to C6 alkyl group, a C2 to C6 alkanoyloxy group, a (C3 to C6 cycloalkyl)carbonyloxy group, and an aryl group; or a heterocyclylalkyloxycarbonyl group which may be substituted by one to three identical or different groups selected from an oxo group and a C1 to C6 alkyl group; more preferably a phenylalanyl group, an L-norleucyl group, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a {1-[(cyclohexylcarbonyl)oxy]ethoxy}carbonyl group, or a (1-acetoxyethoxy)carbonyl group. $R^9$ is preferably a hydrogen atom.

Y is preferably the group

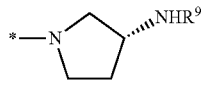

[Formula 28]

(wherein $R^9$ represents a hydrogen atom or a prodrug group, and * represents the position for substitution), more preferably the group:

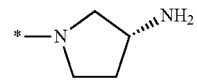

[Formula 29]

(wherein * represents the position for substitution).

Y is preferably the group: —$CH_2$—$CHR^5$—$CH_2$—$NHR^6$ (wherein $R^5$ represents a hydrogen atom, a C1 to C6 alkyl group, or a C1 to C6 alkoxy group, and $R^6$ represents a hydrogen atom or a prodrug group).

$R^1$, $R^2$, and $R^3$ each independently represent a hydrogen atom, a fluoro group, or a C1 to C6 alkyl group. All of $R^1$, $R^2$, and $R^3$ are preferably a hydrogen atom. In this context, the C1 to C6 alkyl group is preferably a methyl group.

$R^4$ represents a hydrogen atom or a prodrug group. In this context, the prodrug group is a prodrug for a carboxy group and is preferably a C1 to C6 alkyl group which may be substituted by one to three identical or different groups selected from a C2 to C6 alkanoyloxy group, a (C3 to C6 cycloalkyl)carbonyloxy group, and an aryl group; or a heterocyclylalkyl group which may be substituted by one to three identical or different groups selected from an oxo group and a C1 to C6 alkyl group; more preferably a benzyl group or a [(isopropoxycarbonyl)oxy]ethyl group. $R^4$ is preferably a hydrogen atom.

Preferable specific examples of the compound represented by the general formula (I) include the following:

5-amino-2-[(1-cyclohexyl-1H-imidazol-4-yl)methyl]valeric acid,
5-amino-2-{[1-(4-methylcyclohexyl)-1H-imidazol-4-yl]methyl}valeric acid,
5-amino-2-{[1-(4-ethylcyclohexyl)-1H-imidazol-4-yl]methyl}valeric acid,
5-amino-2-{[1-(3-ethylcyclobutyl)-1H-imidazol-4-yl]methyl}valeric acid,
5-amino-2-{[1-(3-methylcyclobutyl)-1H-imidazol-4-yl]methyl}valeric acid,
5-amino-2-({1-[(1R,3s,5S)-bicyclo[3.1.0]hexan-3-yl]-1H-imidazol-4-yl}methyl)valeric acid,
5-amino-2-{[1-(4-hydroxycyclohexyl)-1H-imidazol-4-yl]methyl}valeric acid,
5-amino-2-{[1-(4-hydroxy-4-methylcyclohexyl)-1H-imidazol-4-yl]methyl}valeric acid,
5-amino-2-{[1-(3-methylcyclohexyl)-1H-imidazol-4-yl]methyl}valeric acid,
5-amino-2-[(1-cycloheptyl-1H-imidazol-4-yl)methyl]valeric acid,
5-amino-2-({1-[exo-bicyclo[2.2.1]hept-2-yl]-1H-imidazol-4-yl}methyl)valeric acid,
5-amino-2-({1-[endo-bicyclo[2.2.1]hept-2-yl]-1H-imidazol-4-yl}methyl)valeric acid,
2-[(1-adamantan-2-yl-1H-imidazol-4-yl)methyl]-5-aminovaleric acid,
5-amino-2-{[1-(4-phenoxycyclohexyl)-1H-imidazol-4-yl]methyl}valeric acid,
Benzyl 5-amino-2-{[1-(4-methylcyclohexyl)-1H-imidazol-4-yl]methyl}valerate,
2-{[1-(4-methylcyclohexyl)-1H-imidazol-4-yl]methyl}-5-(L-phenylalanylamino)valeric acid,
2-{[1-(4-methylcyclohexyl)-1H-imidazol-4-yl]methyl}-5-(L-norleucylamino)valeric acid,
2-{[1-(4-methylcyclohexyl)-1H-imidazol-4-yl]methyl}-5-({[(5-methyl-2-oxo-1,3-dioxol-4-yl)methoxy]carbonyl}amino)valeric acid, 5-({[1-(isobutyryloxy)ethoxy]carbonyl}amino)-2-{[1-(4-methylcyclohexyl)-1H-imidazol-4-yl]methyl}valeric acid, 1-[(isopropoxycarbonyl)oxy]ethyl 5-({[1-(isobutyryloxy)ethoxy]carbonyl}amino)-2-{[1-(4-methylcyclohexyl)-1H-imidazol-4-yl]methyl}valerate, 5-({[1-(2,2-dimethylpropanoyloxy)ethoxy]carbonyl}amino)-2-{[1-(4-methylcyclohexyl)-1H-imidazol-4-yl]methyl}valeric acid, 5-[({1-[(cyclohexylcarbonyl)oxy]ethoxy}carbonyl)amino]-2-{[1-(4-methylcyclohexyl)-1H-imidazol-4-yl]methyl}valeric acid, 2-(2-aminoethoxy)-3-[1-(4-methylcyclohexyl)-1H-imidazol-4-yl]propionic acid, 2-[(1R)-2-amino-1-methylethoxy]-3-[1-(4-methylcyclohexyl)-1H-imidazol-4-yl]propionic acid, and 2-(3S)-3-aminopyrrolidin-1-yl]-3-[1-(4-methylcyclohexyl)-1H-imidazol-4-yl]propionic acid.

Hereinafter, typical production processes of the compound of the present invention will be described. However, the present invention is not limited to these processes by any means.

[Production Process 1]

The compound represented by the general formula (I) or a salt thereof, or a solvate thereof can be produced, for example, by the following process:

[Formula 30]

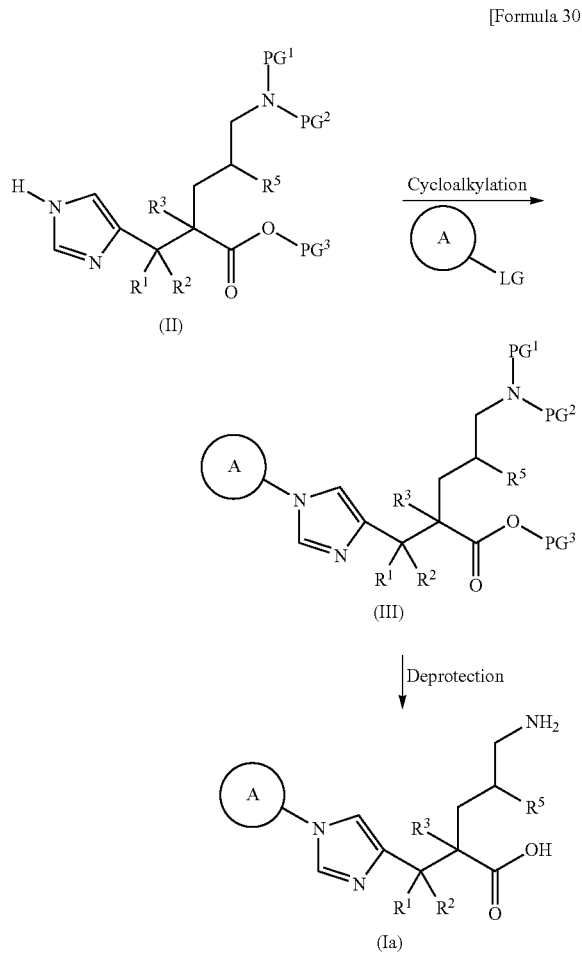

wherein A, $R^1$, $R^2$, $R^3$, and $R^5$ are as defined above; $PG^1$ represents a protective group for the amino group; $PG^2$ represents a hydrogen atom or a protective group for the amino group; $PG^3$ represents a protective group for the carboxy group; and A-LG represents an alkylating agent or alcohol described later.

According to the present production process, a nitrogen atom in the imidazole moiety of a compound (II) is cycloalkylated to produce a compound (III), and protective groups in the compound (III) can further be removed to produce a compound (Ia).

The cycloalkylation reaction is, for example, a reaction through which the compound (III) is formed from the compound (II) and an alkylating agent A-LG (LG represents a leaving group) in the presence of a base. Acyclic, cyclic, or aromatic hydrocarbons or a polar aprotic solvent, for example, tetrahydrofuran, N,N-dimethylformamide, or diethoxyethane, or a mixed solvent thereof can be used as a reaction solvent. For example, cesium carbonate or sodium hydride can be used as a base. An alkyl halide (e.g., A-I or A-Br) or a sulfonic acid ester of an alcohol (e.g., A-$OSO_2CH_3$ or A-$OSO_2CF_3$) can be used as an alkylating agent.

Another method of the cycloalkylation reaction is a method through which the compound (II) and an alcohol A-LG (LG represents a hydroxy group) is condensed by a Mitsunobu reaction to form the compound (III). A method using diethyl azodicarboxylate (DEAD) and triphenylphosphine (Synthesis, 1981, p. 1) is generally known as a Mitsunobu reaction. In this case, a method using (cyanomethylene)tributylphosphorane (CMBP) or (cyanomethylene)trimethylphosphorane (CMMP) is preferable. The production can be achieved with reference to the following documents: 1) Tetrahedron Lett., 1995, Vol. 36, p. 2529; and 2) Tetrahedron Lett., 1996, Vol. 37, p. 2463.

Any protective group usually used as a protective group for amino groups in organic compound synthesis, particularly, peptide synthesis, can be used as a protective group for the amino group. Specific examples thereof can include: alkoxycarbonyl groups such as tert-butoxycarbonyl, methoxycarbonyl, and ethoxycarbonyl groups; arylmethoxycarbonyl groups such as benzyloxycarbonyl, para-methoxybenzyloxycarbonyl and para (or ortho)-nitrobenzyloxycarbonyl groups; arylmethyl groups such as benzyl, 4-methoxybenzyl, and triphenylmethyl groups; alkanoyl groups such as formyl and acetyl groups; aroyl groups such as a benzoyl group; and arylsulfonyl groups such as 2,4-dinitrobenzenesulfonyl and ortho-nitrobenzenesulfonyl groups. These protective groups for the amino group may be selected according to, for example, the properties of the compound whose amino group is to be protected. For removal of the protective groups, reagents or conditions may be selected according to each protective group.

Examples of the protective group for the carboxy group include alkyl, aryl, and arylalkyl ester groups. These protective groups for the carboxy group may be selected according to, for example, the properties of the compound whose carboxy group is to be protected. For removal of the protective groups, reagents or conditions may be selected according to each protective group.

Examples of references on the protection/deprotection of the amino and carboxy groups can include Greene, T. W., Wuts, P. G. M., Protective Groups in Organic Synthesis (1999), 3rd Ed., Wiley-Interscience.

The compound (II) can be produced by well known reactions using a commercially available or known substance. The production can be achieved with reference to, for example, J. Med. Chem., 2007, Vol. 50, p. 6095.

[Production Process 2]

The compound (I) of the present invention can also be produced by the following process:

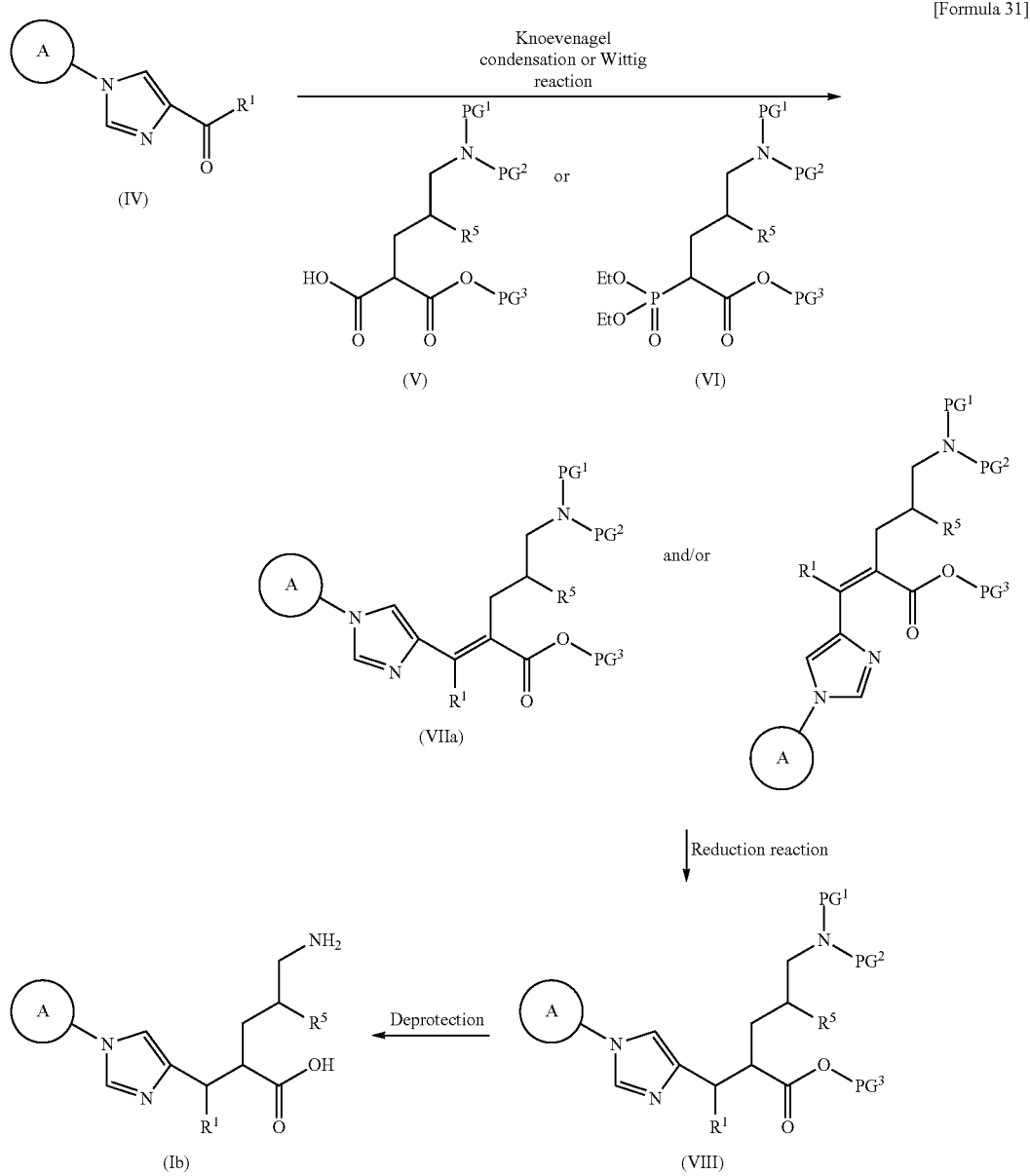

[Formula 31]

wherein A, $R^1$, $R^5$, $PG^1$, $PG^2$ and $PG^3$ are as defined above.

Compounds (VIIa) and/or (VIIb) can be synthesized by a Knoevenagel condensation or a Wittig reaction with a compound (IV) as a starting material. The olefin of the obtained compounds (VIIa) and/or (VIIb) is reduced to synthesize a compound (VIII), and protective groups in the compound (VIII) can be removed to produce a compound (Ib).

The Knoevenagel condensation is, in this case, a reaction through which a compound (V) having active methylene and the compound (IV) having a carbonyl group are condensed in the presence of an amine catalyst to form the compounds (VIIa) and/or (VIIb), which are α,β-unsaturated esters. Decarboxylation occurs by heating to room temperature or 100° C. to form the unsaturated carboxylic acid. Piperidine is generally used as a catalyst. The production can be achieved with reference to the following documents: 1) Org. React. 1967, Vol. 15, p. 204; 2) Comprehensive Organic Synthesis, 1991, Vol. 2, p. 341; and 3) WO200878330.

The Wittig reaction is, in this case, a reaction through which a compound (VI) having a phosphoryl group and the compound (IV) having a carbonyl group are reacted in the presence of a base to form the compounds (VIIa) and/or (VIIb), which are α,β-unsaturated esters. Sodium hydride, sodium methoxide, potassium carbonate, or the like can be used as a base. Alternatively, a base such as 1,8-diazabicyclo [5.4.0]undec-7-ene (DBU) or triethylamine may be used in combination with lithium chloride. Alcohols, tetrahydrofuran, 1,2-dimethoxyethane, dimethyl sulfoxide, acetonitrile, or the like can be used as a solvent. The reaction temperature may be selected as a temperature appropriate for the substrates, and the reaction can be performed at −78° C. to under reflux conditions.

The reduction reaction is, in this case, a reaction through which the compounds (VIIa) and/or (VIIb) are hydrogenated to the compound (VIII) using a heterogenous catalyst. For example, water, methanol, ethanol, ethyl acetate, or acetic acid can be used as a solvent. Palladium-carbon (Pd/C), Pearlman's catalyst (Pd(OH)$_2$), Raney nickel, Adams' catalyst (PtO$_2$), or the like can be used as a catalyst.

The protective groups and their deprotection are as described in Production Process 1.

[Production Process 3]

The compound (I) of the present invention can also be produced by the following process:

zyl, benzyloxymethyl, methoxymethyl, and tert-butoxycarbonyl groups. Examples of references on the protection/deprotection of these protective groups can include Greene, T. W., Wuts, P. G. M., Protective Groups in Organic Synthesis (1999), 3rd Ed., Wiley-Interscience.

The aldol reaction is, in this case, a reaction through which the compound (IX) as a CH-active compound and the compound (IV) having a carbonyl group are bonded to each other in the presence of a strong base to obtain a β-hydroxycarbonyl compound. For example, a carbonate of an alkali metal or alkaline-earth metal (e.g., sodium carbonate or potassium carbonate), an alkali metal alkoxide (e.g., sodium ethoxide or potassium butoxide), an alkali metal hydroxide (e.g., sodium hydroxide or potassium hydroxide), an alkali metal hydride (e.g., sodium hydride or potassium hydride), or an organic

[Formula 32]

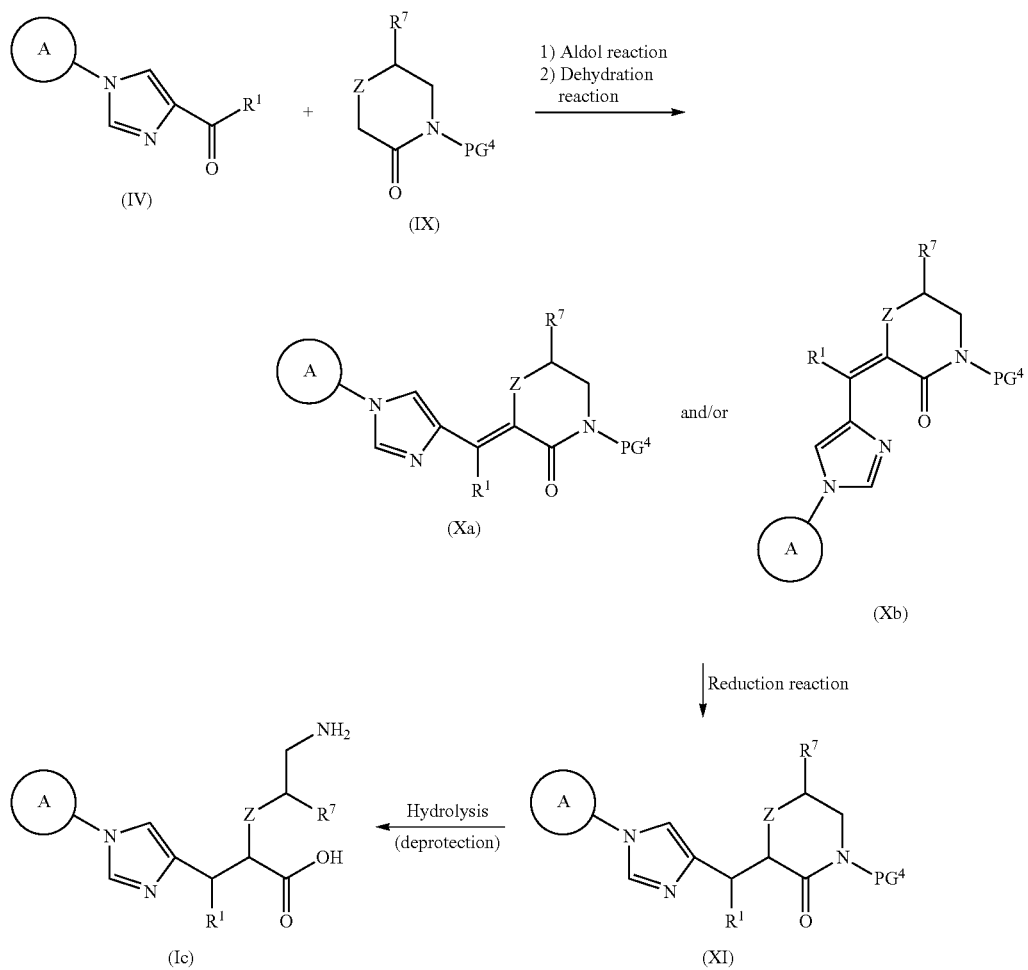

wherein A, R$^1$, and R$^7$ are as defined above; PG$^4$ represents a hydrogen atom or a protective group for the amide group; and Z represents an oxygen atom or a methylene group.

The compound (IV) and a compound (IX) can be subjected to an aldol reaction and a dehydration reaction to produce compounds (Xa) and/or (Xb). The olefin of the obtained compounds (Xa) and/or (Xb) is reduced to synthesize a compound (XI), which can then be hydrolyzed to produce a compound (Ic).

Examples of the protective group for the amide group in the compound (IX) include allyl, tert-butyl, para-methoxybenmetal base such as alkyllithium (e.g., n-butyllithium), dialkylaminolithium (e.g., lithium diisopropylamide), or bissilylamine (e.g., lithium hexamethyldisilazide) can be used as a strong base. Acyclic, cyclic, or aromatic hydrocarbons, alcohols, or a polar aprotic solvent, for example, tetrahydrofuran, N,N-dimethylformamide, or diethoxyethane, or a mixed solvent thereof can be used as a reaction solvent. The reaction temperature can be approximately −78° C. to room temperature.

The dehydration reaction is a reaction through which a hydroxy group in the β-hydroxycarbonyl compound obtained by the aldol reaction is treated with methanesulfonyl chloride or benzenesulfonyl chloride or the like at −78° C. to 50° C. in the presence of triethylamine in an inert solvent and then further treated with a base to form a compound (X). Examples of the inert solvent include: alkyl halide solvents such as dichloromethane, chloroform, and carbon tetrachloride; ether solvents such as tetrahydrofuran, 1,2-dimethoxyethane, and dioxane; aromatic solvents such as benzene and toluene; and amide solvents such as N,N-dimethylformamide, N,N-dimethylacetamide, and N-methylpyrrolidin-2-one. In addition to these, sulfoxide solvents such as dimethyl sulfoxide and sulfolane, ketone solvents such as acetone and methyl ethyl ketone, or acetonitrile, or the like may be used in some cases. The base is preferably an organic base such as pyridine, 2,6-lutidine, collidine, 4-dimethylaminopyridine, triethylamine, N-methylmorpholine, diisopropylethylamine, or 1,8-diazabicyclo[5.4.0]undec-7-ene (DBU). The dehydration reaction may proceed under the aldol reaction conditions in some cases.

include heating to reflux using concentrated hydrochloric acid. See the following reference: J. Org. Chem., 1996, Vol. 61, p. 4990.

When $PG^4$ is a protective group for the amide group that may be deprotected under acidic conditions, the deprotection reaction can also be achieved under the conditions shown above. When it is a protective group that cannot be deprotected under acidic conditions, reagents or conditions may be selected according to the protective group. Examples of references thereon can include Greene, T. W., Wuts, P. G. M., Protective Groups in Organic Synthesis (1999), 3rd Ed., Wiley-Interscience.

The compound (IX) can be produced by well known reactions using a commercially available or known substance. The production can be achieved with reference to, for example, Org. Lett, 2009, Vol. 11, p. 5410.

[Production Process 4]

The compound (I) of the present invention can also be produced by the following process:

[Formula 33]

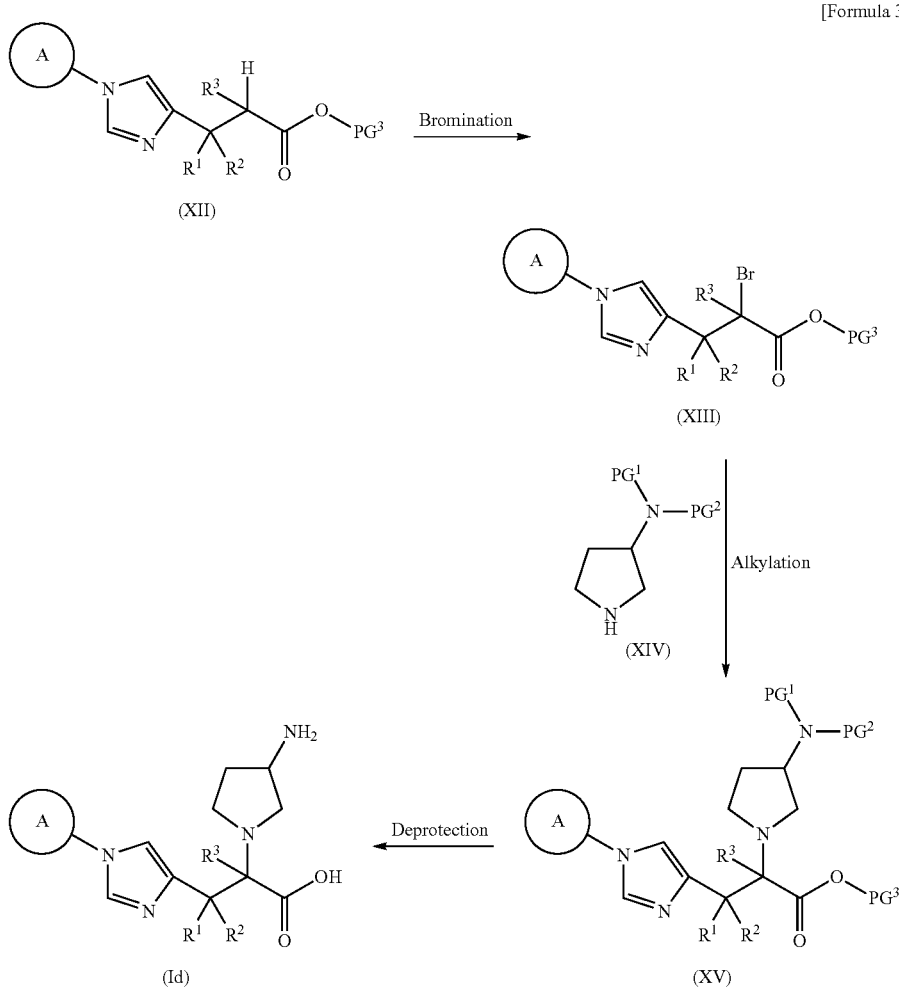

wherein A, $R^1$, $R^2$, $R^3$, $PG^1$, $PG^2$ and $PG^3$ are as defined above.

The reduction reaction can be performed according to the method described in Production Process 2.

The hydrolysis is a reaction through which the lactam ring of the compound (XI) is acid-hydrolyzed to obtain the compound (Ic). Examples of the specific reaction conditions A compound (XII) is brominated to synthesize a compound (XIII), and a compound (XIV) can be alkylated with the compound (XIII) as an alkylating agent to synthesize a compound (XV). Protective groups in the obtained compound (XV) can be removed to produce a compound (Id).

The bromination reaction is a reaction through which the α-position of a carbonyl group in the compound (XII) is selectively brominated to obtain the compound (XIII). For this purpose, the compound (XII) can be temporarily converted to silyl enol ether and then treated with bromine or N-bromosuccinimide (NBS) to obtain the compound of interest. The production can be achieved with reference to the following document: Tetrahedron Asymmetry, 1995, Vol. 6, p. 2291.

The alkylation reaction is a reaction through which the compound (XV) is formed from the compound (XIV) and the compound (XIII) as an alkylating agent, for example, in the presence of a base. Acyclic, cyclic, or aromatic hydrocarbons or a polar aprotic solvent, for example, tetrahydrofuran, N,N-dimethylformamide, or diethoxyethane, or a mixed solvent thereof can be used as a reaction solvent. For example, an organic base such as pyridine, 2,6-lutidine, collidine, 4-dimethylaminopyridine, triethylamine, N-methylmorpholine, diisopropylethylamine, or 1,8-diazabicyclo[5.4.0]undec-7-ene (DBU) can be used as a base.

The protective groups and their deprotection are as described in Production Process 1.

The compound (XIV) can be produced by well known reactions using a commercially available or known substance.

[Production Process 5]

The compound (IV), an intermediate of the compound of the present invention, can be produced, for example, by the following process:

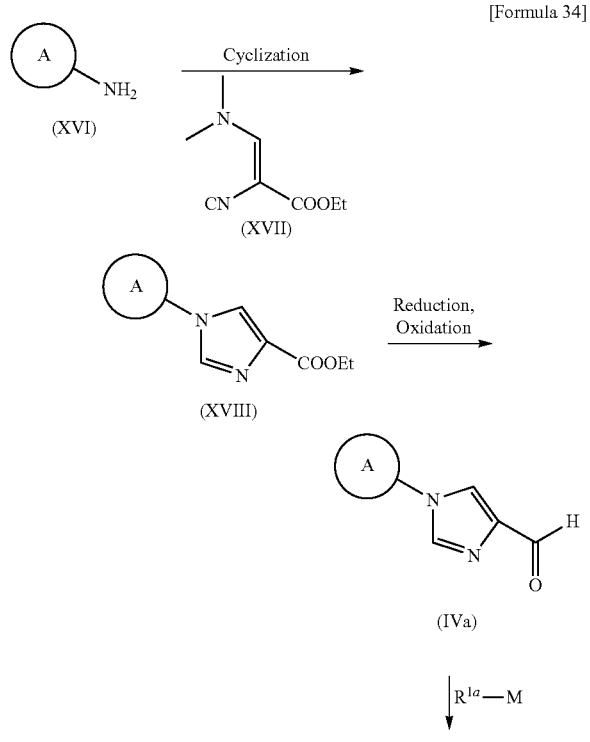

[Formula 34]

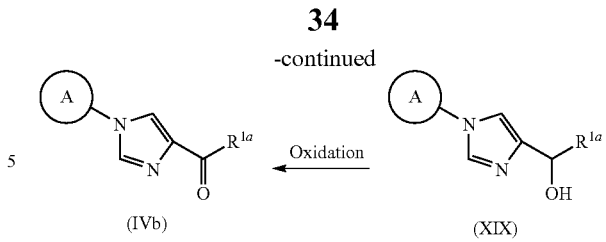

wherein A is as defined above; $R^{1a}$ represents a C1 to C6 alkyl group; and M represents Li or MgBr or the like.

A compound (XVI) that is commercially available or is synthesized using a well known method can be reacted with a compound (XVII) (Liebigs Annalen der Chemie, 1979, p. 1444) for construction of an imidazole ring to synthesize a compound (XVIII). The production can be achieved with reference to the following document: Org. Lett. 2002, Vol. 4, p. 4133.

The obtained compound (XVIII) is reduced into a primary alcohol by reduction using metal hydride in an inert solvent, and the primary alcohol can then be oxidized into an aldehyde to produce a compound (IVa). Examples of the metal hydride include lithium aluminum hydride, lithium borohydride, sodium bis(2-methoxyethoxy)aluminum hydride, and sodium borohydride. An oxidation method known in the art, i.e., PCC oxidation, PDC oxidation, Swern oxidation, TPAP oxidation, Dess-Martin oxidation, TEMPO oxidation, Mukaiyama oxidation, or the like can be used as an oxidation method. Among them, TEMPO oxidation is preferable. The production can be achieved with reference to the following document: Org. Lett. 2003, Vol. 5, p. 285.

Alternatively, the compound (XVIII) can also be converted directly to the compound (IVa) by performing the reaction at a low temperature using an appropriate metal hydride. In this case, examples of the metal hydride include diisobutylaluminum hydride.

The obtained compound (IVa) can be treated with an organic lithium or organic magnesium compound $R^{1a}$-M to obtain a compound (XIX). Examples of the organic lithium compound or the organic magnesium compound can include: an alkyllithium such as methyllithium, ethyllithium, normal propyllithium, normal butyllithium, isobutyllithium, sec-butyllithium, tert-butyllithium, normal pentyllithium, isopentyllithium, and neopentyllithium; and an alkyl magnesium such as methyl magnesium bromide, ethyl magnesium bromide, propyl magnesium bromide, isopropyl magnesium bromide, normal butyl magnesium bromide, isobutyl magnesium bromide, sec-butyl magnesium bromide, tert-butyl magnesium bromide, and methyl magnesium iodide. Aromatic hydrocarbons (e.g., toluene or benzene), linear or cyclic aliphatic hydrocarbons (e.g., propane, butane, pentane, hexane, heptane, or cyclohexane), or an ether solvent (e.g., diethyl ether or tetrahydrofuran), or the like can be used as a reaction solvent. The reaction temperature is preferably −78° C. to room temperature. From the obtained compound (XIX), a compound (IVb) can be produced by an oxidation method known in the art. PCC oxidation, PDC oxidation, Swern oxidation, TPAP oxidation, or the like may be used as an oxidation method. For example, carbonyl can be synthesized from alcohol through an oxidation reaction based on TPAP oxidation with reference to Synthesis, 1994, p. 639.

[Production Process 6]

Of the compounds (I) of the present invention, a compound containing a prodrug group introduced therein can be produced by the following process:

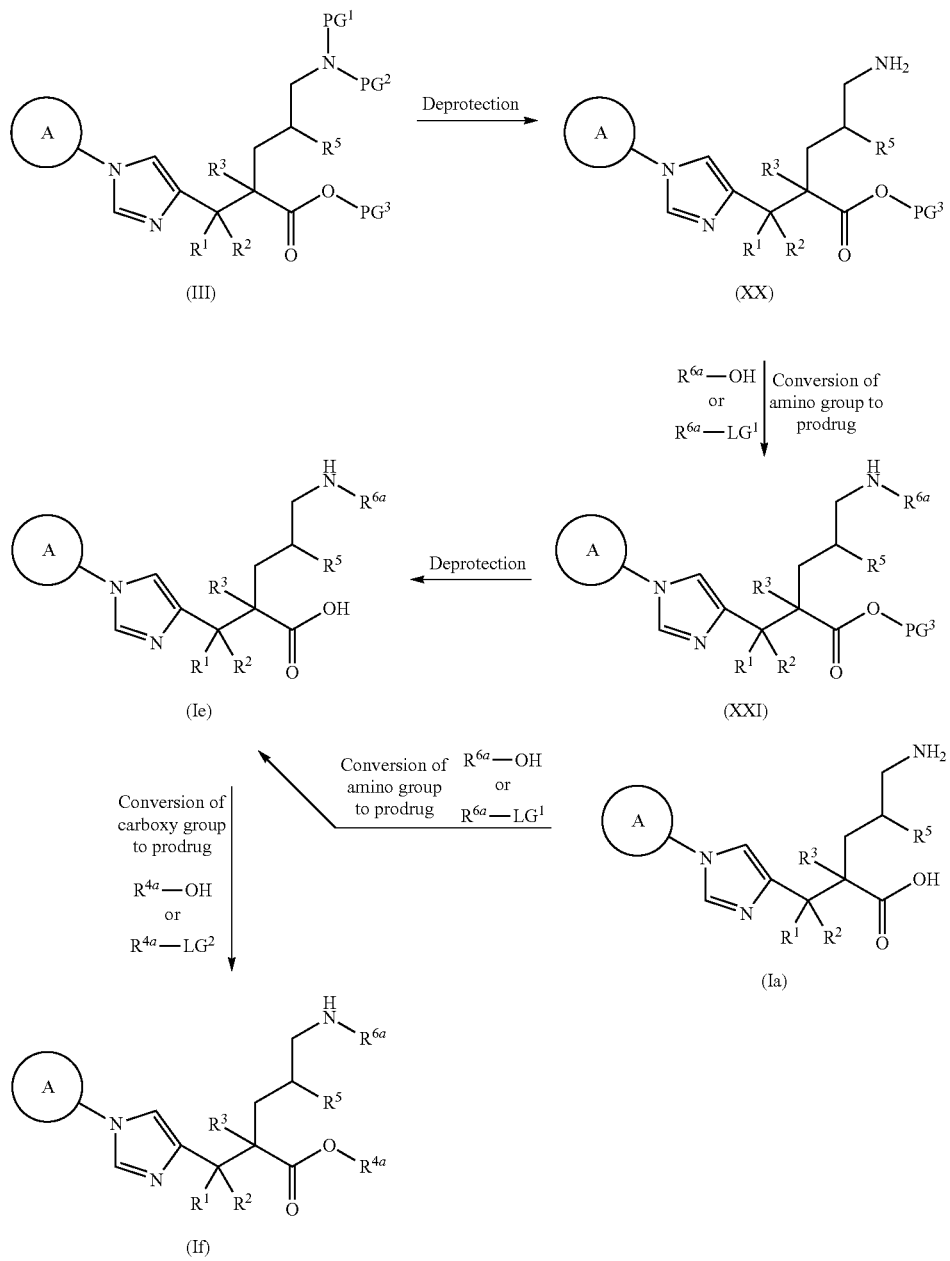

wherein A, $R^1$, $R^2$, $R^3$, $R^5$, $PG^1$, $PG^2$, and $PG^3$ are as defined above; $R^{4a}$ and $R^{6a}$ represent prodrug groups; and $LG^1$ and $LG^2$ represent leaving groups.

The protective group for the amino group in the compound (III) obtained by Production Process 1 can be removed to obtain a compound (XX). The amino group of the compound (XX) is converted to a prodrug to synthesize a compound (XXI), and the protective group for the carboxy group in the compound (XXI) can be removed to produce a compound (Ie) in a prodrug form.

Moreover, the compound (Ie) may be produced directly by converting the compound (Ia) to a prodrug.

The carboxy group of the obtained compound (Ie) can further be converted to a prodrug to produce a compound (If).

For the protective groups and their deprotection, protective groups as described in Production Process 1 may be selected, and reagents or conditions appropriate for each protective group may be selected for the cleavage (deprotection) of the protective groups.

The conversion of the amino group to a prodrug is a reaction through which the compound (XXI) is obtained by a condensation reaction of the compound (XX) and a compound $R^{6a}$—OH. Any condensation reaction used in usual peptide synthesis can be used. Examples of a condensing agent include N,N'-dicyclohexylcarbodiimide (DCC), 1-ethyl-3-(3-dimethylaminopropyl)carbodiimide hydrochloride (EDC-HCl), 4-(4,6-dimethoxy-1,3,5-triazin-2-yl)-4-methylmorpholinium chloride hydrate (DMT-MM), (1H-benzotriazol-1-yloxy)tris(dimethylamino)phosphonium hexafluorophosphate (BOP), and 1-[bis(dimethylamino)methylene]-1H-benzotriazolium-3-oxide hexafluorophosphate (HBTU). The production can be achieved with reference to, for example, Tetrahedron, 2004, Vol. 60, p. 2447.

In another method of the conversion of the amino group to a prodrug, the compound (XX) and an active ester compound $R^{6a}$-$LG^1$ may be condensed to obtain the compound (XXI). Examples of $LG^1$ include p-nitrophenyloxy, pentafluorophenyloxy, and chloro groups. A method for the condensation reaction of an amine and an active ester used in usual peptide synthesis can be used.

example, a carbonate of an alkali metal or alkaline-earth metal such as sodium carbonate, sodium bicarbonate, potassium carbonate, or potassium bicarbonate can be used as a base.

[Production Process 7]

Of the compounds (I) of the present invention, a compound containing a prodrug group introduced therein can be produced by the following method:

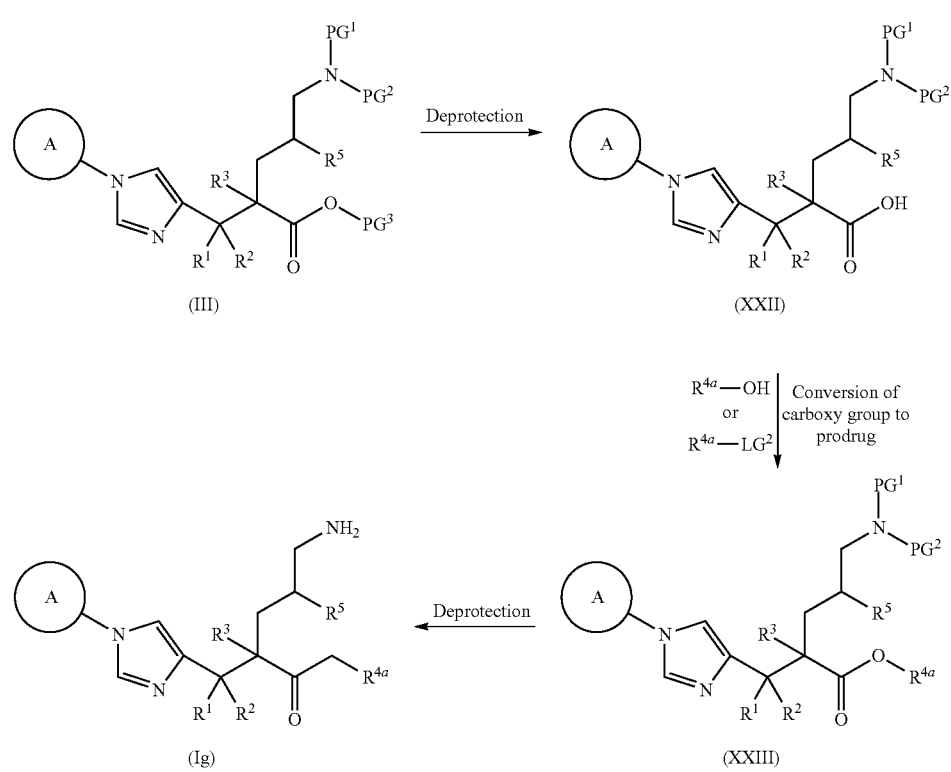

[Formula 36]

The compound (Ia) can also be condensed with $R^{6a}$—OH or $R^{6a}$-$LG^1$ in the same way as in the method above to directly produce the compound (Ie).

The conversion of the carboxy group to a prodrug is a reaction through which the compound (Ie) and an alcohol compound $R^4$—OH are condensed to obtain the compound (If). N,N'-dicyclohexylcarbodiimide (DCC), N,N'-diisopropylcarbodiimide (DIC), or the like can be used as a condensing agent. The reactivity is improved by adding in advance a catalytic amount of 4-dimethylaminopyridine (DMAP) to the system.

In another method of the conversion of the carboxy group to a prodrug, the compound (Ie) and a compound $R^{4a}$-$LG^2$, which is an alkylating agent, can be reacted under basic conditions to obtain the compound (If). In this case, examples of $LG^2$ include iodo and bromo groups. Alternatively, a sulfonic acid ester of an alcohol (e.g., $R^{4a}$—$OSO_2CH_3$ or $R^{4a}$—$OSO_2CF_3$) may be used as $R^{4a}$-$LG^2$. Water, tetrahydrofuran, N,N-dimethylformamide, or diethoxyethane, or the like, or a mixed solvent thereof can be used as a reaction solvent. For wherein A, $R^1$, $R^2$, $R^3$, $R^{4a}$, $R^5$, $PG^1$, $PG^2$, $PG^3$ and $LG^2$ are as defined above.

The protective group of the carboxy group in the compound (III) obtained in Production Process 1 can be removed to produce a compound (XXII). Subsequently, a prodrug group is introduced to the carboxy group of the compound (XXII), and the protective group of its amino group can be removed to produce a compound (Ig) in a prodrug form.

For the protective groups and their deprotection, protective groups as described in Production Process 1 may be selected, and reagents or conditions appropriate for each protective group may be selected for the cleavage (deprotection) of the protective groups.

The conversion of the carboxy group to a prodrug can be performed with reference to the method described in Production Process 6.

[Production Process 8]

Of the compounds (I) of the present invention, a compound containing a prodrug group introduced therein can be produced by the following method:

[Formula 37]
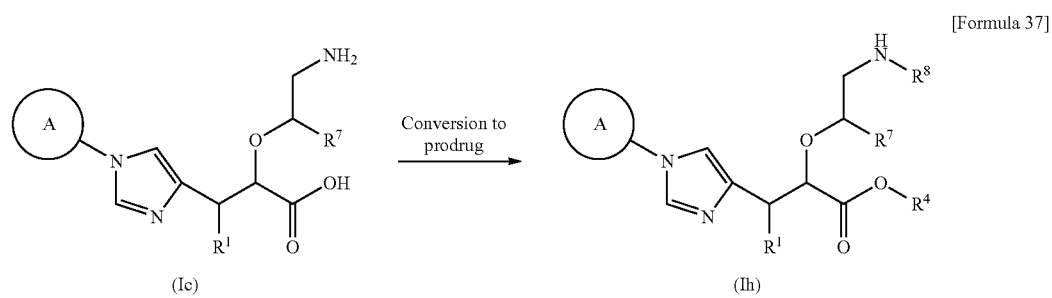
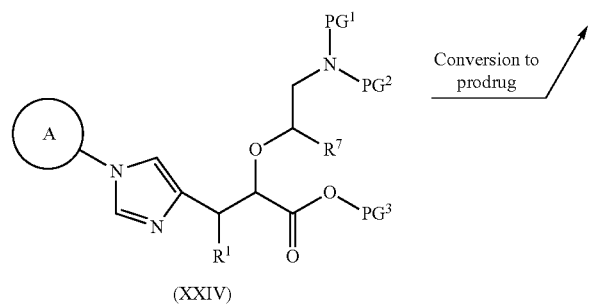
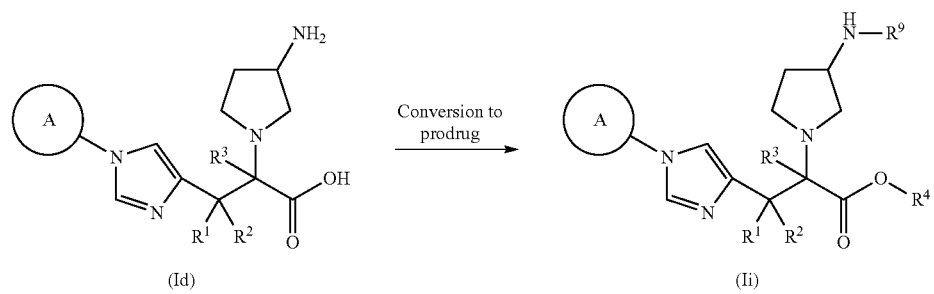
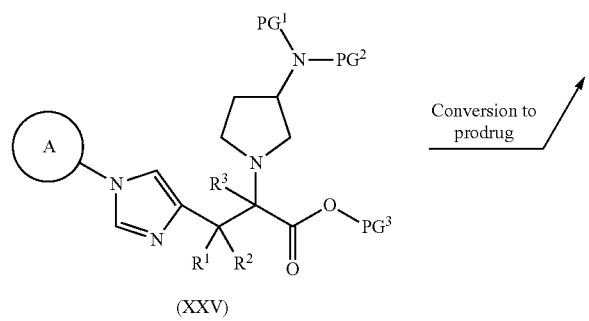

wherein A, $R^1$, $R^2$, $R^3$, $R^4$, $R^7$, $R^8$, $R^9$, $PG^1$, $PG^2$ and $PG^3$ are as defined above, provided that $R^4$ and $R^8$ are not a hydrogen atom simultaneously.

A compound (Ih) or (Ii) in a prodrug form can be produced from compounds (Ic), (XXIV), (Id), and (XXV) in the same way as in Production Process 6 or 7.

The compound (XXIV) and the compound (XXV) can be produced by introducing a protective group to the synthetic intermediate compounds or final products exemplified in Production Processes 3 and 4.

[Production Process 9]

[Formula 38]

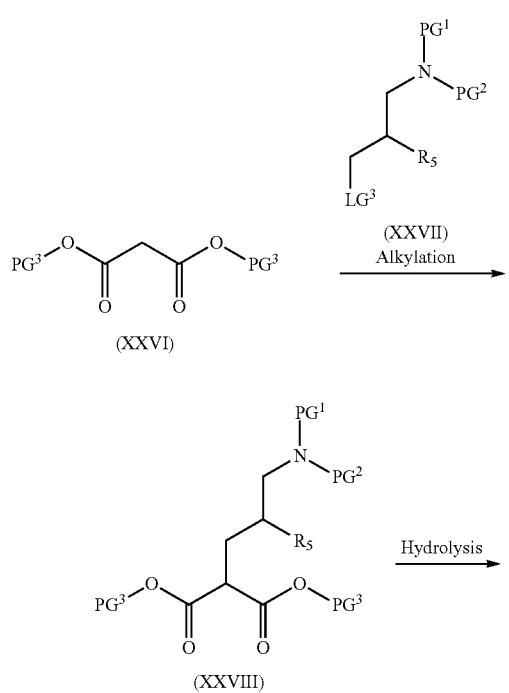

(XXVI)

(XXVII) Alkylation (XXVIII)

Hydrolysis

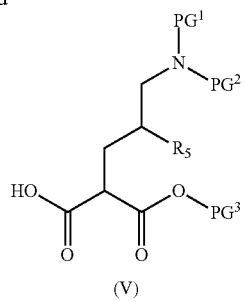

(V)

wherein $R^5$, $PG^1$, $PG^2$, and $PG^3$ are as defined above; and $LG^3$ represents a leaving group.

The alkylation reaction is a reaction through which malonic acid diester (XXVI) is alkylated in the presence of a base using a compound (XXVII) that is commercially available or can be produced by well known reactions. For example, an alkali metal hydroxide, an alkali metal hydride, a carbonate of an alkali metal or alkaline-earth metal, or an alkali metal alkoxide (e.g., sodium carbonate, potassium carbonate, sodium ethoxide, potassium butoxide, sodium hydroxide, potassium hydroxide, sodium hydride, or potassium hydride), or an organic metal base such as alkyllithium (e.g., n-butyllithium), dialkylaminolithium (e.g., lithium diisopropylamide), or an alkali metal base of bissilylamine (e.g., lithium hexamethyldisilazide) can be used as a base. Furthermore, examples of $LG^3$ can include: halogen atoms such as chlorine, bromine, and iodine; and alkylsulfonyloxy or arylsulfonyloxy groups such as mesylate, tosylate, and triflate.

The hydrolysis is a reaction through which the compound (XXVIII) is hydrolyzed in the presence of a base to produce the compound (V). Examples of the base can include an alkali metal hydroxide such as lithium hydroxide, sodium hydroxide, and potassium hydroxide. A protic solvent (e.g., methanol, ethanol, or water), an aprotic ether solvent (e.g., tetrahydrofuran, dioxane, or 1,2-dimethoxyethane), or a mixed solvent of two or more thereof combined at any ratio can be used as a reaction solvent.

The compound (VI) can be produced by well known reactions using a commercially available or known substance. The production can be achieved with reference to, for example, J. Med. Chem., 2007, Vol. 50, p. 6095.

[Production Process 10]

[Formula 39]

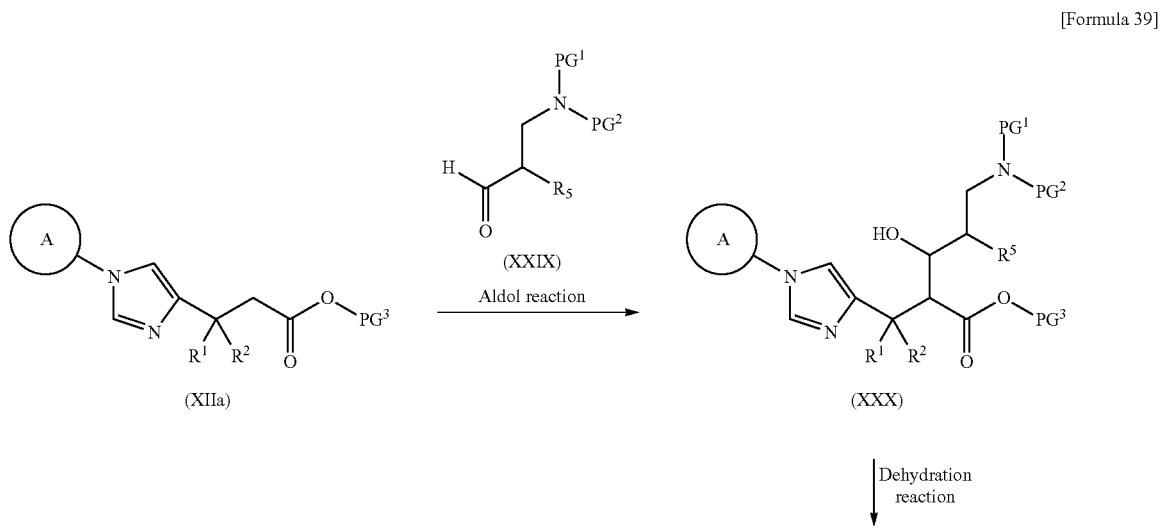

(XIIa)

(XXIX) Aldol reaction (XXX)

Dehydration reaction

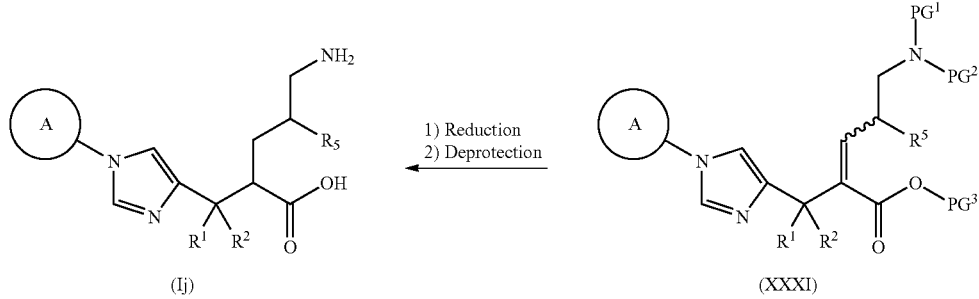

wherein A, $R^1$, $R^2$, $R^5$, $PG^1$, $PG^2$, and $PG^3$ are as defined above.

A compound (XIIa) and a compound (XXIX) are subjected to an aldol reaction to produce a compound (XXX), and the obtained compound (XXX) can be subjected to dehydration reaction to produce a compound (XXXI). Subsequently, the olefin moiety is reduced, and the protective group can be removed to produce a compound (Ij).

The aldol reaction is, in this case, a reaction through which the compound (XIIa) as a CH-active compound and the compound (XXIX) containing a carbonyl group are bonded to each other in the presence of a strong base to form a compound (XXX). For example, a carbonate of an alkali metal or alkaline-earth metal (e.g., sodium carbonate or potassium carbonate), an alkali metal alkoxide (e.g., sodium ethoxide or potassium butoxide), an alkali metal hydroxide (e.g., sodium hydroxide or potassium hydroxide), an alkali metal hydride (e.g., sodium hydride or potassium hydride), or an organic metal base such as alkyllithium (e.g., n-butyllithium), dialkylaminolithium (e.g., lithium diisopropylamide), or bissilylamine (e.g., lithium hexamethyldisilazide) can be used as a strong base. Acyclic, cyclic, or aromatic hydrocarbons, alcohols, or a polar aprotic solvent, for example, tetrahydrofuran, N,N-dimethylformamide, or diethoxyethane, or a mixed solvent thereof can be used as a reaction solvent. The reaction temperature is approximately −78° C. to room temperature.

The dehydration reaction is a reaction through which a hydroxy group in the compound (XXX) is converted to sulfonic acid ester by treatment with methanesulfonyl chloride or benzenesulfonyl chloride or the like at −78° C. to 50° C. in the presence of triethylamine in an inert solvent and then further treated with a base to form a compound (XXXI). Examples of the inert solvent include: alkyl halide solvents such as methylene chloride, chloroform, and carbon tetrachloride; ether solvents such as tetrahydrofuran, 1,2-dimethoxyethane, and dioxane; aromatic solvents such as benzene and toluene; and amide solvents such as N,N-dimethylformamide, N,N-dimethylacetamide, and N-methylpyrrolidin-2-one. In addition to these, sulfoxide solvents such as dimethyl sulfoxide and sulfolane, ketone solvents such as acetone and methyl ethyl ketone, or acetonitrile, or the like may be used in some cases. Pyridine, 2,6-lutidine, collidine, 4-dimethylaminopyridine, triethylamine, N-methylmorpholine, diisopropylethylamine, or 1,8-diazabicyclo[5.4.0]undec-7-ene (DBU) can be used as a base. In some cases, the dehydration reaction may proceed during the aldol reaction.

The reduction reaction can be performed according to the method described in Production Process 2. The protective groups and their deprotection can be performed according to the method described in Production Process 1. The compound (Ij) can be produced from the compound (XXXI) using these reactions.

When the compounds of interest or intermediates in these production processes 1 to 10 are isomeric (e.g., stereoisomeric) mixtures, each isomer can be separated and purified appropriately by preparative medium-pressure chromatography, HPLC, or the like using an optically active column or the like.

When the compound of the present invention represented by the general formula (I) or a pharmacologically acceptable salt thereof, or a production intermediate thereof has asymmetric carbon, their optical isomers are present. From these optical isomers, each isomer can be separated and purified by a conventional method such as fractional crystallization (salt resolution) using recrystallization with an appropriate solvent or column chromatography. Examples of references on a method of resolving racemic mixtures into optical isomers can include J. Jacques et al., "Enantiomers, Racemates and Resolution, John Wiley And Sons, Inc."

The cycloalkyl-substituted imidazole derivative of the present invention has excellent TAFIa inhibitory activity and has good oral absorbability, excellent disposition such as retention in blood and metabolic stability, and high safety. Therefore, the cycloalkyl-substituted imidazole derivative of the present invention is useful as a pharmaceutical drug and particularly useful as a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, pulmonary fibrosis, or the like. Moreover, it is useful as a therapeutic drug for a thromboembolism-derived disease. Furthermore, it is useful as a pharmaceutical drug for improving the functions of an organ after transplantation. The compound of the present invention is also useful as a therapeutic drug for coronary arterial diseases after surgery (percutaneous transluminal coronary angioplasty), transplantation or replacement of a vascular substitute (autologous or artificial blood vessel), or restenosis/reocclusion caused by stent implantation. Moreover, it is useful for the prevention of thrombus formation caused by a vascular catheter (indwelling catheter for dialysis), an extracorporeal blood circulator, and the coating of an artificial blood vessel or the filling thereof with a TAFIa inhibitor solution, and for the promotion of thrombolysis. It is also useful as a therapeutic drug for atherothrombosis or fibrosis (lung fibrosis such as chronic obstructive pulmonary disease, fibrosis after ophthalmic surgery, etc.).

The compound of the present invention represented by the general formula (I) has a basic group such as an amino group and can therefore be made into an acid-addition salt with a pharmacologically acceptable acid. Examples of such a salt can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornitate, glutamate, and aspartate. Hydrohalides or arylsulfonates are preferable; hydrochloride, benzenesulfonate or p-toluenesulfonate is more preferable; benzenesulfonate or p-toluenesulfonate is even more preferable; and p-toluenesulfonate is particularly preferable.

Moreover, the compound represented by the general formula (I) has an acidic group such as a carboxy group and can therefore form a base-addition salt, in general. Examples of the pharmacologically acceptable salt can include: alkali metal salts such as sodium salts, potassium salts, and lithium salts; alkaline-earth metal salts such as calcium salts and magnesium salts; inorganic salts such as ammonium salts; organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts; and amino acid salts such as arginine salts.

The compound of the present invention represented by the general formula (I) or the pharmacologically acceptable salt thereof may be present in a free or solvate form. These solvates are also encompassed in the scope of the present invention. The solvate is not particularly limited as long as it is pharmacologically acceptable. Specifically, hydrates, ethanolates, or the like are preferable; and hydrates are more preferable. Moreover, the compound of the present invention represented by the general formula (I) contains a nitrogen atom. This nitrogen atom may be in an N-oxide form. These solvate or N-oxide forms are also encompassed in the scope of the present invention.

The compound of the present invention represented by the general formula (I) or the pharmacologically acceptable salt thereof, and the production intermediate of the compound of the present invention can include various isomers such as geometric isomers (e.g., cis and trans forms) and optical isomers (R and S forms), depending on the kinds or combinations of substituents. The compound of the present invention encompasses all of these isomers, stereoisomers, and even mixtures of these isomers and stereoisomers in any ratio, unless otherwise specified.

Moreover, the compound of the present invention or the pharmacologically acceptable salt thereof can also contain non-natural ratios of atomic isotopes of one or more of the atoms constituting such a compound. Examples of the atomic isotopes include deuterium ($^2H$), tritium ($^3H$), carbon-13 ($^{13}C$), carbon-14 ($^{14}C$) nitrogen-15 ($^{15}N$), chlorine-37 ($^{37}Cl$), and iodine-125 ($^{125}I$). Moreover, the compound may be labeled radioactively with a radioisotope, for example, tritium ($^3H$), iodine-125 ($^{125}I$), or carbon-14 ($^{14}C$). The radioactively labeled compound is useful as a therapeutic or preventive agent, a research reagent, for example, an assay reagent, and a diagnostic agent, for example, an in-vivo diagnostic imaging agent. All the isotopic variants of the compound of the present invention are encompassed in the scope of the present invention, regardless of being radioactive or not.

Furthermore, the present invention also encompasses a "pharmaceutically acceptable prodrug compound" that is converted through reaction with an enzyme, gastric acid, or the like under physiological conditions in vivo to the compound (I) serving as an active ingredient of a pharmaceutical composition of the present invention, i.e., a compound that is converted to the compound (I) through enzymatic oxidation, reduction, hydrolysis, or the like, or a compound that is converted to the compound (I) through hydrolysis or the like caused by gastric acid or the like.

The compound of the general formula (I) of the present invention or the pharmacologically acceptable salt thereof may form a plurality of crystals (crystal polymorphs) differing in internal structure and physiochemical properties depending on reaction conditions and crystallization conditions. Each of these crystals or a mixture thereof at any ratio is encompassed in the present invention. Also, the compound of the general formula (I) or the pharmacologically acceptable salt thereof may be present as a mixture of crystalline solids and amorphous solids. A mixture thereof at any ratio is encompassed in the present invention. Specifically, the content of a particular crystal form of the present invention is preferably 50% or more, more preferably 80% or more, even more preferably 90% or more, particularly preferably 95% or more, most preferably 97% or more.

In the present invention, the crystals refer to a solid having three-dimensional regular repeats of atoms (or populations thereof) constituting the internal structure and are discriminated from amorphous solids, which do not have such a regular internal structure. Whether a certain solid is crystalline or not can be examined by a well known crystallographic method (e.g., powder X-ray crystallography or differential scanning calorimetry). For example, the certain solid is subjected to powder X-ray crystallography using X-rays obtained by copper Kα radiation. The solid is determined to be crystalline when a distinctive peak is observed in its X-ray diffraction pattern, or determined to be amorphous when a distinctive peak is not observed therein. When the peak can be read, but is not distinctive (e.g., the peak is broad), the solid is determined to be crystals having a low degree of crystallinity. Such crystals having a low degree of crystallinity are encompassed in the crystals of the present invention.

In powder crystallography using copper Kα rays, a sample is usually irradiated with copper Kα rays (in which Kα1 and Kα2 rays are not separated). The X-ray diffraction pattern can be obtained by analyzing diffraction derived from the Kα rays, and can also be obtained by analyzing only diffraction derived from Kα1 rays collected from the diffraction derived from the Kα rays. In the present invention, the powder X-ray diffraction pattern obtained by Kα radiation encompasses an X-ray diffraction pattern obtained by analyzing diffraction derived from Kα rays, and an X-ray diffraction pattern obtained by analyzing diffraction derived from Kα1 rays and is preferably an X-ray diffraction pattern obtained by analyzing diffraction derived from Kα1 rays.

Type I crystals of (2S)-5-amino-2-{[1-(trans-4-methylcyclohexyl)-1H-imidazol-4-yl]methyl}valeric acid p-toluenesulfonate anhydrate of the present invention can be crystals exhibiting main peaks at interplanar spacings d of 23.9, 11.9, 4.5, 4.3, and 3.6 angstroms in a powder X-ray diffraction pattern obtained by copper Kα radiation, for example, as shown in FIG. 1.

Figure 3:
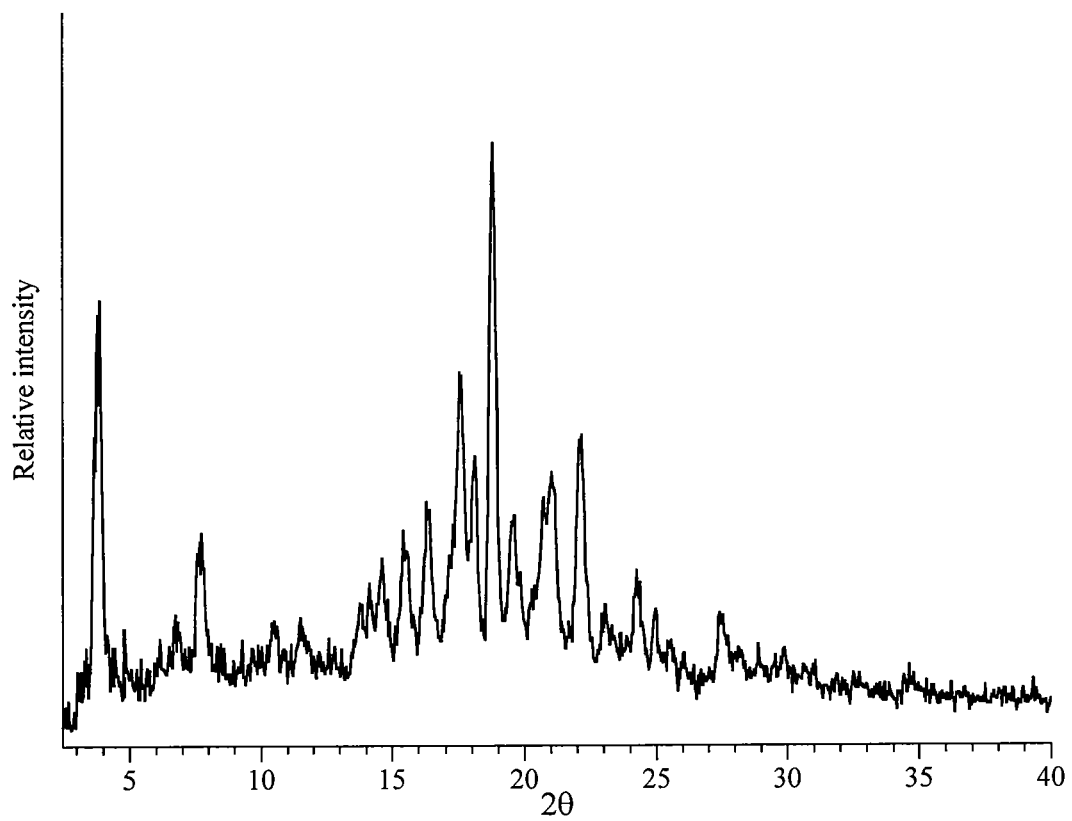
FIG. 3 shows the results of irradiating type II crystals of (2S)-5-amino-2-{[1-(trans-4-methylcyclohexyl)-1H-imidazol-4-yl]methyl}valeric acid p-toluenesulfonate monohydrate with Cu Kα X-rays of 1.54 angstroms in a Bruker transmission-type HT-compatible powder X-ray diffractometer equipped with a two-dimensional detector, D8 DISCOVER with GADDS CST, and measuring powder X-ray diffraction data using a Mylar film. In this powder X-ray diffraction pattern, the ordinate represents diffraction intensity indicated in count/second (cps) units, and the abscissa represents diffraction angles indicated in 2θ values. Peak position is within the range of 2θ±0.2°.

Type II crystals of (2S)-5-amino-2-{[1-(trans-4-methylcyclohexyl)-1H-imidazol-4-yl]methyl}valeric acid p-toluenesulfonate monohydrate of the present invention can be crystals exhibiting main peaks at interplanar spacings d of 22.9, 5.0, 4.9, 4.7, and 4.0 angstroms in a powder X-ray diffraction pattern obtained by copper Kα radiation, for example, as shown in FIG. 3.

In the powder X-ray diffraction pattern of FIG. 1 or 3 below, the ordinate represents diffraction intensity [count/second (cps)], and the abscissa represents diffraction angles 2θ (degrees). Moreover, the interplanar spacings d (angstroms) can be calculated according to the formula 2d sin θ=nλ wherein n=1. In this formula, the wavelength λ of the Kα rays is 1.54 angstroms, and the wavelength λ of the Kα t rays is 1.541 angstroms. The positions and relative intensities of peaks at the interplanar spacings d can somewhat vary depending on measurement conditions, etc. Thus, the identity of a crystal form should be recognized appropriately with reference to the whole pattern of a spectrum, even when interplanar spacings d slightly differ from the expected ones.

Figure 2:
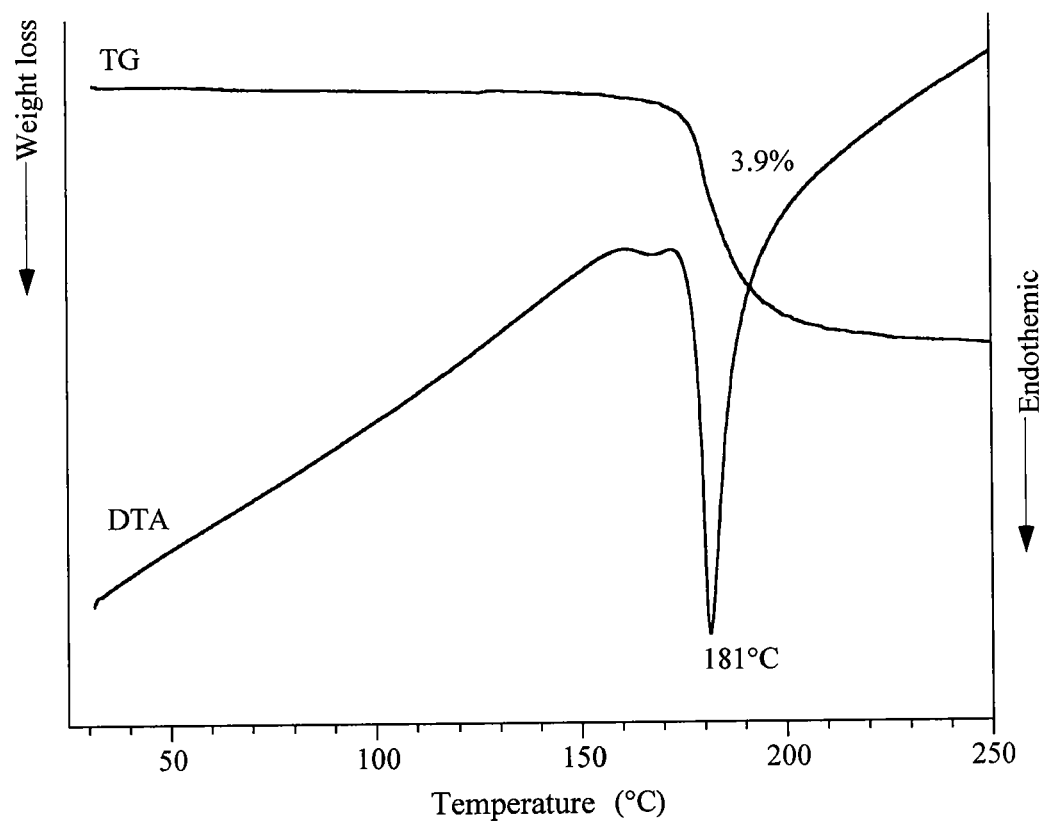
FIG. 2 shows the results of thermally analyzing type I crystals of (2S)-5-amino-2-{[1-(trans-4-methylcyclohexyl)-1H-imidazol-4-yl]methyl}valeric acid p-toluenesulfonate anhydrate. In this thermal analysis (TG/DTA), measurement was performed at a heating rate of 10° C./min. under a stream of 200 mL/min. dry nitrogen.
Figure 4:
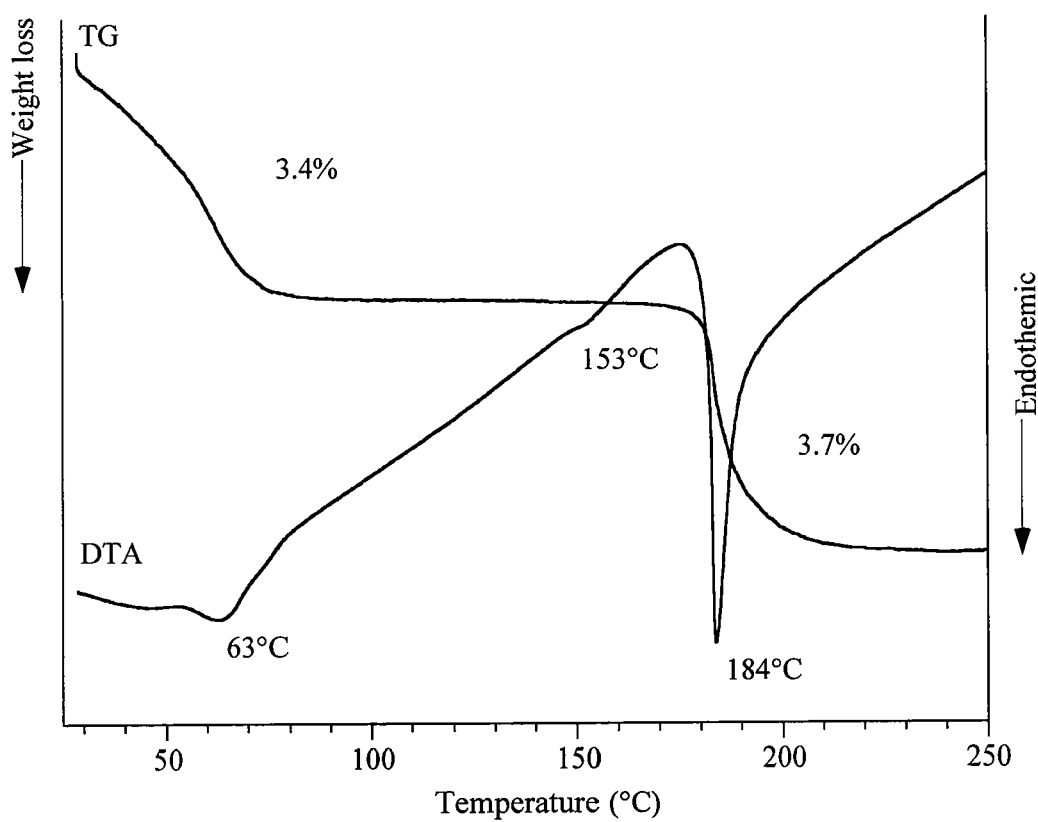
FIG. 4 shows the results of thermally analyzing type II crystals of (2S)-5-amino-2-{[1-(trans-4-methylcyclohexyl)-1H-imidazol-4-yl]methyl}valeric acid p-toluenesulfonate monohydrate. In this thermal analysis (TG/DTA), measurement was performed at a heating rate of 10° C./min. under a stream of 200 mL/min. dry nitrogen.

Thermal analysis (TG/DTA) in FIGS. 2 and 4 was conducted by measurement at a heating rate of 10° C./min. under a stream of 200 mL/min. dry nitrogen.

A pharmaceutical composition containing the compound of the present invention represented by the general formula (I) or the pharmacologically acceptable salt thereof can be prepared according to various formulation methods usually used by selecting an appropriate preparation according to an administration method.

The pharmaceutical composition comprising the compound of the present invention represented by the general formula (I) or the pharmacologically acceptable salt thereof as a principal ingredient, when administered to a mammal (particularly, a human), can be administered systemically or locally through an oral or parenteral route.

Examples of oral forms of pharmaceutical drugs include tablets, pills, powders, granules, capsules, solutions, suspensions, emulsions, syrups, and elixirs. These forms of pharmaceutical drugs are usually prepared as a pharmaceutical composition containing the compound of the present invention represented by the general formula (I) or the pharmacologically acceptable salt thereof as a principal ingredient mixed with pharmaceutically acceptable additives such as diluents, excipients, or carriers. The preparation of the pharmaceutical composition can be performed according to a conventional method using pharmaceutically acceptable diluents, excipients, or carriers, or other additives appropriately selected according to need from arbitrary appropriate pharmaceutically acceptable binders, disintegrants, lubricants, swelling agents, swelling aids, coating agents, plasticizers, stabilizers, antiseptics, antioxidants, coloring agents, solubilizing agents, suspending agents, emulsifying agents, sweeteners, preservatives, buffers, humectants, and so on.

Examples of parenteral forms of pharmaceutical drugs include injections, ointments, gels, creams, poultice, patches, aerosols, inhalants, sprays, eye drops, nasal drops, and suppositories. These forms of pharmaceutical drugs are usually prepared as a pharmaceutical composition containing the compound of the present invention represented by the general formula (I) or the pharmacologically acceptable salt thereof as a principal ingredient mixed with pharmaceutically acceptable additives such as diluents, excipients, or carriers. The preparation of the pharmaceutical composition can be performed according to a conventional method using pharmaceutically acceptable diluents, excipients, or carriers, or other additives appropriately selected according to need from arbitrary appropriate pharmaceutically acceptable stabilizers, antiseptics, solubilizing agents, humectants, preservatives, antioxidants, flavors, gelling agents, neutralizing agents, buffers, tonicity agents, surfactants, coloring agents, buffering agents, thickeners, wetting agents, fillers, absorption promoters, suspending agents, binders, and so on.

Examples of references on the pharmaceutically acceptable excipients can include "Handbook of Pharmaceutical Excipients, 2nd Edition, (1994), Edited by A. Wade and P. J. Weller".

Moreover, examples of references on the pharmaceutically acceptable carriers or diluents can include "Remington's Pharmaceutical Sciences, Mack Publishing Co. (A. R. Gennaro edit. 1985)".

The compound of the present invention represented by the general formula (I) or the pharmacologically acceptable salt thereof can be used in combination with an additional drug. The drugs that can be used in combination therewith include anticoagulants (warfarin, heparin, low-molecular-weight heparin, antithrombin drugs, anti-Xa drugs, etc.), antiplatelet drugs (aspirin, ticlopidine, clopidogrel, prasugrel, phosphodiesterase inhibitors, etc.), enzymes related to fibrinolysis (tPA, genetically modified tPA, plasminogen activators such as urokinase, streptokinase, plasmin, etc.), anticancer drugs, anti-inflammatory drugs, antifibrotic drugs, hypotensive drugs, anti-pulmonary hypertension drugs, and immunosuppressive drugs.

The dose of the compound of the present invention represented by the general formula (I) or the pharmacologically acceptable salt thereof differs depending on symptoms, age, body weight, the kind or dose of the drug to be administered in combination therewith, etc. When the compound of the present invention represented by the general formula (I) or the pharmacologically acceptable salt thereof is used as a pharmaceutical drug for the human body, its dose ranges from 0.01 mg to 5000 mg, preferably 0.1 mg to 1000 mg, more preferably 1 mg to 200 mg, in a single dose per adult in terms of the amount of the compound (I) and ranges from 0.001 mg/kg to 100 mg/kg, preferably 0.005 mg/kg to 20 mg/kg, more preferably 0.01 mg/kg to 5 mg/kg of the compound (I) in terms of the body weight. This daily dose is administered systemically or locally through an oral or parenteral route once every few days or at one or several dosages per day or continuously administered to veins for a duration ranging from 1 hour to 24 hours per day. Moreover, the daily dose may exceed the amount above, if necessary.

EXAMPLES

Hereinafter, the present invention will be described specifically with reference to Reference Examples, Examples, Test Examples and Preparation Examples. However, the present invention is not limited to these methods by any means.

The symbols "$^1$H-NMR", "MS", "HRMS" and "LRMS" in the Examples mean a "nuclear magnetic resonance spectrum", a "mass spectrometry spectrum", "high-resolution mass spectrometry spectrum", and a "low-resolution mass spectrometry spectrum", respectively. The ratio of eluting solvents described in chromatographic separation/purification represents a volume ratio, unless otherwise specified. The terms inside the parentheses of "$^1$H-NMR" represent assay solvents, all of which used TMS (tetramethylsilane) as an internal standard. Multiplicity in $^1$H-NMR means s=singlet, d=doublet, t=triplet, q=quartet, m=multiplet, and br=broad. Moreover, in the present specification, the following abbreviations were used:

$CDCl_3$: deuterated chloroform;
$CD_3OD$: deuterated methanol;
Me: methyl group;
Et: ethyl group;
tBu: tert-butyl group;
Boc: tert-butoxycarbonyl group;

Cbz: (benzyloxy)carbonyl group;
TBDMS: tert-butyl(dimethyl)silyl group;
TBDPS: tert-butyl(diphenyl)silyl group.

Reference Example 1

Tert-Butyl 5-[(tert-butoxycarbonyl)amino]-2-(diethoxyphosphoryl)valerate

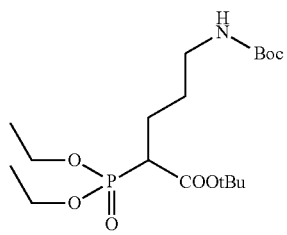

[Formula 40]

tert-Butyl diethylphosphonoacetate (20.0 g) was dissolved in tetrahydrofuran (500 mL). To the solution, sodium hydride (63%, 3.32 g) was added at 0° C., and the mixture was stirred at 0° C. for 15 minutes and at room temperature for 1 hour. A solution of tert-butyl (3-bromopropyl)carbamate (20.0 g) in tetrahydrofuran (20 mL) was slowly added thereto at room temperature, and the mixture was stirred at room temperature for 18 hours. To the reaction solution, saturated aqueous ammonium chloride was added, and organic matter was extracted with ethyl acetate. The organic layer was washed with saturated sodium chloride solution, then dried over anhydrous sodium sulfate, and filtered, and the solvent was distilled off under reduced pressure to obtain a crude product. This crude product was purified by silica gel column chromatography (eluting solvent: hexane/ethyl acetate=1/1-ethyl acetate) to obtain the title compound (26.6 g).

$^1$H-NMR (CDCl$_3$) δ: 1.31-1.36 (6H, m), 1.44 (9H, m), 1.48 (9H, m), 1.51-1.59 (2H, m), 1.78-2.00 (2H, m), 2.83 (1H, ddd, J=22.9, 10.7, 4.4 Hz), 3.06-3.18 (2H, m), 4.10-4.18 (4H, m), 4.58 (1H, br).

Reference Example 2

Tert-Butyl 5-[(tert-butoxycarbonyl)amino]-2-(1H-imidazol-4-ylmethyl)valerate

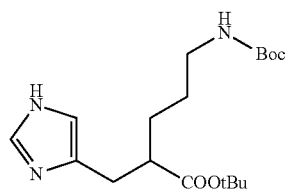

[Formula 41]

To a solution of the compound (8.35 g) obtained in Reference Example 1 in acetonitrile (100 mL), 1,8-diazabicyclo[5.4.0]undec-7-ene (4.58 mL) and lithium chloride (1.30 g) were added at room temperature. To this suspension, 1-trityl-1H-imidazole-4-carbaldehyde (6.90 g) was added, and the mixture was stirred overnight at room temperature. The solvent was distilled off under reduced pressure. To the residue, ethyl acetate and a 10% aqueous citric acid were added. This solution was separated into aqueous and organic layers. Then, the organic layer was washed with saturated sodium chloride solution, saturated aqueous sodium bicarbonate, and saturated sodium chloride solution in this order. The organic layer was dried over anhydrous sodium sulfate to obtain a mixture of tert-butyl (2E)-5-[(tert-butoxycarbonyl)amino]-2-[(1-trityl-1H-imidazol-4-yl)methylene]valerate and tert-butyl (2Z)-5-[(tert-butoxycarbonyl)amino]-2-[(1-trityl-1H-imidazol-4-yl)methylene]valerate (11.3 g). This mixture was suspended in methanol (500 mL). To this suspension, 10% palladium-carbon catalyst (hydrated, 4 g) was added, and the mixture was stirred at room temperature for 3 days under a hydrogen atmosphere. The catalyst was filtered off, and the filtrate was concentrated under reduced pressure. The residue was purified by silica gel chromatography (eluting solvent: methylene chloride/methanol=9/1) to obtain the title compound (5.60 g).

$^1$H-NMR (CDCl$_3$) δ: 1.41 (9H, s), 1.44 (9H, s), 1.48-1.57 (3H, m), 1.57-1.66 (1H, m), 2.58-2.68 (1H, m), 2.73 (1H, dd, J=14.7, 5.3 Hz), 2.89 (1H, dd, J=14.7, 8.4 Hz), 3.02-3.19 (2H, m), 4.67 (1H, br s), 6.79 (1H, s), 7.54 (1H, s).

Reference Example 3

5-[(tert-Butoxycarbonyl)amino]-2-(methoxycarbonyl)valeric acid

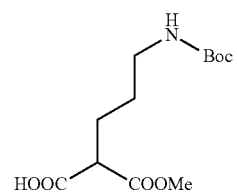

[Formula 42]

To dimethyl malonate (102 mL), a solution of sodium methoxide in methanol (28%, 90.4 mL) was added at room temperature, and the mixture was stirred at 60° C. for 30 minutes. The white suspension was cooled to room temperature. Then, tert-butyl (3-bromopropyl)carbamate (106 g) was added thereto at once, and the mixture was stirred at room temperature for 12 hours. To the reaction solution, water was added, and organic matter was extracted with diethyl ether. The organic layer was washed with a 1 N aqueous sodium hydroxide and saturated sodium chloride solution in this order, then dried over anhydrous sodium sulfate, and filtered, and the solvent was distilled off under reduced pressure to obtain a crude product of dimethyl {3-[(tert-butoxycarbonyl)amino]propyl}malonate. The obtained ester (94 g) was dissolved in methanol (100 mL). To the solution, a solution of lithium hydroxide monohydrate (13.6 g) in water (300 mL) and methanol (300 mL) was added at 0° C., and the mixture was stirred at room temperature for 15 hours. Methanol was distilled off under reduced pressure, and organic matter was extracted with ethyl acetate. 2 N hydrochloric acid (160 mL) was added to the aqueous layer, followed by extraction with ethyl acetate. The organic layer was washed with saturated sodium chloride solution, then dried over anhydrous sodium sulfate, and filtered, and the solvent was distilled off under reduced pressure to obtain a crude product. This crude product was purified by silica gel column chromatography (eluting solvent: methylene chloride-methylene chloride/methanol=10/1) to obtain the title compound (69.1 g).

¹H-NMR (CDCl₃) δ: 1.44 (9H, m), 1.50-1.60 (2H, m), 1.86-2.01 (2H, m), 3.07-3.20 (2H, m), 3.43 (1H, m), 3.77 (3H, s), 4.64 (1H, br).

Reference Example 4

1-(trans-4-Methylcyclohexyl)-1H-imidazole-4-carbaldehyde

[Step 1] Ethyl 1-(trans-4-methylcyclohexyl)-1H-imidazole-4-carboxylate

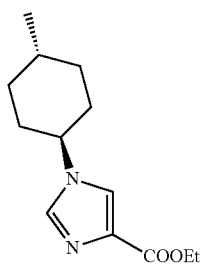

[Formula 43]

Ethyl 3-(dimethylamino)-2-isocyanoacrylate (Liebigs Annalen der Chemie, 1979, p. 1444) (1.52 g) was dissolved in trans-4-methylcyclohexylamine (3.07 g), and the solution was stirred at 70° C. for 4 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=2/1-1/2) to obtain the title compound (1.90 g).
¹H-NMR (CDCl₃) δ: 0.96 (3H, d, J=6.6 Hz), 1.13 (2H, m), 1.39 (3H, d, J=7.0 Hz), 1.47 (1H, m), 1.68 (2H, m), 1.88 (2H, m), 2.12 (2H, m), 3.91 (1H, tt, J=12.1, 3.9 Hz), 4.36 (2H, q, J=7.0 Hz), 7.54 (1H, s), 7.66 (1H, s).

[Step 2] [1-(trans-4-Methylcyclohexyl)-1H-imidazol-4-yl]methanol

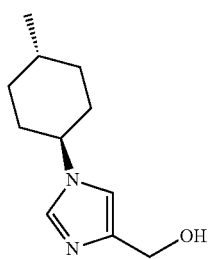

[Formula 44]

Lithium aluminum hydride (92%, 0.31 g) was suspended in tetrahydrofuran (6 mL). The compound (1.50 g) obtained in Step 1 of this Reference Example was dissolved in tetrahydrofuran (6 mL), and this solution was slowly added dropwise to the suspension at 0° C. After stirring at 0° C. for 30 minutes, the reaction solution was diluted with diethyl ether, and saturated aqueous sodium sulfate was added thereto. After stirring at room temperature for 1 hour, the formed inorganic salt was removed by filtration through celite. The filtrate was concentrated under reduced pressure to obtain a crude product. This crude product was washed with a mixed solvent of hexane and ethyl acetate (5:1) to obtain the title compound (1.09 g).
¹H-NMR (CDCl₃) δ: 0.95 (3H, d, J=6.6 Hz), 1.04-1.17 (2H, m), 1.44 (1H, m), 1.59-1.73 (2H, m), 1.81-1.89 (2H, m), 2.04-2.13 (2H, m), 2.78 (1H, br), 3.84 (1H, tt, J=12.1, 3.9 Hz), 4.59 (2H, s), 6.91 (1H, s), 7.49 (1H, s).

[Step 3] 1-(trans-4-Methylcyclohexyl)-1H-imidazole-4-carbaldehyde

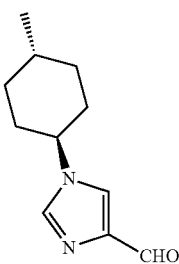

[Formula 45]

The compound (1.04 g) obtained in Step 2 of this Reference Example was dissolved in toluene (10 mL). To the solution, a solution of sodium bicarbonate (1.35 g) in water (5 mL), iodine (2.72 g), and 2,2,6,6-tetramethyl-1-piperidinyloxy (84 mg) were added in this order, and the mixture was stirred at room temperature for 2 hours. To the reaction solution, saturated aqueous sodium thiosulfate was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=1/1-1/2) to obtain the title compound (0.900 g).
¹H-NMR (CDCl₃) δ: 0.97 (3H, d, J=6.8 Hz), 1.09-1.19 (2H, m), 1.48 (1H, m), 1.65-1.75 (2H, m), 1.87-1.93 (2H, m), 2.11-2.18 (2H, m), 3.95 (1H, tt, J=12.2, 3.9 Hz), 7.62 (1H, s), 7.68 (1H, s), 9.87 (1H, s).

Reference Example 5

1-(trans-4-Ethylcyclohexyl)-1H-imidazole-4-carbaldehyde

[Step 1] [1-(4-Ethylcyclohexyl)-1H-imidazol-4-yl]methanol

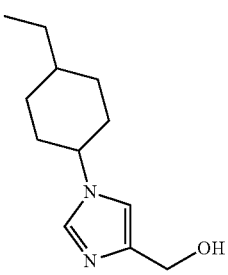

Formula 46]

Ethyl 3-(dimethylamino)-2-isocyanoacrylate (2.00 g) was dissolved in 4-ethylcyclohexylamine (3.37 g), and the solution was stirred at 70° C. for 4.5 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure to obtain a crude product. Lithium aluminum hydride (92%, 0.490 g) was suspended in tetrahydrofuran (12 mL). The produced crude product was dissolved in tetrahydrofuran (12 mL), and this solution was slowly added dropwise to the suspension at 0° C. After stirring at 0° C. for 30 minutes, the reaction solution was diluted with diethyl ether, and saturated aqueous sodium sulfate was added thereto. After stirring at room temperature for 1 hour, the formed inorganic salt was removed by filtration through celite. The filtrate was concentrated under reduced pressure to obtain a crude product. This crude product was purified by silica gel column chromatography (eluting solvent: methylene chloride-methylene chloride/methanol=9/1) to obtain the title compound (1.35 g, diastereomeric mixture, trans:cis=4:1).

$^1$H-NMR (CDCl$_3$) δ: 0.91 (0.6H, t, J=7.0 Hz), 0.92 (2.4H, t, J=7.0 Hz), 1.01-1.13 (1.6H, m), 1.16-1.40 (2.8H, m), 1.50-1.97 (5H, m), 2.07-2.15 (1.6H, m), 3.85 (0.8H, tt, J=12.1, 3.9 Hz), 3.99 (0.2H, tt, J=8.6, 4.3 Hz), 4.59 (1.6H, s), 4.60 (0.4H, s), 6.91 (0.8H, s), 6.94 (0.2H, s), 7.49 (0.8H, s), 7.53 (0.2H, s).

[Step 2] 1-(trans-4-Ethylcyclohexyl)-1H-imidazole-4-carbaldehyde

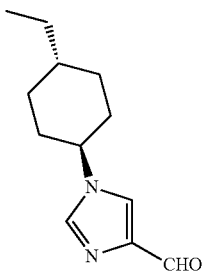

[Formula 47]

The compound (1.00 g) obtained in Step 1 of this Reference Example was dissolved in toluene (10 mL). To the solution, a solution of sodium bicarbonate (1.21 g) in water (6 mL), iodine (2.19 g), and 2,2,6,6-tetramethyl-1-piperidinyloxy (75 mg) were added in this order, and the mixture was stirred at room temperature for 12 hours. To the reaction solution, saturated aqueous sodium thiosulfate was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=2/1-1/1) to obtain the title compound (468 mg).

$^1$H-NMR (CDCl$_3$) δ: 0.92 (3H, t, J=7.0 Hz), 1.10 (2H, m), 1.19-1.34 (3H, m), 1.68 (2H, m), 1.97 (2H, m), 2.17 (2H, m), 3.95 (1H, tt, J=12.1, 3.5 Hz), 7.62 (1H, s), 7.69 (1H, s), 9.87 (1H, s).

Reference Example 6

1-(3-Ethylcyclobutyl)-1H-imidazole-4-carbaldehyde

[Step 1] Benzyl (3-ethylcyclobutyl)carbamate

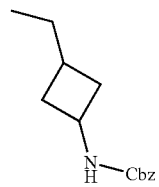

[Formula 48]

3-Ethylcyclobutanecarboxylic acid (1.67 g) was dissolved in toluene (20 mL), and diisopropylethylamine (5.32 mL) was added thereto. The solution was heated to 100° C., and a solution of diphenylphosphoryl azide (3.09 mL) in toluene (10 mL) was added dropwise thereto over 40 minutes. After stirring at 100° C. for 15 minutes, benzyl alcohol (1.48 mL) was added, and the mixture was further stirred at 100° C. for 15 minutes. The reaction solution was cooled. A 0.2 N aqueous sodium hydroxide was added thereto, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=20/1-10/1) to obtain the title compound (1.81 g, diastereomeric mixture, trans:cis=1:1).

$^1$H-NMR (CDCl$_3$) δ: 0.78 (1.5H, t, J=7.4 Hz), 0.81 (1.5H, t, J=7.4 Hz), 1.38 (1H, dq, J=7.4, 7.4 Hz), 1.46 (1H, dq, J=7.4, 7.4 Hz), 1.31-1.42 (2H, m), 1.89-2.03 (2H, m), 2.41-2.54 (1H, m), 4.00 (0.5H, m), 4.23 (0.5H, m), 4.75-4.90 (1H, br), 5.06 (2H, s), 7.22-7.40 (5H, m).

[Step 2] [1-(3-Ethylcyclobutyl)-1H-imidazol-4-yl]methanol

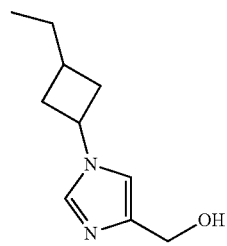

[Formula 49]

The compound (1.81 g) obtained in Step 1 of this Reference Example was dissolved in methyl acetate (7 mL). To the solution, 10% palladium-carbon catalyst (hydrated, 100 mg) was added, and the mixture was stirred at room temperature for 8 hours under a hydrogen atmosphere at normal pressure. After filtration through celite, the filtrate was concentrated under reduced pressure to obtain a crude product of 3-ethylcyclobutanamine. This crude product and ethyl 3-(dimethylamino)-2-isocyanoacrylate (650 mg) were mixed and stirred at 75° C. for 10 hour in a sealed tube. To the reaction solution, saturated aqueous ammonium chloride was added, and organic matter was extracted with ethyl acetate. The organic layer was dried over anhydrous sodium sulfate and filtered, and the solvent was distilled off under reduced pressure. The residue was purified by silica gel column chromatography (eluting solvent: hexane/ethyl acetate=1/1-1/2) to obtain ethyl 1-(3-ethylcyclobutyl)-1H-imidazole-4-carboxylate.

Lithium aluminum hydride (92%, 80 mg) was suspended in tetrahydrofuran (4 mL). To this suspension, a solution of ethyl 1-(3-ethylcyclobutyl)-1H-imidazole-4-carboxylate in tetrahydrofuran (5 mL) was slowly added dropwise at 0° C. After stirring at 0° C. for 30 minutes, the reaction solution was diluted with diethyl ether, and saturated aqueous sodium sulfate was added thereto. After stirring at room temperature for 1 hour, the formed inorganic salt was removed by filtration through celite. The filtrate was concentrated under reduced pressure to obtain a crude product. This crude product was purified by silica gel column chromatography (eluting solvent: methylene chloride-methylene chloride/methanol=5/1) to obtain the title compound (119 mg, diastereomeric mixture, trans:cis=1:1).
$^1$H-NMR (CDCl$_3$) δ: 0.86 (1.5H, t, J=7.4 Hz), 0.90 (1.5H, t, J=7.4 Hz), 1.48 (1H, dq, J=7.4, 7.4 Hz), 1.56 (1H, dq, J=7.4, 7.4 Hz), 1.84-1.93 (1H, m), 1.96-2.08 (0.5H, m), 2.20-2.32 (1.5H, m), 2.39-2.49 (1H, m), 2.59-2.67 (1H, m), 4.38 (0.5H, tt, J=9.4, 7.8 Hz), 4.59 (1H, s), 4.60 (1H, s), 4.63 (0.5H, tt, J=7.8, 7.4 Hz), 6.93 (0.5H, s), 6.98 (0.5H, s), 7.46 (0.5H, s), 7.49 (0.5H, s).

[Step 3]
1-(3-Ethylcyclobutyl)-1H-imidazole-4-carbaldehyde

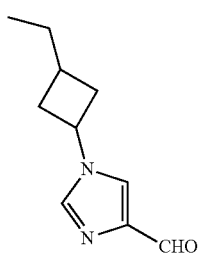

[Formula 50]

The compound (119 mg) obtained in Step 2 of this Reference Example was dissolved in toluene (5 mL). To this solution, a solution of sodium bicarbonate (166 mg) in water (4 mL), iodine (305 mg), and 2,2,6,6-tetramethyl-1-piperidinyloxy (11 mg) were added in this order, and the mixture was stirred at room temperature for 12 hours. To the reaction solution, saturated aqueous sodium thiosulfate was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=1/1-1/2) to obtain the title compound (115 mg, diastereomeric mixture, trans:cis=1:1). $^1$H-NMR (CDCl$_3$) δ: 0.86 (1.5H, t, J=7.3 Hz), 0.90 (1.5H, t, J=7.3 Hz), 1.44 (9H, s), 1.51 (1H, dq, J=7.4, 7.4 Hz), 1.59 (1H, dq, J=7.4, 7.4 Hz), 1.87-1.97 (1H, m), 2.04-2.13 (0.5H, m), 2.28-2.38 (1.5H, m), 2.42-2.52 (1H, m), 2.66-2.75 (1H, m), 4.48 (0.5H, tt, J=9.0, 7.8 Hz), 4.72 (0.5H, tt, J=7.8, 7.4 Hz), 7.58 (0.5H, s), 7.61 (0.5H, s), 7.69 (0.5H, s), 7.74 (0.5H, s), 9.87 (0.5H, s), 9.88 (0.5H, s).

Reference Example 7

1-(3-Methylcyclobutyl)-1H-imidazole-4-carbaldehyde

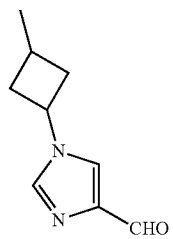

[Formula 51]

The title compound (9.1 mg, diastereomeric mixture, trans:cis=1:1) was obtained from 3-methylcyclobutanecarboxylic acid (1.70 g) in the same way as in Reference Example 6.
$^1$H-NMR (CDCl$_3$) δ: 1.18 (1.5H, d, J=6.6 Hz), 1.27 (1.5H, d, J=6.6 Hz), 1.93 (1H, m), 2.22-2.32 (1.5H, m), 2.46-2.60 (1.5H, m), 2.74 (1H, m), 4.46 (0.5H, tt, J=9.4, 7.4 Hz), 4.79 (0.5H, tt, J=7.8, 7.4 Hz), 7.58 (0.5H, s), 7.61 (0.5H, s), 7.70 (0.5H, s), 7.73 (0.5H, s), 9.87 (0.5H, s), 9.88 (0.5H, s).

Reference Example 8

1-(trans-4-Hydroxycyclohexyl)-1H-imidazole-4-carbaldehyde

[Step 1] [1-(trans-4-{[tert-Butyl(dimethyl)silyl]oxy}cyclohexyl)-1H-imidazol-4-yl]methanol

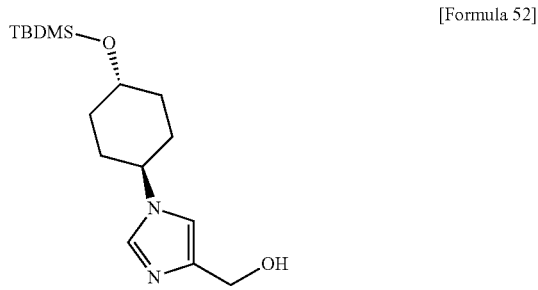

[Formula 52]

Ethyl 3-(dimethylamino)-2-isocyanoacrylate (300 mg) and trans-4-{[tert-butyl(dimethyl)silyl]oxy}cyclohexylamine (Synthetic Communications, 1990, Vol. 20, p. 1073) (1.02 g) were mixed and stirred at 85° C. for 12 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure. The residue was purified by silica gel column chromatography (eluting solvent: hexane/ethyl acetate-4/1-1/1). Lithium aluminum hydride (92%, 105 mg) was suspended in tetrahydrofuran (8 mL). The produced crude product was dissolved in tetrahydrofuran (6 mL), and this solution was slowly added dropwise to the suspension at 0° C. After stirring at 0° C. for 1 hour, the reaction solution was diluted with diethyl ether, and saturated aqueous sodium sulfate was added thereto. After stirring at room temperature for 1 hour, the formed inorganic salt was removed by filtration through celite. The filtrate was concentrated under reduced pressure to obtain a crude product. This crude product was washed with a mixed solvent of hexane and ethyl acetate (2:1) to obtain the title compound (260 mg).

$^1$H-NMR (CD$_3$OD) δ: 0.09 (6H, s), 0.90 (9H, s), 1.50 (2H, m), 1.81 (2H, m), 1.96-2.10 (4H, m), 3.76 (1H, m), 4.05 (1H, m), 4.48 (2H, s), 7.12 (1H, s), 7.64 (1H, s).

[Step 2] 1-(trans-4-{[tert-Butyl(dimethyl)silyl]oxy}cyclohexyl)-1H-imidazole-4-carbaldehyde

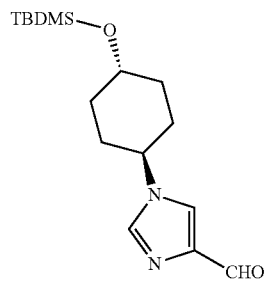

[Formula 53]

The compound (260 mg) obtained in Step 1 of this Reference Example was dissolved in toluene (10 mL) and methylene chloride (1 mL). To the solution, a solution of sodium bicarbonate (210 mg, 2.50 mmol) in water (8 mL), iodine (370 mg), and 2,2,6,6-tetramethyl-1-piperidinyloxy (15 mg) were added in this order, and the mixture was stirred at room temperature for 12 hours. To the reaction solution, saturated aqueous sodium thiosulfate was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=2/1-1/1) to obtain the title compound (258 mg).

$^1$H-NMR (CDCl$_3$) δ: 0.08 (6H, s), 0.90 (9H, s), 1.52 (2H, m), 1.75 (2H, m), 2.02 (2H, m), 2.16 (2H, m), 3.68 (1H, m), 4.00 (1H, m), 7.62 (1H, s), 7.67 (1H, s), 9.87 (1H, s).

[Step 3] 1-(trans-4-Hydroxycyclohexyl)-1H-imidazole-4-carbaldehyde

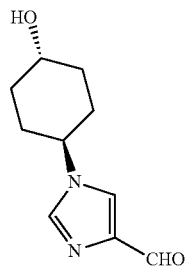

[Formula 54]

The compound (540 mg) obtained in Step 2 of this Reference Example was dissolved in tetrahydrofuran (8 mL). To this solution, a solution of tetrabutylammonium fluoride in tetrahydrofuran (1.0 M, 2.62 mL) was added, and the mixture was stirred at room temperature for 8 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure to obtain a crude product. This crude product was purified by diol-bonded silica gel column chromatography (eluting solvent: hexane/ethyl acetate=1/1-ethyl acetate) to obtain the title compound (250 mg).

$^1$H-NMR (CDCl$_3$) δ: 1.52 (2H, m), 1.78 (2H, m), 2.11-2.25 (4H, m), 3.76 (1H, m), 4.03 (1H, m), 7.63 (1H, s), 7.68 (1H, s), 9.87 (1H, s).

Reference Example 9

1-(4-Hydroxy-4-methylcyclohexyl)-1H-imidazole-4-carbaldehyde

[Step 1] Benzyl (4-hydroxy-4-methylcyclohexyl)carbamate

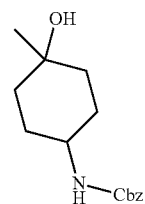

[Formula 55]

Benzyl (4-oxocyclohexyl)carbamate (2.00 g) was dissolved in tetrahydrofuran (15 mL), and cerium chloride (5.98 g) was added thereto. The reaction solution was cooled to −78° C. Then, a solution of methyllithium in diethyl ether (1.6 M, 15.2 mL) was added thereto, and the mixture was stirred at −78° C. for 1 hour and at 0° C. for 3 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=9/1-2/1) to obtain a diastereomeric mixture of the title compound (1.31 g, trans:cis=3:7).

$^1$H-NMR (CDCl$_3$) δ: 1.23 (3H, s), 1.44-1.67 (6H, m), 1.81 (2H, m), 3.48 (1H, m), 4.65 (1H, m), 5.08 (2H, s), 7.29-7.41 (5H, m).

[Step 2] Ethyl 1-(4-hydroxy-4-methylcyclohexyl)-1H-imidazole-4-carboxylate

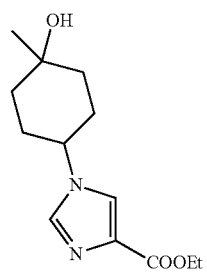

[Formula 56]

The compound obtained in Step 1 of this Reference Example was dissolved in ethanol (12 mL). To the solution, 10% palladium-carbon catalyst (hydrated, 400 mg) was added, and the mixture was stirred at room temperature for 15 hours under a hydrogen atmosphere at normal pressure. After filtration through celite, the filtrate was concentrated under reduced pressure to obtain a crude product of 4-amino-1-methylcyclohexanol. This crude product and ethyl 3-(dimethylamino)-2-isocyanoacrylate (450 mg) were mixed and stirred at 75° C. for 8 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure. The residue was purified by silica gel column chromatography (eluting solvent: hexane/ethyl acetate=1/1-ethyl acetate) to obtain a diastereomeric mixture of the title compound (462 mg, trans:cis=1:3).

$^1$H-NMR (CDCl$_3$) δ: 1.31 (2.25H, s), 1.34 (0.75H, s), 1.38 (3H, t, J=7.0 Hz), 1.52-1.70 (2H, m), 1.77-1.96 (4H, m), 2.08-2.19 (2H, m), 3.93 (0.75H, tt, J=12.2, 3.9 Hz), 4.06 (0.25H, m), 4.12 (0.5H, q, J=7.0 Hz), 4.36 (1.5H, q, J=7.0 Hz), 7.57 (1H, s), 7.68 (0.25H, s), 7.70 (0.75H, s).

[Step 3] 1-(4-Hydroxy-4-methylcyclohexyl)-1H-imidazole-4-carbaldehyde

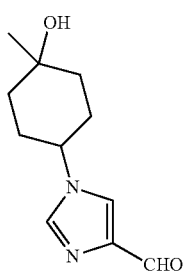

[Formula 57]

Lithium aluminum hydride (92%, 60 mg) was suspended in tetrahydrofuran (5 mL). To this suspension, a solution of the compound (455 mg) obtained in Step 2 of this Reference Example in tetrahydrofuran (5 mL) was slowly added dropwise at 0° C. After stirring at 0° C. for 4 hours and at room temperature for 30 minutes, the reaction solution was diluted with diethyl ether, and saturated aqueous sodium sulfate was added thereto. After stirring at room temperature for 1 hour, the formed inorganic salt was removed by filtration through celite. The filtrate was concentrated under reduced pressure. The obtained crude product was dissolved in methylene chloride (8 mL) and chloroform (4 mL), and manganese dioxide (2.00 g) was added thereto. After stirring at room temperature for 15 hours, the inorganic salt was removed by filtration through celite. The filtrate was concentrated under reduced pressure to obtain a crude product. This crude product was purified by silica gel column chromatography (eluting solvent: hexane/ethyl acetate=1/1-ethyl acetate) to obtain a diastereomeric mixture of the title compound (300 mg, trans:cis=1:3).

$^1$H-NMR (CDCl$_3$) δ: 1.32 (2.25H, s), 1.36 (0.75H, s), 1.54-1.73 (2H, m), 1.78-2.00 (4H, m), 2.11-2.23 (2H, m), 3.97 (0.75H, tt, J=12.2, 3.9 Hz), 4.10 (0.25H, m), 7.66 (1H, s), 7.72 (0.25H, s), 7.75 (0.75H, s), 9.86 (0.75H, s), 9.87 (0.25H, s).

Reference Example 10

1-[exo-Bicyclo[2.2.1]hept-2-yl]-1H-imidazole-4-carbaldehyde

[Step 1] Ethyl 1-[exo-bicyclo[2.2.1]hept-2-yl]-1H-imidazole-4-carboxylate

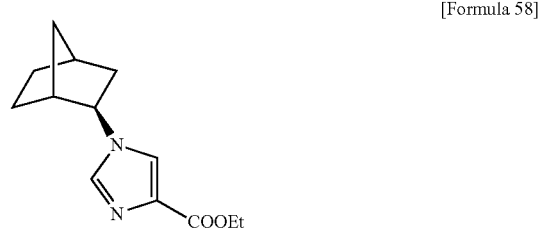 [SMILES: CCOC(=O)c1cn([C@@H]2CC3CCC2C3)cn1]

[Formula 58]

Ethyl 3-(dimethylamino)-2-isocyanoacrylate (0.58 g) was dissolved in exo-2-aminonorbornane (0.46 g), and the solution was stirred at 150° C. for 1.5 hours. The reaction solution was purified by silica gel column chromatography (eluting solvent: methylene chloride-methylene chloride/methanol=95/5 and ethyl acetate) to obtain the title compound (0.50 g).

$^1$H-NMR (CDCl$_3$) δ: 1.22-1.37 (3H, m), 1.38 (3H, t, J=7.1 Hz), 1.56-1.65 (2H, m), 1.65-1.73 (1H, m), 1.75-1.82 (1H, m), 1.97-2.04 (1H, m), 2.48 (1H, m), 2.52-2.55 (1H, m), 4.04-4.09 (1H, m), 4.37 (2H, q, J=7.1 Hz), 7.57 (1H, s), 7.67 (1H, s).

[Step 2] 1-[exo-Bicyclo[2.2.1]hept-2-yl]-1H-imidazole-4-carbaldehyde

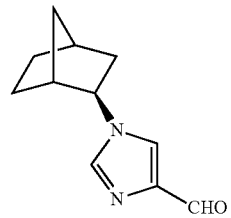

[Formula 59]

The title compound (0.21 g) was obtained from the compound (0.50 g) obtained in Step 1 of this Reference Example in the same way as in Steps 2 and 3 of Reference Example 4.

$^1$H-NMR (CDCl$_3$) δ: 1.23-1.41 (3H, m), 1.56-1.66 (2H, m), 1.67-1.75 (1H, m), 1.75-1.82 (1H, m), 2.01-2.07 (1H, m), 2.49 (1H, m), 2.53-2.57 (1H, m), 4.08-4.12 (1H, m), 7.63 (1H, s), 7.69 (1H, s), 9.87 (1H, s).

Reference Example 11

1-[endo-Bicyclo[2.2.1]hept-2-yl]-1H-imidazole-4-carbaldehyde

[Step 1] Ethyl 1-[endo-Bicyclo[2.2.1]hept-2-yl]-1H-imidazole-4-carboxylate

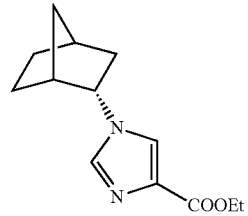

[Formula 60]

Ethyl 3-(dimethylamino)-2-isocyanoacrylate (0.58 g) and endo-2-aminonorbornane hydrochloride (0.61 g) were dissolved in n-butanol (5.8 mL). Then, to the solution, triethylamine (0.58 mL) was added at room temperature, and the mixture was stirred at 150° C. for 6.5 hours. The reaction solution was concentrated and then purified by silica gel column chromatography (eluting solvent: hexane/ethyl acetate=50/50-ethyl acetate) to obtain the title compound (0.13 g).

$^{1}$H-NMR (CDCl$_{3}$) δ: 1.19-1.71 (7H, m), 1.40 (3H, t, J=7.1 Hz), 2.19-2.27 (1H, m), 2.42 (1H, m), 2.60 (1H, m), 4.38 (2H, q, J=7.1 Hz), 4.44-4.49 (1H, m), 7.54 (1H, s), 7.65 (1H, s).

[Step 2] 1-[endo-Bicyclo[2.2.1]hept-2-yl]-1H-imidazole-4-carbaldehyde

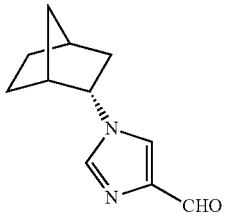

[Formula 61]

The title compound (0.17 g) was obtained from the compound (0.42 g) obtained in Step 1 of this Reference Example in the same way as in Steps 2 and 3 of Reference Example 4.

$^{1}$H-NMR (CDCl$_{3}$) δ: 1.18-1.25 (1H, m), 1.30-1.37 (1H, m), 1.44-1.73 (5H, m), 2.22-2.30 (1H, m), 2.45 (1H, m), 2.62 (1H, m), 4.47-4.53 (1H, m), 7.61 (1H, s), 7.68 (1H, s), 9.89 (1H, s).

Reference Example 12

1-Adamantan-2-yl-1H-imidazole-4-carbaldehyde

[Step 1] Ethyl 1-adamantan-2-yl-1H-imidazole-4-carboxylate

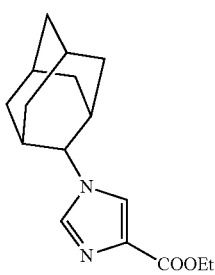

[Formula 62]

Ethyl 3-(dimethylamino)-2-isocyanoacrylate (0.50 g), 2-aminoadamantane (0.54 g), and n-butanol (2.5 mL) were added and stirred at 150° C. for 13 hours. To the reaction solution, water was added, and organic matter was extracted with ethyl acetate. The organic layer was concentrated and then purified by silica gel column chromatography (eluting solvent: methylene chloride-methylene chloride/methanol=95/5 and ethyl acetate) to obtain the title compound (0.24 g).

$^{1}$H-NMR (CDCl$_{3}$) δ: 1.40 (3H, t, J=7.2 Hz), 1.61-2.08 (12H, m), 2.52 (2H, m), 4.20 (1H, m), 4.38 (2H, q, J=7.2 Hz), 7.67 (1H, s), 7.76 (1H, s).

[Step 2] 1-Adamantan-2-yl-1H-imidazole-4-carbaldehyde

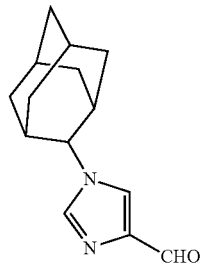

[Formula 63]

The title compound (0.15 g) was obtained from the compound (0.37 g) obtained in Step 1 of this Reference Example in the same way as in Steps 2 and 3 of Reference Example 4.

$^{1}$H-NMR (CDCl$_{3}$) δ: 1.49-2.10 (12H, m), 2.53 (2H, m), 4.24 (1H, m), 7.74 (1H, s), 7.80 (1H, s), 9.90 (1H, s).

Reference Example 13

1-(trans-4-Phenoxycyclohexyl)-1H-imidazole-4-carbaldehyde

[Step 1] tert-Butyl(trans-4-phenoxycyclohexyl)carbamate

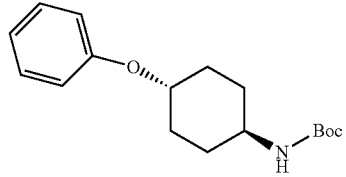

[Formula 64]

tert-Butyl(cis-4-hydroxycyclohexyl)carbamate (2.00 g), phenol (1.14 g), and triphenylphosphine (3.17 g) were dissolved in tetrahydrofuran (40.0 mL). Then, to the solution, diisopropyl azodicarboxylate (6.49 mL) was added dropwise at room temperature, and the mixture was stirred at room temperature for 63 hours. The reaction solution was concentrated and then purified by silica gel column chromatography (eluting solvent: hexane-hexane/ethyl acetate-90/10) to obtain the title compound (1.80 g).

$^{1}$H-NMR (CDCl$_{3}$) δ: 1.20-1.30 (2H, m), 1.45 (9H, s), 1.51-1.61 (2H, m), 2.05-2.16 (4H, m), 3.47-3.58 (1H, m), 4.17 (1H, m), 6.81-6.95 (3H, m), 7.21-7.29 (2H, m).

[Step 2] trans-4-Phenoxycyclohexanamine hydrochloride

[Formula 65]

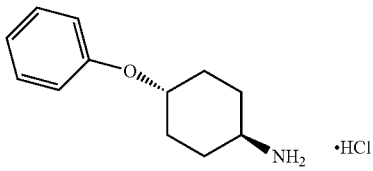

The compound (1.80 g) obtained in Step 1 of this Reference Example was dissolved in ethyl acetate (18.0 mL). To the solution, 4 M hydrochloric acid/ethyl acetate (18.0 mL) was added at room temperature, and the mixture was stirred for 1 hour. To the reaction solution, hexane (18.0 mL) was added, and the precipitated solid was then collected by filtration and washed with a mixed solvent of hexane and ethyl acetate (50:50) to obtain the title compound (1.01 g).

$^1$H-NMR (CD$_3$OD) δ: 1.48-1.61 (4H, m), 2.07-2.14 (2H, m), 2.18-2.25 (2H, m), 3.13-3.21 (1H, m), 4.28 (1H, m), 6.87-6.94 (3H, m), 7.21-7.28 (2H, m).

[Step 3] Ethyl 1-(trans-4-phenoxycyclohexyl)-1H-imidazole-4-carboxylate

[Formula 66]

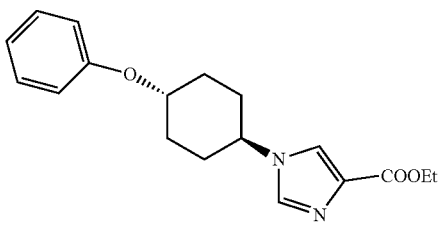

Ethyl 3-(dimethylamino)-2-isocyanoacrylate (0.70 g) and the compound (1.14 g) obtained in Step 2 of this Reference Example were dissolved in n-butanol (7.0 mL). Then, to the solution, triethylamine (0.70 mL) was added at room temperature, and the mixture was stirred at 150° C. for 3.25 hours. The reaction solution was concentrated and then purified by silica gel column chromatography (eluting solvent: hexane/ethyl acetate=50/50-ethyl acetate) to obtain the title compound (0.28 g).

$^1$H-NMR (CDCl$_3$) δ: 1.39 (3H, t, J=7.1 Hz), 1.57-1.71 (2H, m), 1.80-1.90 (2H, m), 2.22-2.37 (4H, m), 4.08 (1H, m), 4.29 (1H, m), 4.37 (2H, q, J=7.1 Hz), 6.85-7.00 (3H, m), 7.26-7.32 (2H, m), 7.59 (1H, s), 7.69 (1H, s).

[Step 4] 1-(trans-4-Phenoxycyclohexyl)-1H-imidazole-4-carbaldehyde

[Formula 67]

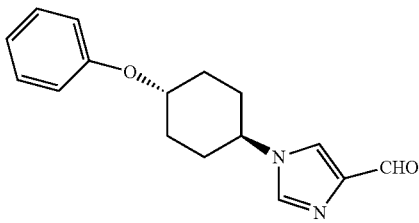

The title compound (0.07 g) was obtained from the compound (0.28 g) obtained in Step 3 in the same way as in Steps 2 and 3 of Reference Example 4.

$^1$H-NMR (CDCl$_3$) δ: 1.62-1.73 (2H, m), 1.80-1.91 (2H, m), 2.24-2.38 (4H, m), 4.11 (1H, m), 4.30 (1H, m), 6.88-7.01 (3H, m), 7.26-7.33 (2H, m), 7.66 (1H, s), 7.71 (1H, s), 9.88 (1H, s).

Reference Example 14

Ethyl 5-[(tert-butoxycarbonyl)amino]-2-(diethoxyphosphoryl)valerate

[Formula 68]

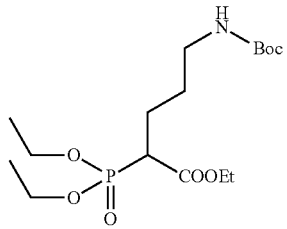

The title compound (14.1 g) was synthesized from triethyl phosphonoacetate (10 g) in the same way as in Reference Example 1.

Reference Example 15

1-(3,3-Dimethylcyclohexyl)-1H-imidazole-4-carbaldehyde

[Step 1] Ethyl 1-(3,3-dimethylcyclohexyl)-1H-imidazole-4-carboxylate

[Formula 69]

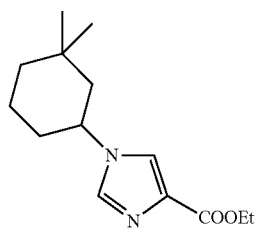

Hydroxylamine hydrochloride (8.76 g) was dissolved in water (100 mL). To the solution, a solution of sodium acetate (17.8 g) and 3,3-dimethylcyclohexanone (4.55 g) in methanol (20 mL) was added at room temperature, and the mixture was heated to reflux for 1.5 hours. Organic matter was extracted with ethyl acetate and dried over anhydrous sodium sulfate, and the solvent was then distilled off under reduced pressure to obtain a crude product of 3,3-dimethylcyclohexanone oxime.

Lithium aluminum hydride (4.11 g) was suspended in tetrahydrofuran (100 mL). To the suspension, a solution of the crude product of 3,3-dimethylcyclohexanone oxime thus obtained in tetrahydrofuran (50 mL) was added dropwise under ice cooling, and the mixture was subsequently heated to reflux for 10.5 hours. To the reaction solution, sodium sulfate decahydrate was added under ice cooling. Subsequently, ethyl acetate was added thereto, and the mixture was stirred for 30 minutes. After celite filtration, the solvent in the filtrate was distilled off under reduced pressure to obtain a crude product of 3,3-dimethylcyclohexylamine.

This crude product and ethyl 3-(dimethylamino)-2-isocyanoacrylate (3.04 g) were mixed and stirred at 70° C. for 16

[Step 2] 1-(3,3-Dimethylcyclohexyl)-1H-imidazole-4-carbaldehyde

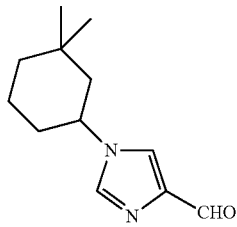

[Formula 70]

The title compound (1.23 g) was obtained from the compound (3.51 g) obtained in Step 1 of this Reference Example in the same way as in Steps 2 and 3 of Reference Example 4.

$^1$H-NMR (CDCl$_3$) δ: 0.92-0.96 (1H, m), 1.03 (6H, s), 1.18-1.26 (1H, m), 1.46-1.68 (3H, m), 1.76-1.85 (2H, m), 2.11-2.17 (1H, m), 4.11-4.19 (1H, m), 7.62 (1H, s), 7.68 (1H, s), 9.86 (1H, s).

Reference Example 16

Tert-Butyl (2-formylbutyl)carbamate

[Step 1] Ethyl 2-methylenebutyrate

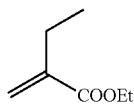

[Formula 71]

Potassium carbonate (5.5 g) was dissolved in water (15 mL). To the solution, ethyl 2-(diethoxyphosphoryl)butyrate (5.0 g) and a 37% aqueous formaldehyde (6.2 g) were added at room temperature, and the mixture was stirred at 85° C. for 45 minutes. Organic matter was extracted with diethyl ether, dried over anhydrous sodium sulfate, and filtered, and the solvent in the filtrate was distilled off under reduced pressure to obtain a crude product.

$^1$H-NMR (CDCl$_3$) δ: 1.08 (3H, t, J=7.4 Hz), 1.31 (3H, t, J=7.0 Hz), 2.30-2.36 (2H, m), 4.21 (2H, q, J=7.0 Hz), 5.51-5.52 (1H, m), 6.12-6.14 (1H, m).

[Step 2] Ethyl 2-[(benzylamino)methyl]butyrate

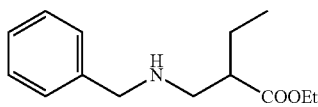

[Formula 72]

The compound obtained in Step 1 was dissolved in ethanol (7 mL). To the solution, benzylamine (2.7 mL) was added at room temperature, and the mixture was stirred at 70° C. for 17 hours. This mixture was purified by silica gel column chromatography (eluting solvent: hexane/ethyl acetate=1/1-1/3) to obtain the title compound (3.51 g).

hours. The solvent in the reaction solution was distilled off under reduced pressure, and the obtained residue was purified by silica gel column chromatography (eluting solvent: hexane-hexane/ethyl acetate=7/3) to obtain the title compound (2.34 g).

$^1$H-NMR (CDCl$_3$) δ: 0.91 (3H, t, J=7.4 Hz), 1.26 (3H, t, J=7.2 Hz), 1.53-1.70 (2H, m), 2.47-2.55 (1H, m), 2.69 (1H, dd, J=11.9, 4.9 Hz), 2.88 (1H, dd, J=11.9, 8.8 Hz), 3.79 (2H, d, J=4.3 Hz), 4.13-4.19 (2H, m), 7.22-7.26 (2H, m), 7.29-7.32 (3H, m).

[Step 3] Ethyl 2-{[(tert-butoxycarbonyl)amino]methyl}butyrate

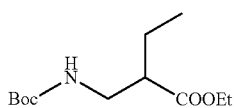

[Formula 73]

The compound (2.34 g) obtained in Step 2 was dissolved in ethanol (50 mL). To the solution, 10% palladium-carbon catalyst (hydrated, 1.17 g) was added, and the mixture was stirred for 4 hours under a hydrogen atmosphere. Subsequently, di-tert-butyl dicarbonate (2.6 g) was added thereto, and the mixture was stirred overnight. Di-tert-butyl dicarbonate (1.3 g) was further added thereto, and the mixture was stirred for 1 hour. The catalyst was filtered off, and the solvent in the filtrate was distilled off under reduced pressure. The obtained residue was purified by silica gel column chromatography (eluting solvent: hexane-hexane/ethyl acetate=8/2) to obtain the title compound (1.97 g).

$^1$H-NMR (CDCl$_3$) δ: 0.94 (3H, t, J=7.4 Hz), 1.27 (3H, t, J=7.4 Hz), 1.43 (9H, s), 1.49-1.71 (2H, m), 2.48-2.56 (1H, m), 3.21-3.28 (1H, m), 3.32-3.39 (1H, m), 4.11-4.20 (3H, m), 4.86 (1H, br s).

[Step 4] Ethyl 2-{[bis(tert-butoxycarbonyl)amino]methyl}butyrate

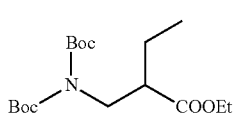

[Formula 74]

To a solution of the compound (578 mg) obtained in Step 3 in tetrahydrofuran (15 mL), a solution of n-BuLi in hexane (1.65 M, 1.57 mL) was added at −78° C., and the mixture was stirred for 1 hour. Subsequently, di-tert-butyl dicarbonate (668 mg) was added thereto at −78° C., and the mixture was gradually heated and then stirred overnight. To the reaction solution, aqueous ammonium chloride was added, and organic matter was extracted with ethyl acetate, dried over anhydrous sodium sulfate, and filtered. The solvent was distilled off under reduced pressure. The obtained residue was purified by silica gel column chromatography (eluting solvent: hexane/ethyl acetate=98/2-90/10) to obtain the title compound (684 mg).

[Step 5] tert-Butyl[2-(hydroxymethyl)butyl]carbamate

[Formula 75]

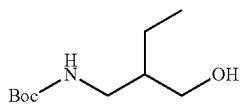

Lithium aluminum hydride (153 mg) was suspended in tetrahydrofuran (20 mL). To the suspension, a solution of the compound obtained in Step 4 in tetrahydrofuran (2 mL) was added dropwise under ice cooling, and the mixture was then stirred overnight. To the reaction solution, sodium sulfate decahydrate was added under ice cooling. Subsequently, ethyl acetate was added thereto, and the mixture was stirred. After celite filtration, the solvent in the filtrate was distilled off under reduced pressure. The obtained residue was purified by silica gel column chromatography (eluting solvent: hexane/ethyl acetate=9/1-3/7) to obtain the title compound (168 mg).

$^1$H-NMR (CDCl$_3$) δ: 0.93 (3H, t, J=7.4 Hz), 1.19-1.37 (2H, m), 1.45 (9H, s), 3.06-3.13 (1H, m), 3.28-3.36 (2H, m), 3.37-3.44 (1H, m), 3.56-3.62 (1H, m), 4.78 (1H, br s).

[Step 6] tert-Butyl (2-formylbutyl)carbamate

[Formula 76]

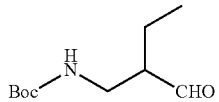

Oxalyl chloride (141 μL) was dissolved in methylene chloride (1 mL). To the solution, a solution of dimethyl sulfoxide (176 μL) in methylene chloride (1 mL) was added dropwise at −78° C., and the mixture was stirred for 15 minutes. A solution of the compound (168 mg) obtained in Step 5 in methylene chloride (2 mL) was added dropwise thereto at −78° C., and the mixture was stirred for 2 hours. Triethylamine (695 μL) was added thereto, and the mixture was heated to 0° C. and then stirred overnight. To the reaction solution, methylene chloride was added, and the organic layer was washed with water and saturated sodium chloride solution, then dried over anhydrous sodium sulfate, and filtered. The solvent was distilled off under reduced pressure. The obtained residue was purified by silica gel column chromatography (eluting solvent: hexane/ethyl acetate=9/1-7/3) to obtain the title compound (113 mg).

$^1$H-NMR (CDCl$_3$) δ: 1.02 (3H, t, J=7.8 Hz), 1.42 (9H, s), 1.48-1.54 (1H, m), 1.70-1.81 (1H, m), 2.43-2.51 (1H, m), 3.27-3.40 (2H, m), 4.82 (1H, br s), 9.68-9.69 (1H, m).

Reference Example 17

1-(cis-4-{[tert-Butyl(diphenyl)silyl]oxy}cyclohexyl)-1H-imidazole-4-carbaldehyde

[Step 1] tert-Butyl(cis-4-{[tert-butyl(diphenyl)silyl]oxy}cyclohexyl)carbamate

[Formula 77]

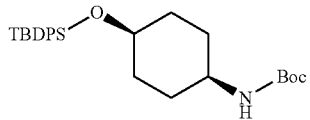

To a solution of tert-butyl(cis-4-hydroxycyclohexyl)carbamate (2.0 g) in dimethylformamide (40 mL), imidazole (756 mg) and t-butyldiphenylchlorosilane (2.86 mL) were added under ice cooling, and the mixture was stirred for 24 hours. Imidazole (226 mg) and t-butyldiphenylchlorosilane (858 μL) were further added thereto, and the mixture was stirred for 6 days. To the reaction solution, ethyl acetate was added, and the organic layer was washed three times with 10% sodium chloride solution, dried over anhydrous sodium sulfate, and filtered. The solvent was distilled off under reduced pressure. This residue was purified by silica gel column chromatography (eluting solvent: hexane/ethyl acetate=98/2-9/1) to obtain the title compound (5.09 g).

$^1$H-NMR (CDCl$_3$) δ: 1.07 (9H, s), 1.45 (9H, s), 1.57-1.71 (8H, m), 3.40-3.49 (1H, m), 3.88-3.92 (1H, m), 4.50-4.57 (1H, m), 7.34-7.44 (6H, m), 7.64-7.66 (4H, m).

[Step 2] cis-4-{[tert-Butyl(diphenyl)silyl]oxy}cyclohexanamine

[Formula 78]

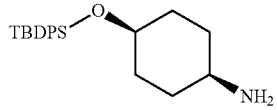

The compound obtained in Step 2 was dissolved in methylene chloride (25 mL). To the solution, trifluoroacetic acid (5 mL) was added under ice cooling, and the mixture was stirred for 45 minutes. Trifluoroacetic acid (5 mL) was further added thereto under ice cooling, and the mixture was stirred for 1 hour. The organic layer was washed with aqueous potassium carbonate, dried over anhydrous sodium sulfate, and filtered, and the solvent was distilled off under reduced pressure to obtain a crude product of the title compound (4.17 g).

[Step 3] Ethyl 1-(cis-4-{[tert-butyl(diphenyl)silyl]oxy}cyclohexyl)-1H-imidazole-4-carboxylate

[Formula 79]

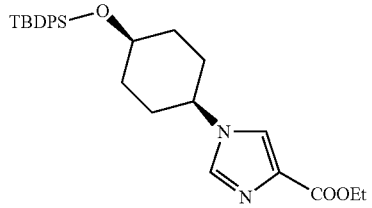

The compound obtained in Step 2 and ethyl 3-(dimethylamino)-2-isocyanoacrylate (1.56 g) were mixed and stirred at 70° C. for 33 hours. This mixture was purified by silica gel column chromatography (eluting solvent: hexane/ethyl acetate=8/2-ethyl acetate) to obtain the title compound (870 mg).

[Step 4] 1-(cis-4-{[tert-Butyl(diphenyl)silyl]oxy}cyclohexyl)-1H-imidazole-4-carbaldehyde

[Formula 80]

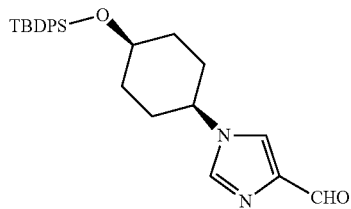

The title compound (307 mg) was obtained from the compound obtained in Step 3 of this Reference Example in the same way as in Steps 2 and 3 of Reference Example 4.

$^1$H-NMR (CDCl$_3$) δ: 1.11 (9H, s), 1.42-1.49 (2H, m), 1.81-1.93 (4H, m), 2.24-2.32 (2H, m), 3.95-4.01 (1H, m), 4.07-4.10 (1H, m), 7.37-7.41 (4H, m), 7.43-7.47 (2H, m), 7.65-7.67 (5H, m), 7.75 (1H, s), 9.90 (1H, s).

Reference Example 18

1-(cis-4-Methylcyclohexyl)-1H-imidazole-4-carbaldehyde

[Step 1] Ethyl 1-(cis-4-methylcyclohexyl)-1H-imidazole-4-carboxylate

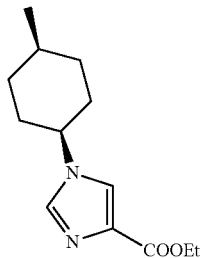

[Formula 81]

To cis-4-methylcyclohexylamine hydrochloride (5.0 g), water and sodium bicarbonate were added, and the organic layer was separated. The organic layer was dried over anhydrous sodium sulfate, and the solvent was distilled off to prepare a free form of cis-4-methylcyclohexylamine (770 mg). 5 N hydrochloric acid was further added to the aqueous layer obtained above. PoraPak Rxn CX (ion-exchange resin, 30 g) was added thereto, and the mixture was left at room temperature. The resin was washed with deionized water, followed by elution with a 0.4 N ammonia/methanol solution. The eluate was concentrated to obtain a free form of cis-4-methylcyclohexylamine (1.01 g). The obtained free forms were combined (1.78 g) and reacted in the same way as in Step 1 of Reference Example 4 to obtain the title compound (1.67 g).

[Step 2] 1-(cis-4-Methylcyclohexyl)-1H-imidazole-4-carbaldehyde

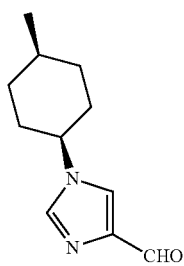

[Formula 82]

Lithium aluminum hydride (0.35 g) was suspended in tetrahydrofuran (10 mL). To the suspension, a solution of the compound (1.67 g) obtained in Step 1 of this Reference Example in tetrahydrofuran (10 mL) was added dropwise under ice cooling. The mixture was stirred at 0° C. for 30 minutes and then at room temperature for 2 hours and 40 minutes, and water (2 mL), 5 N aqueous sodium hydroxide (2 mL), and water (6 mL) were added thereto in this order under cooling. The mixture was stirred at room temperature for 2 hours. Then, anhydrous sodium sulfate was added thereto, and the mixture was filtered. The filtrate was concentrated under reduced pressure, and the obtained residue was dissolved in methylene chloride (20 mL). To the solution, manganese dioxide (21.6 g) was added, and the mixture was stirred at room temperature for 17 hours and then filtered through celite. The filtrate was concentrated under reduced pressure. The obtained residue was purified by silica gel column chromatography (eluting solvent: hexane/ethyl acetate=50/50-20/80) to obtain the title compound (0.79 g).

$^1$H-NMR (CDCl$_3$) δ: 1.00 (3H, d, J=7.0 Hz), 1.45-1.52 (2H, m), 1.64-1.73 (3H, m), 1.85-2.07 (4H, m), 4.06-4.13 (1H, m), 7.67 (1H, d, J=1.2 Hz), 7.74 (1H, d, J=1.2 Hz), 9.89 (1H, s).

Example 1

5-Amino-2-[(1-cyclohexyl-1H-imidazol-4-yl)methyl]valeric acid

[Step 1] tert-Butyl 5-[(tert-butoxycarbonyl)amino]-2-[(1-cyclohex-2-en-1-yl-1H-imidazol-4-yl)methyl]valerate

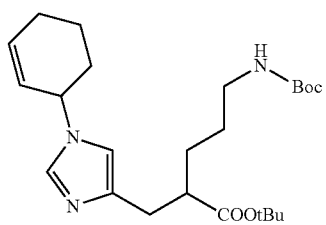

[Formula 83]

The compound (200 mg) obtained in Reference Example 2 was dissolved in N,N-dimethylformamide (3 mL), and sodium hydride (63%, 43 mg) was added thereto at 0° C. After stirring at 0° C. for 15 minutes and at room temperature for 45 minutes, 3-bromocyclohexene (90%, 0.150 mL) was added thereto at 0° C., and the mixture was stirred at room temperature for 30 minutes. To the reaction solution, saturated aqueous ammonium chloride was added, and organic matter was extracted with ethyl acetate. The organic layer was washed with water, then dried over anhydrous sodium sulfate, and filtered, and the solvent was distilled off under reduced pressure to obtain a crude product. This crude product was purified by silica gel column chromatography (eluting solvent: methylene chloride-methylene chloride/methanol=10/1) to obtain the title compound (220 mg).

$^1$H-NMR (CDCl$_3$) δ: 1.39 (9H, s), 1.44 (9H, s), 1.47-2.15 (10H, m), 2.60-2.70 (2H, m), 2.85 (1H, m), 3.02-3.18 (2H, m), 4.61 (1H, m), 4.76 (1H, br), 5.70 (1H, m), 6.05 (1H, m), 6.68 (1H, s), 7.42 (1H, s).

[Step 2] tert-Butyl 5-[(tert-butoxycarbonyl)amino]-2-[(1-cyclohexyl-1H-imidazol-4-yl)methyl]valerate

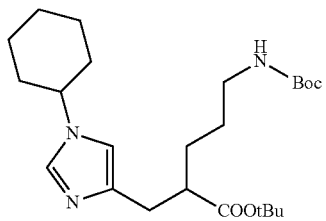

[Formula 84]

10% palladium-carbon catalyst (hydrated, 200 mg) was suspended in a solution of the compound (250 mg) obtained in Step 1 of this Example in ethanol (6 mL). The suspension was stirred at room temperature for 3 hours under a hydrogen atmosphere at normal pressure. The reaction solution was filtered through celite, and the filtrate was concentrated. The obtained crude product was purified by silica gel column chromatography (eluting solvent: methylene chloride/methanol=20/1–10/1) to obtain the title compound (240 mg).

$^1$H-NMR (CDCl$_3$) δ: 1.19-1.36 (4H, m), 1.38 (9H, s), 1.44 (9H, s), 1.48-1.64 (5H, m), 1.73 (1H, m), 1.88 (2H, m), 2.06 (2H, m), 2.59-2.70 (2H, m), 2.84 (1H, m), 3.05-3.16 (2H, m), 3.81 (1H, m), 4.76 (1H, br), 6.68 (1H, s), 7.42 (1H, s).

[Step 3] 5-Amino-2-[(1-cyclohexyl-1H-imidazol-4-yl)methyl]valeric acid

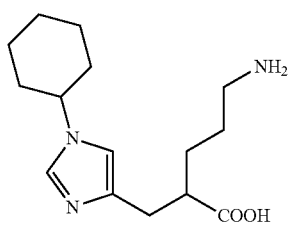

[Formula 85]

The compound (100 mg) obtained in Step 2 of this Example was dissolved in tetrahydrofuran (1 mL), and 2 N hydrochloric acid (5 mL) was added thereto. After heating to reflux for 2.5 hours, the solvent was distilled off under reduced pressure. The obtained crude hydrochloride was dissolved in water, and DOWEX 50WX8-200 was added thereto. The resin was washed with water, followed by elution with 4% ammonia water. The eluate was concentrated to obtain the title compound (7.0 mg).

$^1$H-NMR (CD$_3$OD) δ: 1.23-1.75 (10H, m), 1.87 (2H, m), 2.04 (2H, m), 2.46-2.59 (2H, m), 2.84-2.95 (3H, m), 3.95 (1H, m), 6.95 (1H, s), 7.57 (1H, s).

HRMS (ESI): m/z calcd for C$_{15}$H$_{25}$N$_3$NaO$_2$: 302.1845 [M+-Na]$^+$. found: 302.1835.

Example 2

5-Amino-2-{[1-(trans-4-methylcyclohexyl)-1H-imidazol-4-yl]methyl}valeric acid

[Step 1] tert-Butyl 5-[(tert-butoxycarbonyl)amino]-2-{[1-(trans-4-methylcyclohexyl)-1H-imidazol-4-yl]methyl}valerate

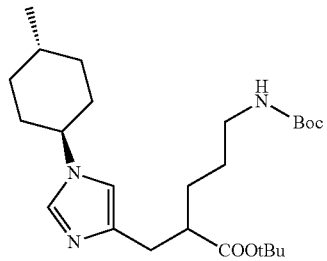

[Formula 86]

The compound (970 mg) obtained in Reference Example 1 was dissolved in acetonitrile (7 mL), and lithium chloride (100 mg) was added thereto. After stirring at room temperature for 1 hour, 1,8-diazabicyclo[5.4.0]undec-7-ene (0.38 mL) was added thereto. After further stirring at room temperature for 30 minutes, a solution of the compound (350 mg) obtained in Reference Example 4 in acetonitrile (4 mL) was added thereto, and the mixture was stirred at room temperature for 14 hours. The solvent was distilled off under reduced pressure. Then, water was added to the residue, and organic matter was extracted with ethyl acetate. The organic layer was dried over anhydrous sodium sulfate and filtered, and the solvent was distilled off under reduced pressure. The obtained crude product was dissolved in ethanol (10 mL). To the solution, 10% palladium-carbon catalyst (hydrated, 200 mg) was added, and the mixture was stirred at room temperature for 9 hours under a hydrogen atmosphere at normal pressure. After filtration through celite, the filtrate was concentrated under reduced pressure to obtain a crude product. This crude product was purified by silica gel column chromatography (eluting solvent: methanol-methylene chloride/methanol=20/1) to obtain the title compound (435 mg).

$^1$H-NMR (CDCl$_3$) δ: 0.94 (3H, d, J=6.3 Hz), 1.05-1.14 (2H, m), 1.38 (9H, s), 1.41-1.68 (7H, m), 1.44 (9H, s), 1.81-1.87 (2H, m), 2.03-2.08 (2H, m), 2.60-2.69 (2H, m), 2.84 (1H, m), 3.05-3.15 (2H, m), 3.78 (1H, tt, J=11.7, 3.9 Hz), 4.73 (1H, br), 6.67 (1H, s), 7.40 (1H, s).

[Step 2] 5-Amino-2-{[1-(trans-4-methylcyclohexyl)-1H-imidazol-4-yl]methyl}valeric acid

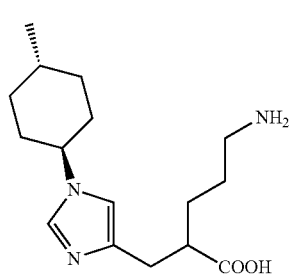

[Formula 87]

To the compound (430 mg) obtained in Step 1 of this Example, 2 N hydrochloric acid (5 mL) was added, and the mixture was heated to reflux for 3 hours. After cooling, the solvent was distilled off under reduced pressure. The obtained crude hydrochloride was dissolved in water, and DOWEX 50WX8-200 was added thereto. The resin was washed with water, followed by elution with 4% ammonia water. The eluate was concentrated, and the crude product was washed with acetone to obtain the title compound (90 mg).

$^1$H-NMR (CD$_3$OD) δ: 0.95 (3H, d, J=6.6 Hz), 1.07-1.20 (2H, m), 1.38-1.77 (7H, m), 1.79-1.87 (2H, m), 1.97-2.06 (2H, m), 2.43-2.57 (2H, m), 2.81-2.95 (3H, m), 3.92 (1H, tt, J=11.7, 3.5 Hz), 6.93 (1H, s), 7.54 (1H, s).

HRMS (ESI): m/z calcd for C$_{16}$H$_{28}$N$_3$O$_2$: 294.2182 [M+H]$^+$. found: 294.2183.

Example 3

5-Amino-2-{[1-(trans-4-ethylcyclohexyl)-1H-imidazol-4-yl]methyl}valeric acid

[Step 1] Methyl 5-[(tert-butoxycarbonyl)amino]-2-{[1-(trans-4-ethylcyclohexyl)-1H-imidazol-4-yl]methyl}valerate

[Formula 88]

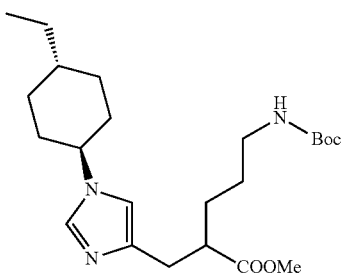

The compound (100 mg) obtained in Reference Example 5 and the compound (267 mg) obtained in Reference Example 3 were suspended in cyclohexane (5 mL). To this suspension, a solution of piperidine (0.048 mL) and propionic acid (0.036 mL) in cyclohexane (2 mL) was added, and the mixture was heated to reflux for 10 hours. After cooling, to the reaction solution, aqueous potassium carbonate was added, and organic matter was extracted with ethyl acetate. The organic layer was washed with saturated sodium chloride solution, then dried over anhydrous sodium sulfate, and filtered, and the solvent was distilled off under reduced pressure. The obtained crude product was dissolved in methanol (8 mL). To the solution, 10% palladium-carbon catalyst (hydrated, 200 mg) was added, and the mixture was stirred at room temperature for 8 hours under a hydrogen atmosphere at normal pressure. After filtration through celite, the filtrate was concentrated under reduced pressure to obtain a crude product. This crude product was purified by silica gel column chromatography (eluting solvent: hexane/ethyl acetate=2/1-1/2) to obtain the title compound (185 mg).

$^1$H-NMR (CDCl$_3$) δ: 0.91 (3H, t, J=7.0 Hz), 1.06 (2H, m), 1.15-1.68 (9H, m), 1.44 (9H, s), 1.93 (2H, m), 2.09 (2H, m), 2.71 (1H, dd, J=13.7, 5.9 Hz), 2.80 (1H, m), 2.89 (1H, dd, J=13.7, 7.8 Hz), 3.03-3.17 (2H, m), 3.63 (3H, s), 3.81 (1H, tt, J=12.1, 3.9 Hz), 4.76 (1H, br), 6.68 (1H, s), 7.47 (1H, s).

[Step 2] 5-Amino-2-{[1-(trans-4-ethylcyclohexyl)-1H-imidazol-4-yl]methyl}valeric acid

[Formula 89]

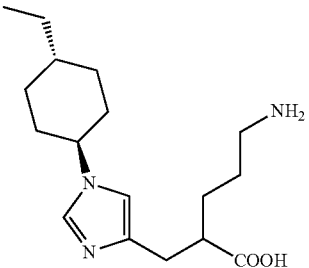

To the compound (180 mg) obtained in Step 1 of this Example, 5 N hydrochloric acid (4 mL) was added, and the mixture was heated to reflux for 3 hours. After cooling, the solvent was distilled off under reduced pressure. The obtained crude hydrochloride was dissolved in methanol, and DOWEX 50WX8-200 was added thereto. The resin was washed with water, followed by elution with 4% ammonia water. The eluate was concentrated, and the crude product was washed with acetone to obtain the title compound (53 mg).

$^1$H-NMR (CD$_3$OD) δ: 0.92 (3H, t, J=7.0 Hz), 1.10 (2H, m), 1.17-1.33 (3H, m), 1.42-1.75 (6H, m), 1.91 (2H, m), 2.05 (2H, m), 2.43-2.58 (2H, m), 2.79-2.95 (3H, m), 3.93 (1H, tt, J=12.1, 3.5 Hz), 6.94 (1H, s), 7.56 (1H, s).

HRMS (ESI): m/z calcd for C$_{17}$H$_{30}$N$_3$O$_2$: 308.2338 [M+H]$^+$. found: 308.2338.

Example 4

5-Amino-2-{[1-(3-ethylcyclobutyl)-1H-imidazol-4-yl]methyl}valeric acid

[Step 1] Methyl 5-[(tert-butoxycarbonyl)amino]-2-{[1-(3-ethylcyclobutyl)-1H-imidazol-4-yl]methyl}valerate

[Formula 90]

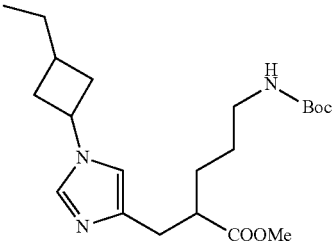

The compound (115 mg) obtained in Reference Example 6 and the compound (355 mg) obtained in Reference Example 3 were suspended in cyclohexane (6 mL). To the suspension, a solution of piperidine (0.064 mL) and propionic acid (0.048 mL) in cyclohexane (3 mL) was added, and the mixture was heated to reflux for 14 hours. After cooling, aqueous potassium carbonate was added to the reaction solution, and organic matter was extracted with ethyl acetate. The organic layer was washed with saturated sodium chloride solution, then dried over anhydrous sodium sulfate, and filtered, and the solvent was distilled off under reduced pressure. The obtained crude product was dissolved in ethanol (5 mL). To the solution, 10% palladium-carbon catalyst (hydrated, 200 mg) was added, and the mixture was stirred at room temperature for 8 hours under a hydrogen atmosphere at normal pressure. After filtration through celite, the filtrate was concentrated under reduced pressure to obtain a crude product. This crude product was purified by silica gel column chromatography (eluting solvent: hexane/ethyl acetate=1/1-1/2) to obtain the title compound (190 mg, diastereomeric mixture, trans:cis=1:1).

$^1$H-NMR (CDCl$_3$) δ: 0.86 (1.5H, t, J=7.3 Hz), 0.90 (1.5H, t, J=7.3 Hz), 1.44 (9H, s), 1.44-1.70 (6H, m), 1.81-1.90 (1H, m), 1.94-2.04 (0.5H, m), 2.18-2.30 (1.5H, m), 2.37-2.47 (1H, m), 2.57-2.64 (1H, m), 2.66-2.73 (1H, m), 2.76-2.83 (1H, m), 2.86-2.93 (1H, m), 3.04-3.17 (2H, m), 3.64 (3H, s), 4.34 (0.5H, tt, J=9.3, 7.8 Hz), 4.58 (0.5H, tt, J=7.8, 7.3 Hz), 4.79 (1H, br), 6.68 (0.5H, s), 6.73 (0.5H, s), 7.39 (0.5H, s), 7.42 (0.5H, s).

[Step 2] 5-Amino-2-{[1-(3-ethylcyclobutyl)-1H-imidazol-4-yl]methyl}valeric acid

[Formula 91]

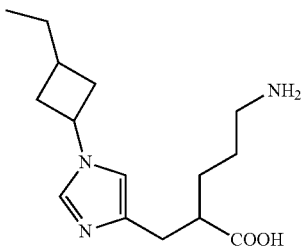

To the compound (185 mg) obtained in Step 1 of this Example, 5 N hydrochloric acid (4 mL) was added, and the mixture was heated to reflux for 3 hours. After cooling, the solvent was distilled off under reduced pressure. The obtained crude hydrochloride was dissolved in methanol, and DOWEX 50WX8-200 was added thereto. The resin was washed with methanol, followed by elution with 4% ammonia water. The eluate was concentrated, and the crude product was washed with acetone to obtain the title compound (51 mg, diastereomeric mixture, trans:cis=1:1).

$^1$H-NMR (CD$_3$OD) δ: 0.87 (1.5H, t, J=7.4 Hz), 0.91 (1.5H, t, J=7.4 Hz), 1.45-1.73 (6H, m), 1.85-2.06 (1H, m), 2.17-2.29 (1.5H, m), 2.41-2.64 (4H, m), 2.82-2.95 (3H, m), 4.47 (0.5H, tt, J=9.4, 7.8 Hz), 4.72 (0.5H, tt, J=8.2, 7.8 Hz), 6.97 (0.5H, s), 7.03 (0.5H, s), 7.53 (0.5H, s), 7.56 (0.5H, s).

HRMS (ESI): m/z calcd for C$_{15}$H$_{26}$N$_3$O$_2$: 280.2025 [M+H]$^+$. found: 280.2015.

Example 5

5-Amino-2-{[1-(3-methylcyclobutyl)-1H-imidazol-4-yl]methyl}valeric acid

[Formula 92]

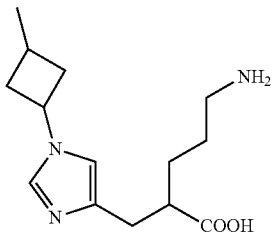

The title compound (2.0 mg, diastereomeric mixture, trans:cis=1:1) was obtained from the compound (10 mg) obtained in Reference Example 7 in the same way as in Example 4.

$^1$H-NMR (CD$_3$OD) δ: 1.15 (1.5H, d, J=6.6 Hz), 1.24 (1.5H, d, J=6.6 Hz), 1.44-1.72 (4H, m), 1.85-1.96 (1H, m), 2.10-2.22 (1.5H, m), 2.41-2.63 (4.5H, m), 2.81-2.95 (3H, m), 4.45 (0.5H, tt, J=9.4, 7.4 Hz), 4.79 (0.5H, tt, J=7.8, 7.8 Hz), 6.98 (0.5H, s), 7.02 (0.5H, s), 7.54 (0.5H, s), 7.57 (0.5H, s).

HRMS (ESI): m/z calcd for C$_{14}$H$_{24}$N$_3$O$_2$: 266.1869 [M+H]$^+$. found: 266.1874.

Example 6

(2RS)-5-Amino-2-({1-[(1R,3s,5S)-bicyclo[3.1.0]hexan-3-yl]-1H-imidazol-4-yl}methyl)valeric acid

[Step 1] (1R,3r,5S)-bicyclo[3.1.0]hexan-3-yl methanesulfonate

[Formula 93]

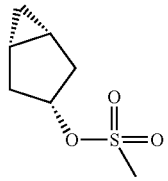

To a solution of (1R,3r,5S)-bicyclo[3.1.0]hexan-3-ol (1.00 g) in methylene chloride (10 mL), triethylamine (1.70 mL) and methanesulfonyl chloride (0.94 mL) were added at 0° C., and the mixture was stirred at room temperature for 12 hours. To the reaction solution, water was added, and organic matter was extracted with methylene chloride. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=4/1-2/1) to obtain the title compound (1.34 g).

$^1$H-NMR (CDCl$_3$) δ: 0.44 (1H, m), 0.54 (1H, m), 1.35 (2H, m), 2.10 (2H, m), 2.26 (2H, m), 2.96 (3H, s), 5.19 (1H, m).

[Step 2] tert-Butyl (2RS)-2-([1-[(1R,3s,5S)-bicyclo[3.1.0]hexan-3-yl]-1H-imidazol-4-yl]methyl)-5-[(tert-butoxycarbonyl)amino]valerate

[Formula 94]

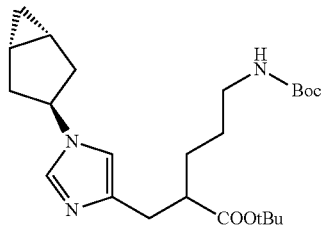

The compound (250 mg) obtained in Reference Example 2 was dissolved in N,N-dimethylformamide (4 mL), and cesium carbonate (690 mg) and the compound (250 mg) obtained in Step 1 of this Example were added thereto. After stirring at 110° C. for 9 hours, to the reaction solution, water was added, and organic matter was extracted with diethyl ether. The organic layer was washed with water, then dried over anhydrous sodium sulfate, and filtered, and the solvent was distilled off under reduced pressure to obtain a crude product. This crude product was purified by silica gel column chromatography (eluting solvent: methylene chloride-methylene chloride/methanol=10/1) to obtain the title compound (55 mg).

$^1$H-NMR (CDCl$_3$) δ: 0.26 (1H, dt, J=5.7, 3.9 Hz), 0.47 (1H, td, J=7.8, 5.7 Hz), 1.38 (9H, s), 1.44 (9H, s), 1.35-2.07 (8H, m), 2.26-2.33 (2H, m), 2.58-2.68 (2H, m), 2.83 (1H, m), 3.05-3.15 (2H, m), 4.03 (1H, tt, J=10.2, 7.4 Hz), 4.75 (1H, br), 6.65 (1H, s), 7.37 (1H, s).

[Step 3] (2RS)-5-Amino-2-({1-[(1R,3s,5S)-bicyclo[3.1.0]hexan-3-yl]-1H-imidazol-4-yl}methyl)valeric acid

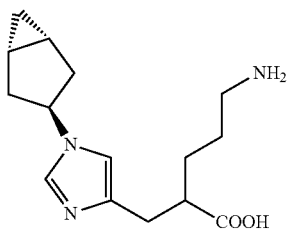

[Formula 95]

The compound (55 mg) obtained in Step 2 of this Example was dissolved in methylene chloride (2 mL). To the solution, trifluoroacetic acid (1 mL) was added, and the mixture was stirred at room temperature for 5 hours. Then, the solvent was distilled off under reduced pressure. Toluene was added to the residue, and the solvent was again distilled off under reduced pressure. The obtained crude trifluoroacetate was dissolved in water, and DOWEX 50WX8-200 was added thereto. The resin was washed with methanol, followed by elution with 4% ammonia water. The eluate was concentrated, and the crude product was washed with acetone to obtain the title compound (30 mg).

$^1$H-NMR (CD$_3$OD) δ: 0.34 (1H, dt, J=5.4, 3.9 Hz), 0.45 (1H, td, J=7.4, 5.4 Hz), 1.38-1.45 (2H, m), 1.46-1.71 (4H, m), 2.03-2.11 (2H, m), 2.23-2.30 (2H, m), 2.44-2.57 (2H, m), 2.82-2.95 (3H, m), 4.21 (1H, tt, J=10.2, 7.4 Hz), 6.92 (1H, s), 7.50 (1H, s).

HRMS (ESI): m/z calcd for C$_{15}$H$_{23}$N$_3$NaO$_2$: 300.1688 [M+Na]$^+$. found: 300.1679.

Example 7

5-Amino-2-{[1-(trans-4-hydroxycyclohexyl)-1H-imidazol-4-yl]methyl}valeric acid

[Step 1] Methyl 5-[(tert-butoxycarbonyl)amino]-2-{[1-(trans-4-hydroxycyclohexyl)-1H-imidazol-4-yl]methyl}valerate

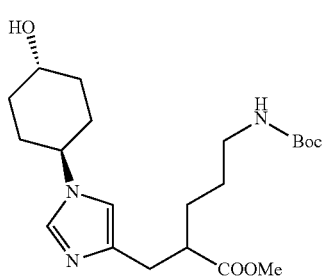

[Formula 96]

The compound (185 mg) obtained in Reference Example 8 and the compound (524 mg) obtained in Reference Example 3 were suspended in cyclohexane (6 mL). To the suspension, a solution of piperidine (0.094 mL) and propionic acid (0.071 mL) in cyclohexane (2 mL) was added, and the mixture was heated to reflux for 12 hours. After cooling, to the reaction solution, aqueous potassium carbonate was added, and organic matter was extracted with ethyl acetate. The organic layer was washed with saturated sodium chloride solution, then dried over anhydrous sodium sulfate, and filtered, and the solvent was distilled off under reduced pressure. The obtained crude product was dissolved in methanol (6 mL). To the solution, 10% palladium-carbon catalyst (hydrated, 200 mg) was added, and the mixture was stirred at room temperature for 7 hours under a hydrogen atmosphere at normal pressure. After filtration through celite, the filtrate was concentrated under reduced pressure to obtain a crude product. This crude product was purified by silica gel column chromatography (eluting solvent: methylene chloride-methylene chloride/methanol=9/1) to obtain the title compound (326 mg).

$^1$H-NMR (CDCl$_3$) δ: 1.40-1.88 (8H, m), 1.43 (9H, s), 2.08-2.16 (4H, m), 2.70 (1H, dd, J=14.6, 6.3 Hz), 2.80 (1H, m), 2.89 (1H, dd, J=14.6, 8.3 Hz), 3.03-3.15 (2H, m), 3.63 (3H, s), 3.72 (1H, m), 3.88 (1H, m), 4.73 (1H, br), 6.67 (1H, s), 7.47 (1H, s).

[Step 2] 5-Amino-2-{[1-(trans-4-hydroxycyclohexyl)-1H-imidazol-4-yl]methyl}valeric acid

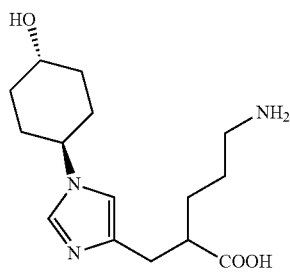

[Formula 97]

To the compound (246 mg) obtained in Step 1 of this Example, 5 N hydrochloric acid (5 mL) was added, and the mixture was heated to reflux for 3 hours. After cooling, the solvent was distilled off under reduced pressure. The obtained crude hydrochloride was dissolved in methanol, and DOWEX 50WX8-200 was added thereto. The resin was washed with water, followed by elution with 4% ammonia water. The eluate was concentrated, and the crude product was washed with acetone to obtain the title compound (74 mg).

$^1$H-NMR (CD$_3$OD) δ: 1.39-1.87 (8H, m), 2.01-2.13 (4H, m), 2.53-2.69 (2H, m), 2.84-2.97 (3H, m), 3.64 (1H, m), 4.09 (1H, m), 7.10 (1H, s), 8.01 (1H, s).

HRMS (ESI): m/z calcd for C$_{15}$H$_{26}$N$_3$O$_3$: 296.1974 [M+H]$^+$. found: 296.1975.

Example 8

5-Amino-2-{[1-(4-hydroxy-4-methylcyclohexyl)-1H-imidazol-4-yl]methyl}valeric acid

[Step 1] tert-Butyl 5-[(tert-butoxycarbonyl)amino]-2-{[1-(4-hydroxy-4-methylcyclohexyl)-1H-imidazol-4-yl]methyl}valerate

[Formula 98]

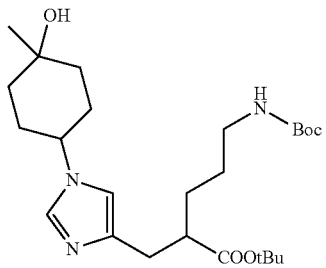

The compound (796 mg) obtained in Reference Example 1 was dissolved in acetonitrile (6 mL), and lithium chloride (111 mg) was added thereto. After stirring at room temperature for 1 hour, 1,8-diazabicyclo[5.4.0]undec-7-ene (0.34 mL) was added thereto. After further stirring at room temperature for 1 hour, a solution of the compound (300 mg) obtained in Reference Example 9 in acetonitrile (4 mL) was added thereto, and the mixture was stirred at room temperature for 12 hours. The solvent was distilled off under reduced pressure. Then, water was added to the residue, and organic matter was extracted with ethyl acetate. The organic layer was dried over anhydrous sodium sulfate and filtered, and the solvent was distilled off under reduced pressure. The obtained crude product was dissolved in ethanol (10 mL). To the solution, 10% palladium-carbon catalyst (hydrated, 150 mg) was added, and the mixture was stirred at room temperature for 9 hours under a hydrogen atmosphere at normal pressure. After filtration through celite, the filtrate was concentrated under reduced pressure to obtain a crude product. This crude product was purified by silica gel column chromatography (eluting solvent: hexane/ethyl acetate=2/1-1/3) to obtain a diastereomeric mixture of the title compound (431 mg, trans:cis=1:3).

$^1$H-NMR (CDCl$_3$) δ: 1.29 (2.25H, s), 1.33 (0.75H, s), 1.38 (9H, s), 1.43 (9H, s), 1.47-1.69 (6H, m), 1.75-1.90 (4H, m), 2.05-2.12 (2H, m), 2.61-2.70 (2H, m), 2.80-2.88 (1H, m), 3.04-3.17 (2H, m), 3.81 (0.75H, tt, J=12.2, 3.9 Hz), 3.93 (0.25H, m), 4.74 (1H, br), 6.70 (0.25H, s), 6.72 (0.75H, s), 7.44 (0.25H, s), 7.45 (0.75H, s).

[Step 2] 5-Amino-2-{[1-(4-hydroxy-4-methylcyclohexyl)-1H-imidazol-4-yl]methyl}valeric acid

[Formula 99]

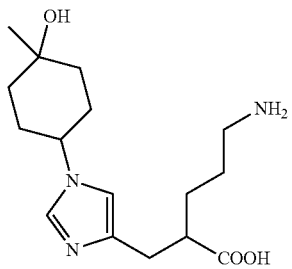

To the compound (306 mg) obtained in Step 1 of this Example, 2 N hydrochloric acid (5 mL) was added, and the mixture was stirred at 40° C. for 3 hours and at 55° C. for 5 hours. After cooling, the solvent was distilled off under reduced pressure. The obtained crude hydrochloride was dissolved in water, and DOWEX 50WX8-200 was added thereto. The resin was washed with water, followed by elution with 4% ammonia water. The eluate was concentrated, and the crude product was washed with acetone to obtain a diastereomeric mixture of the title compound (50 mg, trans:cis=1:3).

$^1$H-NMR (CDCl$_3$) δ: 1.23 (2.25H, s), 1.31 (0.75H, s), 1.47-1.90 (10H, m), 1.97-2.11 (2H, m), 2.46-2.59 (2H, m), 2.83-2.95 (3H, m), 3.97 (0.75H, tt, J=12.2, 3.9 Hz), 4.04 (0.25H, m), 6.97 (0.25H, s), 6.99 (0.75H, s), 7.63 (0.25H, s), 7.64 (0.75H, s).

HRMS (ESI): m/z calcd for C$_{16}$H$_{28}$N$_3$O$_3$: 310.2131 [M+H]$^+$. found: 310.2123.

Example 9

5-Amino-2-{[1-(3-methylcyclohexyl)-1H-imidazol-4-yl]methyl}valeric acid

[Formula 100]

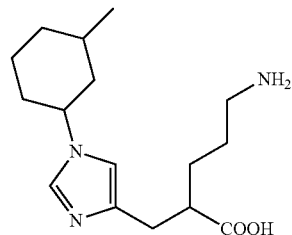

The title compound (10 mg) was obtained in the same way as in Example 6 using 3-methylcyclohexanol (1.84 g) instead of (1R,3R,5S)-bicyclo[3.1.0]hexan-3-ol.

$^1$H-NMR (CD$_3$OD) δ: 1.05 (3H, d, J=6.8 Hz), 1.32-1.40 (1H, m), 1.47-1.55 (1H, m), 1.55-1.76 (7H, m), 1.78-1.87 (1H, m), 1.90-2.05 (3H, m), 2.46-2.58 (2H, m), 2.84-2.95 (3H, m), 4.24 (1H, m), 6.96 (1H, s), 7.57 (1H, s).

HRMS (ESI): m/z calcd for C$_{16}$H$_{28}$N$_3$O$_2$: 294.21815 [M+H]$^+$. found: 294.21898.

Example 10

5-Amino-2-[(1-cycloheptyl-1H-imidazol-4-yl)methyl]valeric acid

[Formula 101]

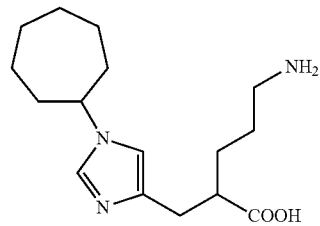

The title compound (30 mg) was obtained in the same way as in Steps 1 and 3 of Example 1 using bromocycloheptane (890 mg) instead of 3-bromocyclohexene.

$^1$H-NMR (CD$_3$OD) δ: 1.46-1.74 (10H, m), 1.74-1.88 (2H, m), 1.85-1.94 (2H, m), 1.99-2.08 (2H, m), 2.45-2.58 (2H, m), 2.82-2.95 (3H, m), 4.16 (1H, m), 6.93 (1H, s), 7.57 (1H, s).

HRMS (ESI): m/z calcd for C$_{16}$H$_{28}$N$_3$O$_2$: 294.21815 [M+H]$^+$. found: 294.21863.

Example 11

5-Amino-2-({1-[exo-bicyclo[2.2.1]hept-2-yl]-1H-imidazol-4-yl}methyl)valeric acid

[Formula 102]

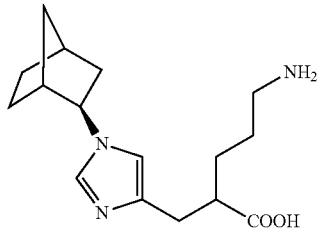

The title compound (0.19 g) was obtained from the compound (0.21 g) obtained in Reference Example 10 in the same way as in Example 3.

$^1$H-NMR (CD$_3$OD) δ: 1.21-1.37 (3H, m), 1.46-1.71 (7H, m), 1.77-1.84 (1H, m), 1.90-1.97 (1H, m), 2.38-2.45 (2H, m), 2.45-2.57 (2H, m), 2.83-2.95 (3H, m), 4.04-4.10 (1H, m), 6.93 (1H, s), 7.56 (1H, s).

HRMS (ESI): m/z calcd for C$_{16}$H$_{26}$N$_3$O$_2$: 292.20250 [M+H]$^+$. found: 292.20319.

Example 12

5-Amino-2-([1-[endo-bicyclo[2.2.1]hept-2-yl]-1H-imidazol-4-yl]methyl)valeric acid

[Formula 103]

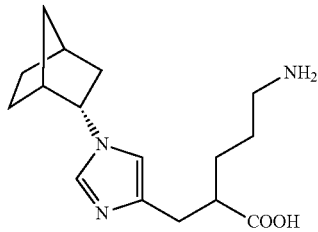

The title compound (0.07 g) was obtained from the compound (0.17 g) obtained in Reference Example 11 in the same way as in Example 3.

$^1$H-NMR (CD$_3$OD) δ: 1.15-1.23 (1H, m), 1.33-1.43 (2H, m), 1.44-1.55 (2H, m), 1.55-1.71 (6H, m), 2.10-2.18 (1H, m), 2.33-2.37 (1H, m), 2.46-2.59 (3H, m), 2.83-2.95 (3H, m), 4.43-4.50 (1H, m), 6.93 (1H, s), 7.57 (1H, s).

HRMS (ESI): m/z calcd for C$_{16}$H$_{26}$N$_3$O$_2$: 292.20250 [M+H]$^+$. found: 292.20252.

Example 13

2-[(1-Adamantan-2-yl-1H-imidazol-4-yl)methyl]-5-aminovaleric acid

[Formula 104]

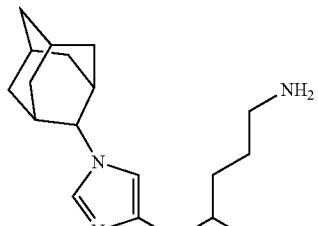

The title compound (0.04 g) was obtained from the compound (0.15 g) obtained in Reference Example 12 in the same way as in Example 3.

$^1$H-NMR (CD$_3$OD) δ: 1.48-1.57 (1H, m), 1.58-1.72 (5H, m), 1.77-1.86 (5H, m), 1.92-1.99 (3H, m), 2.01-2.07 (2H, m), 2.48-2.61 (4H, m), 2.85-2.95 (3H, m), 4.17 (1H, s), 7.03 (1H, s), 7.65 (1H, s).

HRMS (ESI): m/z calcd for C$_{19}$H$_{30}$N$_3$O$_2$: 332.23380 [M+H]$^+$. found: 332.23325.

Example 14

5-Amino-2-{[1-(trans-4-phenoxycyclohexyl)-1H-imidazol-4-yl]methyl}valeric acid

[Formula 105]

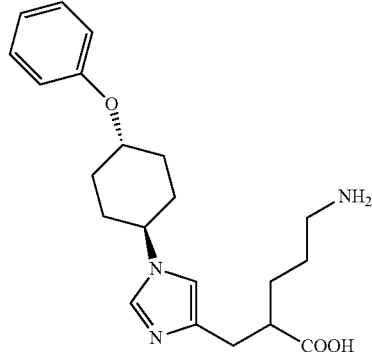

The title compound (7 mg) was obtained from the compound (0.07 g) obtained in Reference Example 13 in the same way as in Example 3.

$^1$H-NMR (CD$_3$OD) δ: 1.47-1.73 (6H, m), 1.84-1.95 (2H, m), 2.08-2.16 (2H, m), 2.21-2.28 (2H, m), 2.46-2.59 (2H, m), 2.84-2.95 (3H, m), 4.09 (1H, m), 4.36 (1H, m), 6.88-6.95 (3H, m), 6.97 (1H, s), 7.23-7.28 (2H, m), 7.59 (1H, s).

HRMS (ESI): m/z calcd for C$_{21}$H$_{30}$N$_3$O$_3$: 372.22872 [M+H]$^+$. found: 372.22850.

Example 15

(2R)-5-Amino-2-{[1-(trans-4-methylcyclohexyl)-1H-imidazol-4-yl]methyl}valeric acid and (2S)-5-amino-2-{([1-(trans-4-methylcyclohexyl)-1H-imidazol-4-yl]methyl}valeric acid

[Step 1] Methyl 5-[(tert-butoxycarbonyl)amino]-2-{[1-(trans-4-methylcyclohexyl)-1H-imidazol-4-yl]methyl}valerate

[Formula 106]

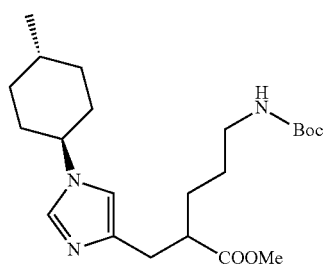

The compound (300 mg) obtained in Reference Example 4 and the compound (860 mg) obtained in Reference Example 3 were suspended in cyclohexane (10 mL). To the suspension, a solution of piperidine (0.154 mL) and propionic acid (0.116 mL) in cyclohexane (10 mL) was added, and the mixture was heated to reflux for 48 hours. After cooling, to the reaction solution, aqueous potassium carbonate was added, and organic matter was extracted with ethyl acetate. The organic layer was washed with saturated sodium chloride solution, then dried over anhydrous sodium sulfate, and filtered, and the solvent was distilled off under reduced pressure. The obtained crude product was dissolved in ethanol (12 mL). To the solution, 10% palladium-carbon catalyst (hydrated, 250 mg) was added, and the mixture was stirred under a hydrogen atmosphere at normal pressure at room temperature for 4 hours and at 60° C. for 2.5 hours. After filtration through celite, the filtrate was concentrated under reduced pressure to obtain a crude product. This crude product was purified by silica gel column chromatography (eluting solvent: hexane/ethyl acetate=2/1-1/3) to obtain the title compound (562 mg).

$^1$H-NMR (CDCl$_3$) δ: 0.94 (3H, d, J=6.6 Hz), 1.02-1.15 (2H, m), 1.34-1.69 (7H, m), 1.43 (9H, s), 1.80-1.87 (2H, m), 1.99-2.09 (2H, m), 2.69 (1H, dd, J=13.7, 6.3 Hz), 2.79 (1H, m), 2.88 (1H, dd, J=13.7, 7.4 Hz), 3.03-3.13 (2H, m), 3.63 (3H, s), 3.79 (1H, tt, J=12.1, 3.9 Hz), 4.76 (1H, br), 6.67 (1H, s), 7.47 (1H, s).

[Step 2] Methyl (2R)-5-[(tert-butoxycarbonyl)amino]-2-{[1-(trans-4-methylcyclohexyl)-1H-imidazol-4-yl]methyl}valerate and methyl (2S)-5-[(tert-butoxycarbonyl)amino]-2-{[1-(trans-4-methylcyclohexyl)-1H-imidazol-4-yl]methyl}valerate

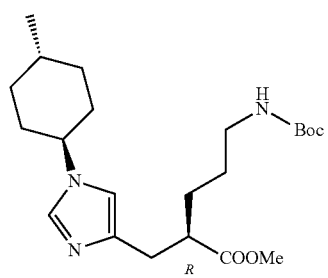

[Formula 107]

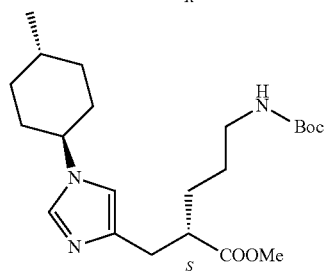

The compound (40 mg) obtained in Step 1 of this Example was dissolved in hexane (1.5 mL) and ethanol (0.5 mL) and optically resolved by high-performance liquid chromatography using CHIRALPAK IA semi-prep column (2.0 cm×25.0 cm). Flow rate: 15 mL/min, eluting solvent: hexane/ethanol=75/25, detection wavelength: 220 nm.

The solvent of the eluate containing optically active compound was distilled off under reduced pressure to respectively obtain each enantiomer (15 mg). Both of the enantiomers were confirmed by analytical high-performance liquid chromatography to be optically pure compounds. Colum: CHIRALPAK IA (0.46 cm×25.0 cm), flow rate: 1 mL/min, eluting solvent: hexane/ethanol=80/20<v/v>, detection wavelength: 220 nm, retention time: methyl (2R)-5-[(tert-butoxycarbonyl)amino]-2-{[1-(trans-4-methylcyclohexyl)-1H-imidazol-4-yl]methyl}valerate (7.2 minutes), methyl (2S)-5-[(tert-butoxycarbonyl)amino]-2-{[1-(trans-4-methylcyclohexyl)-1H-imidazol-4-yl]methyl}valerate (11.2 minutes).

[Step 3] (2R)-5-Amino-2-{[1-(trans-4-methylcyclohexyl)-1H-imidazol-4-yl]methyl}valeric acid

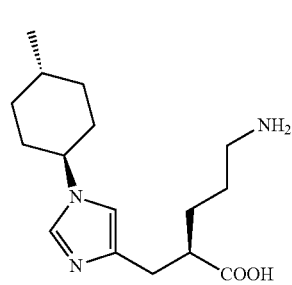

[Formula 108]

To the methyl (2R)-5-[(tert-butoxycarbonyl)amino]-2-{[1-(trans-4-methylcyclohexyl)-1H-imidazol-4-yl]methyl}valerate (15.0 mg) obtained in Step 2 of this Example, 5 N hydrochloric acid (2 mL) was added, and the mixture was heated to reflux for 4 hours. After cooling, the solvent was distilled off under reduced pressure. The obtained crude hydrochloride was dissolved in methanol, and DOWEX 50WX8-200 was added thereto. The resin was washed with water, followed by elution with 4% ammonia water. The eluate was concentrated, and the crude product was washed with acetone to obtain the title compound (2.2 mg).

[Step 4] (2S)-5-Amino-2-{[1-(trans-4-methylcyclohexyl)-1H-imidazol-4-yl]methyl}valeric acid

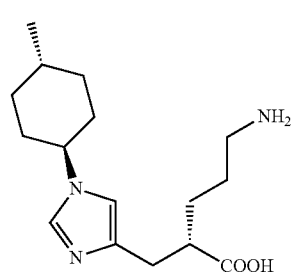

[Formula 109]

To the methyl (2S)-5-[(tert-butoxycarbonyl)amino]-2-{[1-(trans-4-methylcyclohexyl)-1H-imidazol-4-yl]methyl}valerate (15.0 mg) obtained in Step 2 of this Example, 5 N hydrochloric acid (2 mL) was added, and the mixture was heated to reflux for 4 hours. After cooling, the solvent was distilled off under reduced pressure. The obtained crude hydrochloride was dissolved in methanol, and DOWEX 50WX8-200 (200 mg) was added thereto. The resin was washed with water, followed by elution with ammonia water (4%, 80 mL). The eluate was concentrated, and the crude product was washed with acetone to obtain the title compound (1.8 mg).

Example 16

Benzyl 5-amino-2-{[1-(trans-4-methylcyclohexyl)-1H-imidazol-4-yl]methyl}valerate hydrochloride

[Step 1] 5-[(tert-Butoxycarbonyl)amino]-2-{[1-(trans-4-methylcyclohexyl)-1H-imidazol-4-yl]methyl}valeric acid

[Formula 110]

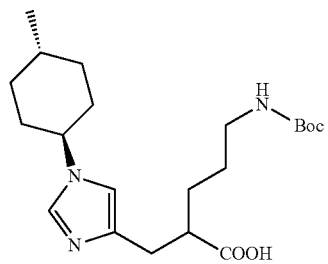

The compound (7.00 g) obtained in Step 1 of Example 15 was dissolved in a mixed solvent of tetrahydrofuran (70 mL) and water (14 mL). To the solution, lithium hydroxide monohydrate (1.26 g) was added at room temperature, and the mixture was stirred overnight. The reaction solution was neutralized by the addition of 2 N hydrochloric acid (8.6 mL), and the solvent was distilled off under reduced pressure. To the obtained residue, methylene chloride was added, and the mixture was dried over anhydrous sodium sulfate. The solvent was distilled off under reduced pressure to obtain a crude product of the title compound. This crude product was directly used in the next reaction.

MS (ESI) m/z 394 (M+H)$^+$.

[Step 2] Benzyl 5-[(tert-butoxycarbonyl)amino]-2-{[1-(trans-4-methylcyclohexyl-1H-imidazol-4-yl]methyl}valerate

[Formula 111]

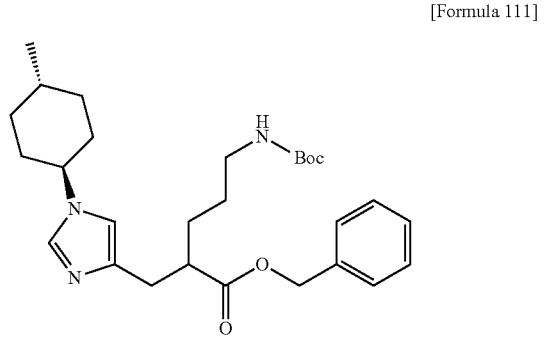 [SMILES: CC(C)(C)OC(=O)NCCCC(Cc1cn([C@H]2CC[C@H](C)CC2)cn1)C(=O)OCc1ccccc1]

The 5-[(tert-butoxycarbonyl)amino]-2-{[1-(trans-4-methylcyclohexyl)-1H-imidazol-4-yl]methyl}valeric acid obtained in Step 1 of this Example was dissolved in methylene chloride (150 mL). To the solution, benzyl alcohol (8.85 mL), 1-ethyl-3-(3-dimethylaminopropyl)carbodiimide hydrochloride (4.95 g), and 4-dimethylaminopyridine (3.15 g) were added at room temperature, and the mixture was stirred for 18 hours. Organic matter was extracted with methylene chloride and dried over anhydrous sodium sulfate, and the solvent was then distilled off under reduced pressure. The obtained crude product was purified by silica gel column chromatography (eluting solvent: hexane/ethyl acetate=7/3-ethyl acetate) to obtain the title compound (8.45 g).

$^1$H-NMR (CDCl$_3$) δ: 0.94 (3H, d, J=6.3 Hz), 1.01-1.13 (2H, m), 1.38-1.72 (16H, m), 1.79-1.86 (2H, m), 1.97-2.04 (2H, m), 2.71 (1H, dd, J=14.1, 5.9 Hz), 2.80-2.87 (1H, m), 2.91 (1H, dd, J=14.1, 7.8 Hz), 3.07 (2H, br s), 3.68-3.76 (1H, m), 4.68 (1H, br s), 5.10 (2H, s), 6.57 (1H, s), 7.29-7.40 (6H, m).

MS (ESI) m/z 484 (M+H)$^+$

[Step 3] Benzyl 5-amino-2-{[1-(trans-4-methylcyclohexyl)-1H-imidazol-4-yl]methyl}valerate hydrochloride

[Formula 112]

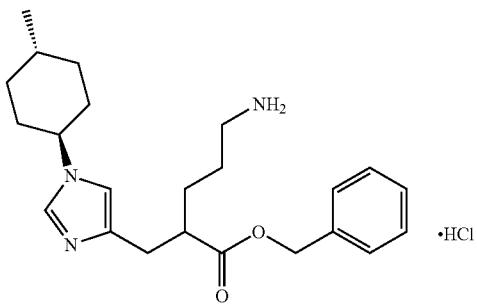

The benzyl 5-[(tert-butoxycarbonyl)amino]-2-{[1-(trans-4-methylcyclohexyl-1H-imidazol-4-yl]methyl}valerate obtained in Step 2 of this Example was dissolved in 1,4-dioxane (40 mL). To the solution, a solution of 4 N hydrochloric acid in 1,4-dioxane (40 mL) was added dropwise at room temperature, and the mixture was then stirred for 24 hours. The solvent in the reaction solution was distilled off under reduced pressure to obtain a crude product of the title compound (8.04 g).

$^1$H-NMR (CD$_3$OD) δ: 0.97 (3H, d, J=6.7 Hz), 1.11-1.22 (2H, m), 1.43-1.54 (1H, m), 1.62-1.89 (8H, m), 1.99-2.06 (2H, m), 2.88-3.04 (5H, m), 4.10 (1H, tt, J=12.1, 3.9 Hz), 5.07 (1H, d, J=12.1 Hz), 5.15 (1H, d, J=12.1 Hz), 7.28-7.37 (6H, m), 8.82 (1H, d, J=1.6 Hz).

MS (ESI) m/z 384 (M+H)$^+$

Example 17

2-{[1-(trans-4-Methylcyclohexyl)-1H-imidazol-4-yl]methyl}-5-(L-phenylalanylamino)valeric acid

[Step 1] Benzyl 5-({N-[(benzyloxy)carbonyl]-L-phenylalanyl}amino)-2-{[1-(trans-4-methylcyclohexyl)-1H-imidazol-4-yl]methyl}valerate

[Formula 113]

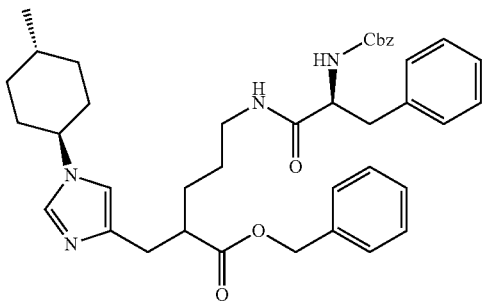

The compound (200 mg) obtained in Example 16 was dissolved in N,N-dimethylformamide (6 mL). To the solution, N-[(benzyloxy)carbonyl]-L-phenylalanine (197 mg), 4-(4,6-dimethoxy-1,3,5-triazin-2-yl)-4-methylmorpholinium chloride hydrate (DMT-MM, 90%, 182 mg), and triethylamine (135 μl) were added at room temperature, and the mixture was stirred for 3 days. To the reaction solution, ethyl acetate was added, and the mixture was washed three times with 10% sodium chloride solution and subsequently washed with saturated aqueous sodium bicarbonate. The obtained organic layer was dried over anhydrous sodium sulfate, and the solvent was distilled off under reduced pressure. The obtained crude product was purified by silica gel column chromatography (eluting solvent: hexane/ethyl acetate=1/1-ethyl acetate) to obtain the title compound (254 mg).

$^1$H-NMR (CDCl$_3$) δ: 0.94 (3H, d, J=6.7 Hz), 1.07 (2H, q, J=12.9 Hz), 1.43-1.55 (7H, m), 1.80-1.84 (2H, m), 1.97-1.99 (2H, m), 2.67-2.88 (3H, m), 3.08-3.15 (3H, m), 3.68-3.70 (0.5H, m), 4.40-4.41 (0.5H, m), 5.05-5.10 (4H, m), 5.60-5.63 (1H, m), 6.54-6.56 (2H, m), 7.16-7.21 (4H, m), 7.29-7.52 (7H, m).

MS (ESI) m/z 665 (M+H)$^+$.

[Step 2] 2-{[1-(trans-4-Methylcyclohexyl)-1H-imidazol-4-yl]methyl}-5-(L-phenylalanylamino)valeric acid

[Formula 114]

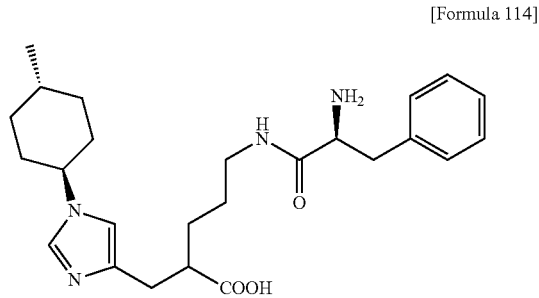 [SMILES: C[C@H]1CC[C@H](n2cnc(CC(CCCNC(=O)[C@@H](N)Cc3ccccc3)C(=O)O)c2)CC1]

The compound obtained in Step 1 of this Example was dissolved in ethanol (8 mL). To the solution, 10% palladium-carbon catalyst (hydrated, 85 mg) was added, and the mixture was stirred at room temperature for 5 hours under a hydrogen atmosphere at normal pressure. The solvent in the reaction solution was distilled off under reduced pressure, and the residue was purified by preparative reverse-phase HPLC to obtain the title compound (128 mg).

$^1$H-NMR (CDCl$_3$) δ: 0.95 (3H, d, J=6.7 Hz), 1.07-1.14 (2H, m), 1.41-1.44 (2H, m), 1.59-1.72 (5H, m), 1.84-1.88 (2H, m), 2.07-2.11 (2H, m), 2.71-2.80 (4H, m), 3.23-3.25 (3H, m), 3.62-3.65 (1H, m), 3.82-3.83 (1H, m), 6.75 (1H, s), 7.23-7.30 (5H, m).

HRMS (ESI): m/z calcd for C$_{25}$H$_{37}$N$_4$O$_3$: 441.28656 [M+H]$^+$. found: 441.28690.

Example 18

2-{[1-(trans-4-Methylcyclohexyl)-1H-imidazol-4-yl]methyl}-5-(L-norleucylamino)valeric acid

[Step 1] Benzyl 5-({N-[(benzyloxy)carbonyl]-L-norleucyl}amino)-2-{[1-(trans-4-methylcyclohexyl)-1H-imidazol-4-yl]methyl}valerate

[Formula 115]

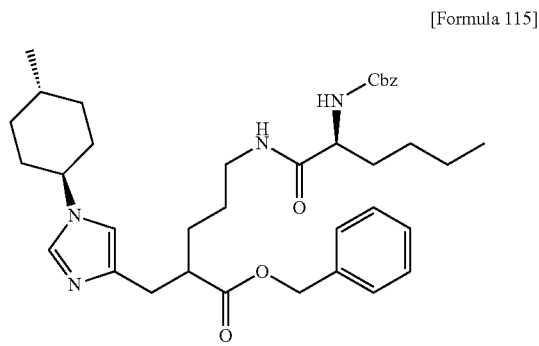 [SMILES: CCCC[C@H](NC(=O)OCc1ccccc1)C(=O)NCCCC(Cc1cn([C@H]2CC[C@H](C)CC2)cn1)C(=O)OCc1ccccc1]

The title compound (244 mg) was obtained from the compound (200 mg) obtained in Example 16 and N—[(benzyloxy)carbonyl]-L-norleucine (174 mg) in the same way as in Step 1 of Example 17.

$^1$H-NMR (CDCl$_3$) δ: 0.83-0.88 (3H, m), 0.94 (3H, d, J=6.7 Hz), 1.02-1.12 (2H, m), 1.23-1.74 (12H, m), 1.78-1.85 (2H, m), 1.96-2.02 (2H, m), 2.73-2.95 (3H, m), 3.17-3.32 (2H, m), 3.67-3.76 (1H, m), 4.10-4.18 (1H, m), 5.09-5.11 (4H, m), 5.55-5.58 (1H, m), 6.55 (0.5H, s), 6.57 (0.5H, s), 6.84-6.93 (1H, m), 7.36-7.30 (9H, m), 7.51 (1H, s).

[Step 2] 2-{[1-(trans-4-Methylcyclohexyl)-1H-imidazol-4-yl]methyl}-5-(L-norleucylamino)valeric acid

[Formula 116]

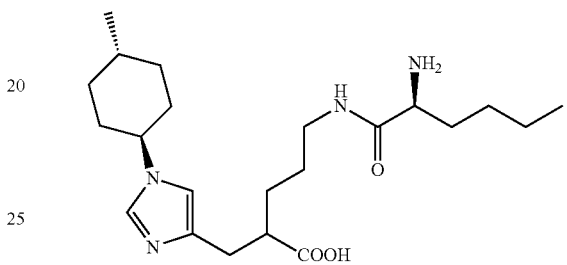

The title compound (124 mg) was obtained from the compound (244 mg) obtained in Step 1 of this Example in the same way as in Step 2 of Example 17.

$^1$H-NMR (CDCl$_3$) δ: 0.84-0.89 (3H, m), 0.94 (3H, d, J=6.3 Hz), 1.04-1.14 (2H, m), 1.26-1.68 (13H, m), 1.79-1.87 (2H, m), 2.03-2.10 (2H, m), 2.58-2.69 (2H, m), 2.85 (1H, dd, J=14.5, 7.4 Hz), 3.11-3.27 (2H, m), 3.45-3.52 (1H, m), 3.77-3.83 (1H, m), 6.72 (1H, s), 7.52 (1H, s), 8.03 (1H, br s).

HRMS (ESI): m/z calcd for C$_{22}$H$_{39}$N$_4$O$_3$: 407.30221 [M+H]$^+$. found: 407.30257.

Example 19

(2S)-2-{[1-(trans-4-Methylcyclohexyl)-1H-imidazol-4-yl]methyl}-5-({[(5-methyl-2-oxo-1,3-dioxol-4-yl)methoxy]carbonyl}amino)valeric acid

[Formula 117]

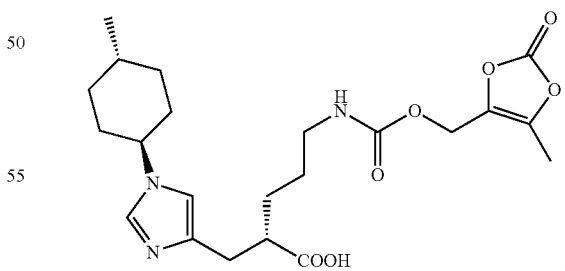

The compound (200 mg) obtained in Step 4 of Example 15 was dissolved in a mixed solvent of N,N-dimethylformamide (2 mL) and water (1 mL). To the solution, (5-methyl-2-oxo-1,3-dioxol-4-yl)methyl 4-nitrophenyl carbonate (336 mg) (J. Med. Chem., 1996, Vol. 39, p. 480) was added at room temperature, and the mixture was stirred for 4 days. The solvent in the reaction solution was distilled off under reduced pressure, and the residue was then subjected to thin-layer chromatography to obtain the title compound (100 mg).

$^1$H-NMR (CDCl$_3$) δ: 0.96 (3H, d, J=6.5 Hz), 1.08-1.18 (2H, m), 1.40-1.51 (2H, m), 1.55-1.78 (5H, m), 1.82-1.90 (2H, m), 2.07-2.15 (2H, m), 2.18 (3H, s), 2.70-2.84 (3H, m), 3.13-3.20 (2H, m), 3.86-3.95 (1H, m), 4.79 (2H, s), 5.18 (1H, br s), 6.78 (1H, s), 7.74 (1H, s).

HRMS (ESI): m/z calcd for C$_{22}$H$_{32}$N$_3$O$_7$: 450.22402 [M+H]$^+$. found: 450.22369.

Example 20

(2S)-5-({[1-(Isobutyryloxy)ethoxy]carbonyl}amino)-2-{[1-(trans-4-methylcyclohexyl)-1H-imidazol-4-yl]methyl}valeric acid

[Step 1] 1-[(Chlorocarbonyl)oxy]ethyl 2-methylpropionate

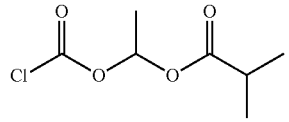

[Formula 118]

1-{[(Ethylthio)carbonyl]oxy}ethyl 2-methylpropionate (WO2005/66122) (412 mg) was cooled to −30° C. Sulfuryl chloride (157 μl) was added thereto, and the mixture was then stirred for 45 minutes. The solvent in the reaction solution was distilled off under reduced pressure to obtain a crude product of the title compound.

[Step 2] (2S)-5-({[1-(Isobutyryloxy)ethoxy]carbonyl}amino)-2-{[1-(trans-4-methylcyclohexyl)-1H-imidazol-4-yl]methyl}valeric acid

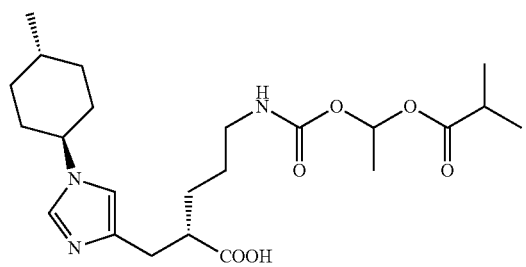

[Formula 119]

The compound (500 mg) obtained in Step 4 of Example 15 was dissolved in a mixed solvent of N,N-dimethylformamide (6 mL) and water (2 mL). To the solution, a solution of the compound obtained in Step 1 of this Example in methylene chloride (1 mL) was added at 0° C., and the mixture was stirred for 3 days. The solvent in the reaction solution was distilled off under reduced pressure, and organic matter was extracted three times with an ethyl acetate-methanol mixed solvent (95:5). The organic layer was dried over anhydrous sodium sulfate, and the solvent was then distilled off under reduced pressure to obtain a crude product. This crude product was purified by silica gel column chromatography (eluting solvent: ethyl acetate-methylene chloride/methanol=95/5), and the obtained solid was further washed with water to obtain the title compound of interest (97 mg).

$^1$H-NMR (CDCl$_3$) δ: 0.96 (3H, d, J=6.3 Hz), 1.07-1.13 (2H, m), 1.16 (6H, d, J=7.0 Hz), 1.41-1.49 (5H, m), 1.57-1.78 (5H, m), 1.84-1.90 (2H, m), 2.08-2.14 (2H, m), 2.53 (1H, tt, J=7.0, 7.0 Hz), 2.70-2.85 (3H, m), 3.12-3.20 (2H, m), 3.84-3.92 (1H, m), 4.96 (1H, br s), 6.76-6.80 (2H, m), 7.71 (1H, s).

HRMS (ESI): m/z calcd for C$_{23}$H$_{38}$N$_3$O$_6$: 452.27606 [M+Na]$^+$. found: 452.27610.

Example 21

1-[(Isopropoxycarbonyl)oxy]ethyl (2S)-5-({[1-(isobutyryloxy)ethoxy]carbonyl}amino)-2-{[1-(trans-4-methylcyclohexyl)-1H-imidazol-4-yl]methyl}valerate

[Step 1] 1-Iodoethyl isopropyl carbonate

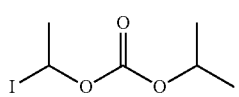

[Formula 120]

To a solution of 1-chloroethyl isopropyl carbonate (1.00 g) in toluene (30 mL), sodium iodide (2.10 g) and 18-crown-6 (185 mg) were added at room temperature, and the mixture was stirred at 100° C. for 5 hours. To the reaction solution, ethyl acetate was added, and the mixture was washed with water and 5% aqueous sodium thiosulfate in this order and then dried over anhydrous sodium sulfate. The solvent was distilled off under reduced pressure to obtain a crude product of the title compound (1.51 g).

$^1$H-NMR (CDCl$_3$) δ: 1.32 (3H, d, J=6.3 Hz), 1.34 (3H, d, J=6.3 Hz), 2.24 (3H, d, J=5.9 Hz), 4.95 (1H, tt, J=6.3, 6.3 Hz), 6.76 (1H, q, J=5.9 Hz).

[Step 2] 1-[(Isopropoxycarbonyl)oxy]ethyl (2S)-5-({[1-(isobutyryloxy)ethoxy]carbonyl}amino)-2-{[1-(trans-4-methylcyclohexyl)-1H-imidazol-4-yl]methyl}valerate

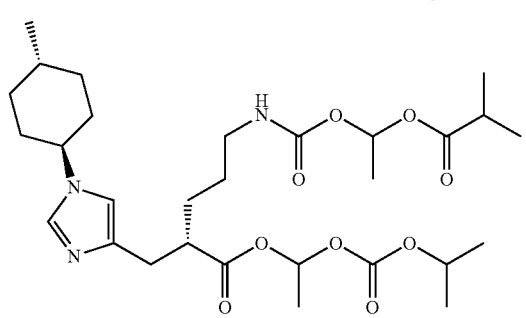

[Formula 121]

The compound (97 mg) obtained in Example 20 was dissolved in a mixed solvent of tetrahydrofuran (1 mL) and water (1 mL). To the solution, sodium bicarbonate (18 mg) was added, and the mixture was stirred at room temperature for 3.5 hours. The solvent in the reaction solution was distilled off under reduced pressure. The obtained residue was dissolved in N,N-dimethylformamide (3 mL), and the compound (74 mg) obtained in Step 1 of this Example was added thereto at 0° C. Three days later, the compound (25 mg) obtained in Step 1 of this Example and sodium bicarbonate (6 mg) were added thereto, and the mixture was further stirred for 20 hours. The solvent in the reaction solution was distilled off under reduced pressure, and the residue was then purified by silica gel column chromatography (eluting solvent: ethyl acetate-methylene chloride/methanol=90/10). The obtained crude product was again purified by silica gel column chromatography (eluting solvent: ethyl acetate) to obtain the title compound (43 mg).

$^1$H-NMR (CDCl$_3$) δ: 0.95 (3H, d, J=6.3 Hz), 1.05-1.17 (8H, m), 1.30-1.32 (6H, m), 1.42-1.69 (13H, m), 1.82-1.87 (2H, m), 2.05-2.11 (2H, m), 2.49-2.56 (1H, m), 2.68-2.96 (3H, m), 3.10-3.23 (2H, m), 3.76-3.85 (1H, m), 4.85-4.92 (1H, m), 5.23 (0.5H, br s), 5.31 (0.5H, br s), 6.68-6.73 (2H, m), 6.79 (1H, q, J=5.5 Hz), 7.45 (0.5H, s), 7.46 (0.5H, s).

HRMS (ESI): m/z calcd for C$_{29}$H$_{48}$N$_3$O$_9$: 582.33905 [M+H]+. found: 582.33901.

Example 22

(2S)-5-({[1-(2,2-Dimethylpropanoyloxy)ethoxy]carbonyl}amino)-2-{[1-(trans-4-methylcyclohexyl)-1H-imidazol-4-yl]methyl}valeric acid

[Step 1] S-Ethyl O-(1-iodoethyl)thiocarbonate

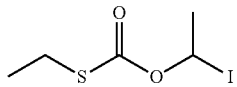

[Formula 122]

O-(1-Chloroethyl) S-ethyl thiocarbonate (Synthesis, 1986, Vol. 8, p. 627) (5.0 g) was dissolved in toluene (100 mL). To the solution, sodium iodide (11.6 g) and 18-crown-6 (2.35 g) were added at room temperature, and the mixture was stirred at 100° C. for 4 hours. The reaction solution was cooled to room temperature. Ethyl acetate was added thereto, and the mixture was washed twice with a 5% aqueous sodium thiosulfate. The organic layer was dried over anhydrous sodium sulfate, and the solvent was then distilled off under reduced pressure to obtain a crude product of the title compound. This crude product was directly used in the next reaction.

$^1$H-NMR (CDCl$_3$) δ: 1.31 (3H, t, J=7.4 Hz), 2.18 (3H, d, J=6.3 Hz), 2.84-2.91 (2H, m), 6.89 (1H, q, J=6.3 Hz).

[Step 2] 1-{[(Ethylthio)carbonyl]oxy}ethyl pivalate

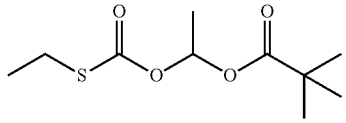

[Formula 123]

Pivalic acid (3.02 g) was dissolved in a mixed solvent of methylene chloride (100 mL) and water (50 mL). To the solution, tetrabutylammonium bisulfate (10.0 g) and sodium bicarbonate (4.97 g) were added in this order under ice cooling, and the mixture was then stirred for 30 minutes. Subsequently, a solution of the compound obtained in Step 1 of this Example in methylene chloride (5 mL) was added thereto, and the mixture was stirred at room temperature for 6 days. The organic layer was separated and dried over anhydrous sodium sulfate, and the solvent was distilled off under reduced pressure. The obtained residue was purified by silica gel column chromatography (eluting solvent: hexane-hexane/ethyl acetate=95/5) to obtain the title compound (2.62 g).

$^1$H-NMR (CDCl$_3$) δ: 1.20 (9H, s), 1.31 (3H, t, J=7.4 Hz), 1.50 (3H, d, J=5.5 Hz), 2.84-2.90 (2H, m), 6.92 (1H, q, J=5.5 Hz).

[Step 3] (2S)-5-({[1-(2,2-Dimethylpropanoyloxy)ethoxy]carbonyl}amino)-2-{[1-(trans-4-methylcyclohexyl)-1H-imidazol-4-yl]methyl}valeric acid

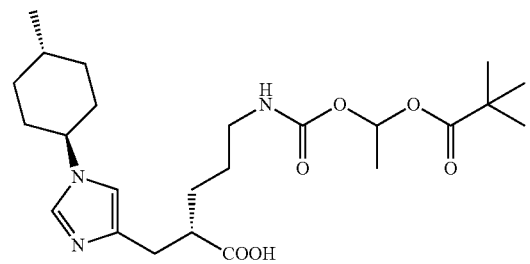

[Formula 124]

The title compound (267 mg) was obtained from the compound obtained in Step 2 of this Example and the compound (500 mg) obtained in Step 4 of Example 15 in the same way as in Steps 1 and 2 of Example 20.

$^1$H-NMR (CDCl$_3$) δ: 0.95 (3H, d, J=6.3 Hz), 1.11-1.19 (11H, m), 1.43-1.76 (10H, m), 1.85-1.92 (2H, m), 2.13-2.19 (2H, m), 2.83-2.94 (2H, m), 2.99-3.08 (1H, m), 3.11-3.21 (2H, m), 4.09-4.17 (1H, m), 5.38 (1H, br s), 6.75 (1H, q, J=5.4 Hz), 7.07 (1H, s), 8.79 (1H, s).

HRMS (ESI): m/z calcd for C$_{24}$H$_{40}$N$_3$O$_6$: 466.29171 [M+H]$^+$. found: 466.29083.

Example 23

(2S)-5-{([1-[(Cyclohexylcarbonyl)oxy]ethoxy}carbonyl)amino]-2-{[1-(trans-4-methylcyclohexyl)-1H-imidazol-4-yl]methyl}valeric acid

[Step 1] 1-{[(Ethylthio)carbonyl]oxy}ethyl cyclohexanecarboxylate

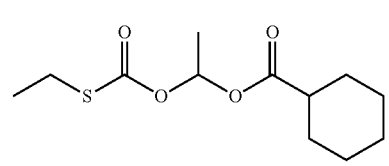

[Formula 125]

The title compound (1.62 g) was obtained from O-(1-chloroethyl) S-ethyl thiocarbonate (4.0 g) and cyclohexanecarboxylic acid (3.04 g) in the same way as in Steps 1 and 2 of Example 22.

$^1$H-NMR (CDCl$_3$) δ: 1.20-1.28 (3H, m), 1.31 (3H, t, J=7.4 Hz), 1.39-1.48 (2H, m), 1.49 (3H, d, J=5.5 Hz), 1.60-1.66

(1H, m), 1.73-1.77 (2H, m), 1.86-1.93 (2H, m), 2.37-2.27 (1H, m), 2.92-2.82 (2H, m), 6.94 (1H, q, J=5.5 Hz).

[Step 2] (2S)-5-[({1-[(Cyclohexylcarbonyl)oxy]ethoxy}carbonyl)amino]-2-{[1-(trans-4-methylcyclohexyl)-1H-imidazol-4-yl]methyl}valeric acid

[Formula 126]

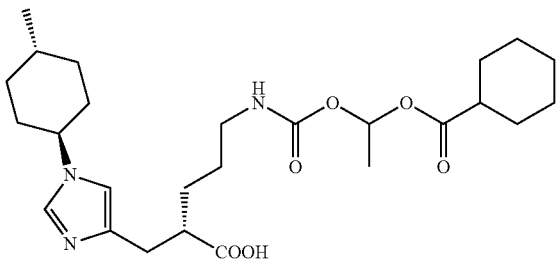

The title compound (318 mg) was obtained from the compound obtained in Step 1 of this Example and the compound (400 mg) obtained in Step 4 of Example 15 in the same way as in Steps 1 and 2 of Example 20.

$^1$H-NMR (CDCl$_3$) δ: 0.96 (3H, d, J=6.7 Hz), 1.07-1.31 (5H, m), 1.39-1.47 (7H, m), 1.57-1.78 (8H, m), 1.84-1.92 (4H, m), 2.07-2.14 (2H, m), 2.28 (1H, tt, J=11.2, 3.6 Hz), 2.68-2.84 (3H, m), 3.12-3.21 (2H, m), 3.86 (1H, tt, J=12.1, 3.7 Hz), 4.95 (1H, br s), 6.76 (1H, s), 6.78 (1H, q, J=5.7 Hz), 7.63 (1H, s)

HRMS (ESI): m/z calcd for C$_{26}$H$_{42}$N$_3$O$_6$: 492.30736 [M+H]$^+$. found: 492.30677.

Example 24

2-(2-Aminoethoxy)-3-[1-(trans-4-methylcyclohexyl)-1H-imidazol-4-yl]propionic acid

[Step 1] (2Z)-2-{[1-(trans-4-Methylcyclohexyl)-1H-imidazol-4-yl]methylene}morpholin-3-one

[Formula 127]

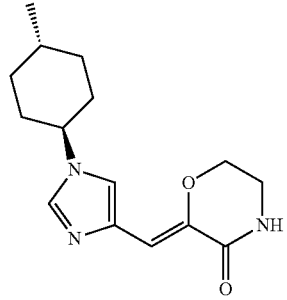

To a solution of tert-butyl 3-oxomorpholine-4-carboxylate (859 mg) in tetrahydrofuran (8 mL), a solution of lithium bis(trimethylsilyl)amide in hexane (1.02 M, 3.00 mL) was added at −78° C., and the mixture was stirred at −78° C. for 30 minutes. To this reaction solution, a solution of the compound (400 mg) obtained in Reference Example 4 in tetrahydrofuran (5 mL) was added at −78° C. The mixture was stirred at −78° C. for 1 hour, then slowly heated to room temperature, and stirred for 14 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: methylene chloride-methylene chloride/methanol=10/1) to obtain the title compound (330 mg).

$^1$H-NMR (CDCl$_3$) δ: 0.92 (3H, d, J=6.6 Hz), 1.08 (2H, m), 1.43 (1H, m), 1.67 (2H, m), 1.84 (2H, m), 2.09 (2H, m), 3.58 (2H, m), 3.85 (1H, tt, J=12.1, 3.9 Hz), 4.24 (2H, m), 6.10 (1H, br), 6.93 (1H, s), 7.35 (1H, s), 7.58 (1H, s).

[Step 2] 2-{[1-(trans-4-Methylcyclohexyl)-1H-imidazol-4-yl]methyl}morpholin-3-one

[Formula 128]

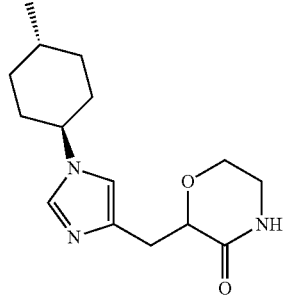

10% palladium-carbon catalyst (hydrated, 300 mg) was suspended in a solution of the compound (330 mg) obtained in Step 1 of this Example in ethanol (8 mL). The suspension was stirred under a hydrogen atmosphere at normal pressure at room temperature for 1 hour and at 45° C. for 1 hour. The reaction solution was filtered through celite, and the filtrate was concentrated. The obtained crude product was purified by silica gel column chromatography (eluting solvent: methylene chloride/methanol=20/1-10/1) to obtain the title compound (325 mg).

$^1$H-NMR (CDCl$_3$) δ: 0.94 (3H, d, J=6.6 Hz), 1.09 (2H, m), 1.44 (1H, m), 1.65 (2H, m), 1.84 (2H, m), 2.09 (2H, m), 3.02 (1H, dd, J=15.2, 9.0 Hz), 3.25-3.32 (2H, m), 3.54 (1H, m), 3.75 (1H, m), 3.80 (1H, tt, J=12.1, 3.9 Hz), 4.03 (1H, m), 4.47 (1H, dd, J=9.0, 3.1 Hz), 6.31 (1H, br), 6.80 (1H, s), 7.45 (1H, s).

[Step 3] 2-(2-Aminoethoxy)-3-[1-(trans-4-methylcyclohexyl)-1H-imidazol-4-yl]propionic acid

[Formula 129]

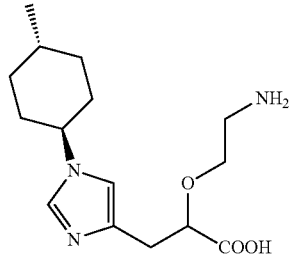

To the compound (300 mg) obtained in Step 2 of this Example, concentrated hydrochloric acid (7 mL) was added, and the mixture was heated to reflux for 8 hours. Then, the solvent was distilled off under reduced pressure. The obtained crude hydrochloride was dissolved in methanol, and DOWEX 50WX8-200 was added thereto. The resin was washed with water, followed by elution with 4% ammonia water. The eluate was concentrated to obtain the title compound (154 mg).

$^1$H-NMR (CD$_3$OD) δ: 0.95 (3H, d, J=6.6 Hz), 1.15 (2H, m), 1.47 (1H, m), 1.72 (2H, m), 1.84 (2H, m), 2.04 (2H, m), 2.83-3.07 (4H, m), 3.58-3.68 (2H, m), 3.90-4.01 (2H, m), 6.98 (1H, s), 7.58 (1H, s).

HRMS (ESI): m/z calcd for C$_{15}$H$_{26}$N$_3$O$_3$: 296.1974 [M+H]$^+$. found: 296.1962.

Example 25

2-[(1R)-2-Amino-1-methylethoxy]-3-[1-(trans-4-methylcyclohexyl)-1H-imidazol-4-yl]propionic acid

[Step 1]
(6R)-4-(Methoxymethyl)-6-methylmorpholin-3-one

[Formula 130]

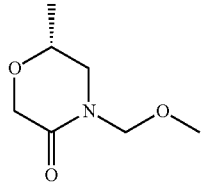

To sodium hydride (63%, 4.4 g, 116 mmol) suspended in tetrahydrofuran (100 mL), a solution of (6R)-6-methylmorpholin-3-one (EP350002) (12.1 g) in tetrahydrofuran (50 mL) was added dropwise over 30 minutes under ice cooling. The mixture was stirred at the same temperature for 30 minutes and then further stirred at room temperature for 30 minutes. A solution of chloromethyl methyl ether (10 mL) in tetrahydrofuran (50 mL) was added dropwise thereto over 30 minutes under ice cooling. The mixture was stirred for 30 minutes under ice cooling and then stirred overnight at room temperature. An appropriate amount of water for partition was added thereto, followed by several extractions with ethyl acetate. The organic layer was dried over anhydrous sodium sulfate. The solvent was distilled off under reduced pressure, and the obtained residue was purified by silica gel column chromatography (eluting solvent: hexane-hexane/ethyl acetate=40/60) to obtain the title compound (7.86 g).

$^1$H-NMR (CDCl$_3$) δ: 1.30 (3H, d, J=5.9 Hz), 3.22-3.34 (5H, m), 3.86-3.95 (1H, m), 4.19 (1H, d, J=16.8 Hz), 4.31 (1H, d, J=16.8 Hz), 4.75 (1H, d, J=9.8 Hz), 4.88 (1H, d, J=9.8 Hz).

[Step 2] (6R)-4-(Methoxymethyl)-6-methyl-2-{[1-(trans-4-methylcyclohexyl)-1H-imidazol-4-yl]methyl}morpholin-3-one

[Formula 131]

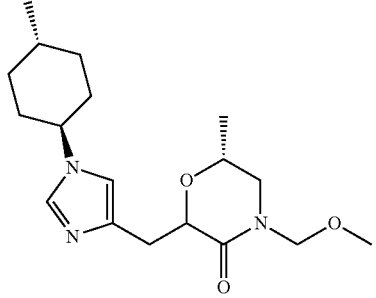

Diisopropylamine (1.05 mL) was dissolved in tetrahydrofuran (10 mL). To the solution, a solution of n-butyllithium in hexane (1.57 M, 4.50 mL) was added at 0° C., and the mixture was stirred at 0° C. for 15 minutes and at room temperature for 5 minutes. The reaction solution was cooled to −78° C. Then, a solution of the compound (1.16 g) obtained in Step 1 of this Example in tetrahydrofuran (5 mL) was added thereto, and the mixture was stirred at −78° C. for 1.5 hours. Then, a solution of the compound (1.00 g) obtained in Reference Example 4 in tetrahydrofuran (5 mL) was added thereto at −78° C. After stirring at −78° C. for 30 minutes, the mixture was heated to room temperature and stirred for 14 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure. The residue was purified by silica gel column chromatography (eluting solvent: methylene chloride/methanol=10/1). The obtained crude product was dissolved in methylene chloride (10 mL). To the solution, triethylamine (1.45 mL) and methanesulfonyl chloride (0.40 mL) were added, and the mixture was stirred at room temperature for 1 hour. To the reaction solution, saturated aqueous ammonium chloride was added, and organic matter was extracted with ethyl acetate. The organic layer was dried over anhydrous sodium sulfate and filtered, and the solvent was distilled off under reduced pressure. The obtained residue was dissolved in tetrahydrofuran (10 mL). To the solution, 1,8-diazabicyclo[5.4.0]undec-7-ene (0.90 mL) was added, and the mixture was stirred at room temperature for 3 hours. To the reaction solution, saturated aqueous ammonium chloride was added, and organic matter was extracted with ethyl acetate. The organic layer was dried over anhydrous sodium sulfate and filtered, and the solvent was distilled off under reduced pressure. The residue was dissolved in ethanol (10 mL), and 10% palladium-carbon catalyst (hydrated, 300 mg) was suspended in the solution. The suspension was stirred at 50° C. for 6 hours under a hydrogen atmosphere at normal pressure. The reaction solution was filtered through celite, and the filtrate was concentrated. The obtained crude product was purified by silica gel column chromatography (eluting solvent: methylene chloride-methylene chloride/methanol=10/1) to obtain the title compound (945 mg).

$^1$H-NMR (CD$_3$OD) δ: 0.95 (3H, d, J=6.6 Hz), 1.15 (2H, m), 1.23 (3H, d, J=6.3 Hz), 1.48 (1H, m), 1.71 (2H, m), 1.84 (2H, m), 2.03 (2H, m), 2.97 (1H, dd, J=15.2, 7.0 Hz), 3.14 (1H, m), 3.18 (3H, s), 3.23-3.38 (2H, m), 3.91-3.99 (2H, m), 4.43 (1H, dd, J=7.4, 3.5 Hz), 4.69 (1H, d, J=10.2 Hz), 4.79 (1H, d, J=10.2 Hz), 6.96 (1H, s), 7.58 (1H, s).

[Step 3] 2-[(1R)-2-Amino-1-methylethoxy]-3-[1-(trans-4-methylcyclohexyl)-1H-imidazol-4-yl]propionic acid

[Formula 132]

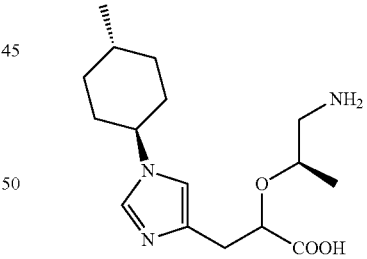

To the compound (100 mg) obtained in Step 2 of this Example, concentrated hydrochloric acid (4 mL) was added, and the mixture was heated to reflux for 20 hours. Then, the solvent was distilled off under reduced pressure. The obtained crude hydrochloride was dissolved in water, and DOWEX 50WX8-200 was added thereto. The resin was washed with water, followed by elution with 4% ammonia water. The eluate was concentrated to obtain the title compound (35 mg).

$^1$H-NMR (CD$_3$OD) δ: 0.93 (3H, d, J=6.3 Hz), 0.95 (3H, d, J=6.8 Hz), 1.16 (2H, m), 1.48 (1H, m), 1.73 (2H, m), 1.84 (2H, m), 2.03 (2H, m), 2.75 (1H, m), 2.77 (1H, dd, J=14.6, 9.8 Hz), 2.95 (1H, m), 3.08 (1H, dd, J=14.6, 3.4 Hz), 3.55 (1H, m), 3.96 (1H, tt, J=12.2, 3.9 Hz), 4.02 (1H, dd, J=9.8, 3.4 Hz), 6.98 (1H, s), 7.59 (1H, s).

HRMS (ESI): m/z calcd for $C_{16}H_{28}N_3O_3$: 310.2131 $[M+H]^+$. found: 310.2131.

Example 26

2-[(3S)-3-Aminopyrrolidin-1-yl]-3-[1-(trans-4-methylcyclohexyl)-1H-imidazol-4-yl]propionic acid

[Step 1] Ethyl 3-[1-(trans-4-methylcyclohexyl)-1H-imidazol-4-yl]propionate

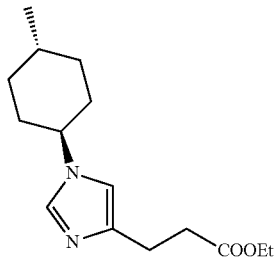

[Formula 133]

Ethyl diethylphosphonoacetate (1.89 g) was dissolved in tetrahydrofuran (15 mL), and sodium hydride (63%, 321 mg) was added thereto at 0° C. After stirring at 0° C. for 1 hour, a solution of the compound (1.20 g) obtained in Reference Example 4 in tetrahydrofuran (6 mL) was added thereto at 0° C., and the mixture was stirred at 0° C. for 1 hour. To the reaction solution, saturated aqueous ammonium chloride was added, and organic matter was extracted with ethyl acetate. The organic layer was washed with water, then dried over anhydrous sodium sulfate, and filtered, and the solvent was distilled off under reduced pressure. The obtained crude product was dissolved in ethanol (20 mL). To the solution, 10% palladium-carbon catalyst (hydrated, 500 mg) was added, and the mixture was stirred at 55° C. for 5 hours under a hydrogen atmosphere at normal pressure. After filtration through celite, the filtrate was concentrated under reduced pressure to obtain a crude product. This crude product was purified by NH silica gel column chromatography (eluting solvent: hexane/ethyl acetate=2/1-1/2) to obtain the title compound (1.06 mg).

$^1$H-NMR (CDCl$_3$) δ: 0.94 (3H, d, J=6.6 Hz), 1.03-1.15 (2H, m), 1.23 (3H, t, J=7.0 Hz), 1.45 (1H, m), 1.57-1.69 (2H, m), 1.80-1.88 (2H, m), 2.03-2.10 (2H, m), 2.66 (2H, t, J=7.4 Hz), 2.88 (2H, t, J=7.4 Hz), 3.79 (1H, tt, J=12.1, 3.9 Hz), 4.13 (2H, q, J=7.0 Hz), 6.70 (1H, s), 7.42 (1H, s).

[Step 2] Ethyl 2-{(3S)-3-[(tert-butoxycarbonyl)amino]pyrrolidin-1-yl}-3-[1-(trans-4-methylcyclohexyl)-1H-imidazol-4-yl]propionate

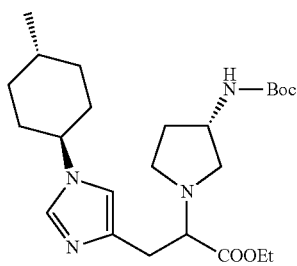

[Formula 134]

To a solution of the compound (400 mg) obtained in Step 1 of this Example in tetrahydrofuran (5 mL), a solution of lithium bis(trimethylsilyl)amide in hexane (1.02 M, 2.00 mL) was added at −78° C., and the mixture was stirred at −78° C. for 1 hour. Chlorotrimethylsilane (0.27 mL) was added thereto at −78° C., and the mixture was stirred at −78° C. for 30 minutes. Then, a suspension of N-bromosuccinimide (380 mg) in tetrahydrofuran (6 mL) was slowly added dropwise thereto at −78° C. After stirring at −78° C. for 1 hour, the consumption of the reactant was confirmed, and a solution of tert-butyl (3S)-pyrrolidin-3-ylcarbamate (563 mg) in tetrahydrofuran (3 mL) was then added thereto at −78° C. The mixture was heated to room temperature and stirred for 2 hours, and diisopropylethylamine (0.79 mL) was then added thereto. After stirring at 50° C. for 12 hours, to the reaction solution, saturated aqueous ammonium chloride was added, and organic matter was extracted with ethyl acetate. The organic layer was dried over anhydrous sodium sulfate and filtered, and the solvent was distilled off under reduced pressure to obtain a crude product. This crude product was purified by silica gel column chromatography (eluting solvent: hexane/ethyl acetate=2/1-ethyl acetate-methylene chloride/methanol=10/1) to obtain the title compound (269 mg).

$^1$H-NMR (CDCl$_3$) δ: 0.95 (3H, d, J=6.3 Hz), 1.05-1.14 (2H, m), 1.18 (1.5H, t, J=7.3 Hz), 1.18 (1.5H, t, J=7.3 Hz), 1.39-1.70 (13H, m), 1.81-1.88 (2H, m), 2.03-2.09 (2H, m), 2.11-2.21 (1H, m), 2.57-2.76 (2H, m), 2.85-3.05 (4H, m), 3.59-3.65 (1H, m), 3.79 (1H, tt, J=12.2, 3.9 Hz), 4.06-4.22 (3H, m), 5.01 (0.5H, br), 5.18 (0.5H, br), 6.71 (1H, s), 7.43 (1H, s).

[Step 3] 2-[(3S)-3-Aminopyrrolidin-1-yl]-3-[1-(trans-4-methylcyclohexyl)-1H-imidazol-4-yl]propionic acid

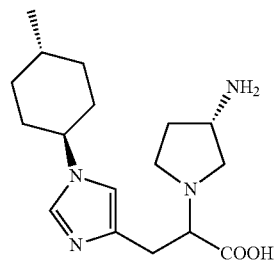

[Formula 135]

To the compound (160 mg) obtained in Step 2 of this Example, concentrated hydrochloric acid (5 mL) was added, and the mixture was heated to reflux for 10 hours. The solvent was distilled off under reduced pressure. Then, the obtained crude hydrochloride was dissolved in methanol, and DOWEX 50WX8-200 was added thereto. The resin was washed with methanol, followed by elution with 4% ammonia water. The eluate was concentrated to obtain the title compound (111 mg).

$^1$H-NMR (CD$_3$OD) δ: 0.99 (3H, d, J=6.7 Hz), 1.12-1.25 (2H, m), 1.51 (1H, m), 1.69-1.92 (5H, m), 2.03-2.13 (2H, m), 2.25 (1H, m), 2.65-2.74 (1H, m), 2.83-2.90 (1H, m), 2.91-3.14 (3H, m), 3.19 (0.5H, m), 3.27 (0.5H, m), 3.33-3.38 (1H, m), 3.74 (1H, m), 4.00 (1H, tt, J=12.1, 3.9 Hz), 7.08 (1H, s), 7.70 (0.5H, s), 7.72 (0.5H, s).

HRMS (ESI): m/z calcd for $C_{17}H_{29}N_4O_2$: 321.2291 $[M+H]^+$. found: 321.2283.

Example 27

(2S)-5-{[(1-Acetoxyethoxy)carbonyl]amino}-2-{[1-(trans-4-methylcyclohexyl)-1H-imidazol-4-yl]methyl}valeric acid

[Step 1] 1-{[(Ethylthio)carbonyl]oxy}ethyl acetate

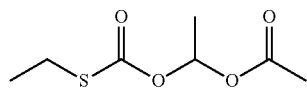

[Formula 136]

Acetic acid (1.69 mL) was dissolved in a mixed solvent of methylene chloride (100 mL) and water (50 mL). To the solution, tetrabutyl ammonium bisulfate (10.0 g) and sodium bicarbonate (4.97 g) were added in this order under ice cooling, and the mixture was then stirred for 1 hour. Subsequently, the compound obtained in Step 1 of Example 22 was added thereto, and the mixture was stirred at room temperature for 3 days. The organic layer was separated and dried over anhydrous sodium sulfate, and the solvent was distilled off under reduced pressure. The obtained residue was purified by silica gel column chromatography (eluting solvent: hexane-hexane/ethyl acetate=95/5) to obtain the title compound (1.67 g).

$^1$H-NMR (CDCl$_3$) δ: 1.32 (3H, t, J=7.4 Hz), 1.51 (3H, d, J=5.9 Hz), 2.09 (3H, s), 2.81-2.95 (2H, m), 6.94 (1H, q, J=5.9 Hz).

[Step 2] 1-[(Chlorocarbonyl)oxy]ethyl acetate

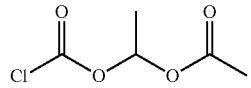

[Formula 137]

The compound (394 mg) obtained in Step 1 of this Example was cooled to −30° C. Sulfuryl chloride (175 μL) was added thereto, and the mixture was then stirred for 30 minutes. The solvent in the reaction solution was distilled off under reduced pressure to obtain a crude product of the title compound.

[Step 3] (2S)-5-{[(1-Acetoxyethoxy)carbonyl]amino}-2-{[1-(trans-4-methylcyclohexyl)-1H-imidazol-4-yl]methyl}valeric acid

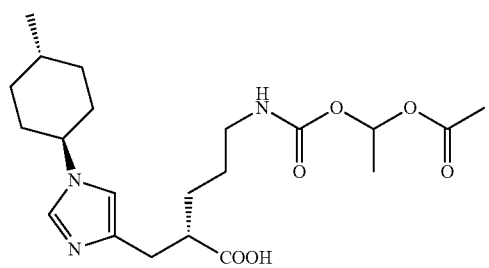

[Formula 138]

The compound (400 mg) obtained in Step 4 of Example 15 was dissolved in a mixed solvent of acetonitrile (12 mL) and water (3 mL). To the solution, a solution of the compound obtained in Step 2 of this Example in methylene chloride (1 mL) was added at 0° C., and the mixture was stirred for 2.5 hours. The solvent in the reaction solution was distilled off under reduced pressure to obtain a crude product. This crude product was purified by silica gel column chromatography (eluting solvent: ethyl acetate-methylene chloride/methanol=90/10). The obtained solid was dissolved in an ethyl acetate-acetone mixed solvent. Insoluble matter was filtered off, and the solvent in the filtrate was distilled off under reduced pressure. The obtained residue was purified by reverse-phase HPLC to obtain the title compound (185 mg).

$^1$H-NMR (CDCl$_3$) δ: 0.96 (3H, d, J=6.3 Hz), 1.09-1.21 (2H, m), 1.45 (3H, d, J=5.5 Hz), 1.52-1.75 (6H, m), 1.86-1.93 (2H, m), 2.06 (3H, s), 2.13-2.19 (2H, m), 2.82-2.91 (2H, m), 2.97-3.05 (1H, m), 3.15-3.21 (2H, m), 4.03-4.11 (1H, m), 5.31 (1H, br s), 6.77-6.81 (1H, m), 6.99 (1H, s), 8.97 (1H, s).

Example 28

(2S)-2-{[1-(trans-4-Methylcyclohexyl)-1H-imidazol-4-yl]methyl}-5-[({[(2-methylpropanoyl)oxy]methoxy}carbonyl)amino]valeric acid

[Step 1] S-Ethyl O-(iodomethyl)thiocarbonate

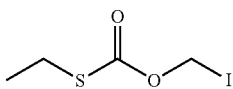

[Formula 139]

To a solution of O-(chloromethyl) S-ethyl thiocarbonate (10 g) in toluene (100 mL), sodium iodide (29.1 g) and 18-crown-6 (5.1 g) were added, and the mixture was stirred at room temperature for 19 hours. Since the starting materials still remained, sodium iodide (29.1 g) and 18-crown-6 (5.1 g) were further added thereto, and the mixture was stirred at room temperature for 48 hours and then at 100° C. for 5 hours. Ethyl acetate (100 mL) was added thereto, and the organic layer was separated by washing with a 20% aqueous sodium thiosulfate. Ethyl acetate (50 mL) was added to the aqueous layer for re-extraction. The combined organic layer was dried over anhydrous magnesium sulfate, and the solvent was then distilled off under reduced pressure. The residue was dried to obtain the title compound (12.1 g).

$^1$H-NMR (CDCl$_3$) δ: 1.34 (3H, t, J=7.4 Hz), 2.93 (2H, q, J=7.4 Hz), 5.99 (2H, s).

[Step 2] {[(Ethylsulfanyl)carbonyl]oxy}methyl 2-methylpropanoate

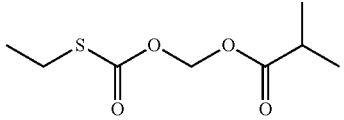

[Formula 140]

To isobutyric acid (2.9 mL) dissolved in a mixed solvent of methylene chloride and water (1:2, 120 mL), tetrabutyl ammonium bisulfate (11.0 g) and sodium bicarbonate (5.5 g)

were added under ice cooling, and the mixture was stirred at the same temperature for 10 minutes. To this reaction solution, a solution of the compound (4.0 g) obtained in Step 1 of this Example in methylene chloride (10 mL) was added at room temperature, and the mixture was stirred overnight. The organic layer was separated, and the aqueous layer was then further subjected to extraction several times with methylene chloride. The combined organic layer was dried over anhydrous magnesium sulfate, and the solvent was then distilled off under reduced pressure. The obtained residue was purified by silica gel column chromatography (eluting solvent: hexane-hexane/ethyl acetate=95/5) to obtain the title compound (2.8 g).

$^1$H-NMR (CDCl$_3$) δ: 1.19 (6H, d, J=7.0 Hz), 1.33 (3H, t, J=7.4 Hz), 2.57-2.64 (1H, m), 2.90 (2H, q, J=7.4 Hz), 5.81 (2H, s).

[Step 3] [(Chlorocarbonyl)oxy]methyl 2-methylpropanoate

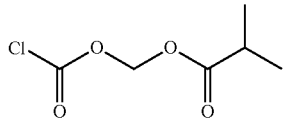

[Formula 141]

The compound (400 mg) obtained in Step 2 of this Example was cooled to −30° C. Sulfuryl chloride (159 µL) was added thereto, and the mixture was stirred at the same temperature for 20 minutes. The mixture was in turn stirred for 20 minutes in an ice bath and further at room temperature for 1 hour. The solvent was distilled off under reduced pressure, and the residue was dried to obtain a crude product of the title compound.

$^1$H-NMR (CDCl$_3$) δ: 1.22 (6H, d, J=7.0 Hz), 2.60-2.70 (1H, m), 5.83 (2H, s).

[Step 4]

(2S)-2-{[1-(trans-4-Methylcyclohexyl)-1H-imidazol-4-yl]methyl}-5-[({[(2-methylpropanoyl)oxy]methoxy}carbonyl)amino]valeric acid

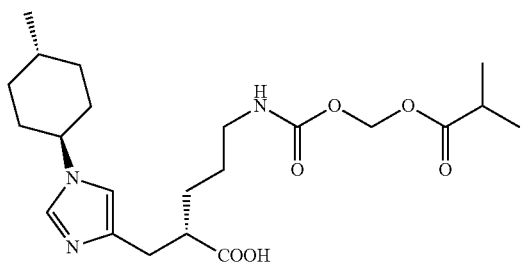

[Formula 142]

The compound (400 mg) obtained in Step 4 of Example 15 was dissolved in a mixed solvent of acetonitrile and water (1/1, 12 mL). To the solution, triethylamine (367 µL) was added under ice cooling. A solution of the compound obtained in Step 3 of this Example in acetonitrile (3.0 mL) was added thereto, and the mixture was stirred for 1.5 hours under ice cooling and then at room temperature for one day and night. The solvent was distilled off under reduced pressure, and water was then added to the residue, followed by extraction several times with ethyl acetate. The combined organic layer was dried over anhydrous magnesium sulfate, and the solvent was then distilled off under reduced pressure. The obtained residue was purified by silica gel column chromatography (eluting solvent: methylene chloride-methylene chloride/methanol=85/15) to obtain the title compound (178 mg).

$^1$H-NMR (CDCl$_3$) δ: 0.96 (3H, d, J=6.7 Hz), 1.07-1.17 (2H, m), 1.18 (6H, d, J=7.0 Hz), 1.40-1.51 (2H, m), 1.57-1.81 (5H, m), 1.84-1.91 (2H, m), 2.07-2.14 (2H, m), 2.54-2.64 (1H, m), 2.67-2.75 (1H, m), 2.78-2.89 (2H, m), 3.17-3.22 (2H, m), 3.87 (1H, tt, J=12.1, 3.9 Hz), 5.14 (1H, br s), 5.71 (2H, s), 6.75 (1H, s), 7.66 (1H, s).

LRMS (ESI) m/z 438 [M+H]$^+$.

HRMS (ESI) m/z calcd for C$_{22}$H$_{36}$N$_3$O$_6$: 438.26041 [M+H]$^+$. found: 438.26052.

Example 29

(2S)-5-[({[(2,2-Dimethylpropanoyl)oxy]methyloxy}carbonyl)amino]-2-{[1-(trans-4-methylcyclohexyl)-1H-imidazol-4-yl]methyl}valeric acid

[Step 1] {[(Ethylsulfanyl)carbonyl]oxy}methyl 2,2-dimethylpropanoate

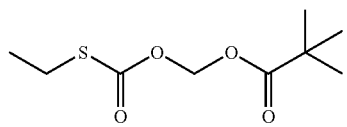

[Formula 143]

To pivalic acid (4.2 g) dissolved in a mixed solvent of methylene chloride and water (1/2, 120 mL), tetrabutyl ammonium bisulfate (11.0 g) and sodium bicarbonate (6.8 g) were added under ice cooling, and the mixture was stirred at the same temperature for 10 minutes. To this reaction solution, a solution of the compound (5.0 g) obtained in Step 1 of Example 28 in methylene chloride (10 mL) was added at room temperature, and the mixture was stirred for one day and night. The organic layer was separated, and the aqueous layer was then further subjected to extraction several times with methylene chloride. The combined organic layer was dried over anhydrous magnesium sulfate, and the solvent was then distilled off under reduced pressure. Since a solid was deposited, the solid was suspended in diethyl ether and filtered off. The filtrate was concentrated under reduced pressure, and the obtained residue was purified by silica gel column chromatography (eluting solvent: hexane-hexane/ethyl acetate=98/2) to obtain the title compound (3.6 g).

$^1$H-NMR (CDCl$_3$) δ: 1.22 (9H, s), 1.33 (3H, t, J=7.4 Hz), 2.89 (2H, q, J=7.4 Hz), 5.81 (2H, s).

[Step 2] (2S)-5-[({[(2,2-Dimethylpropanoyl)oxy]methyloxy}carbonyl)amino]-2-{[1-(trans-4-methylcyclohexyl)-1H-imidazol-4-yl]methyl}valeric acid

[Formula 144]

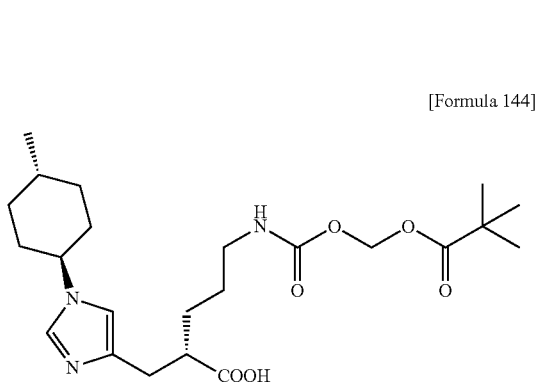 [SMILES: CC(C)(C)C(=O)OCOC(=O)NCCC[C@@H](Cc1cn([C@H]2CC[C@H](C)CC2)cn1)C(=O)O]

The title compound (297 mg) was obtained from the compound (437 mg) obtained in Step 1 of this Example and the compound (400 mg) obtained in Step 4 of Example 15 in the same way as in Steps 3 and 4 of Example 28.

$^1$H-NMR (CDCl$_3$) δ: 0.96 (3H, d, J=6.3 Hz), 1.07-1.17 (2H, m), 1.21 (9H, s), 1.41-1.50 (2H, m), 1.58-1.78 (5H, m), 1.84-1.90 (2H, m), 2.07-2.14 (2H, m), 2.67-2.74 (1H, m), 2.77-2.89 (2H, m), 3.17-3.22 (2H, m), 3.87 (1H, tt, J=12.1, 3.9 Hz), 5.13 (1H, br s), 5.71 (2H, s), 6.75 (1H, s), 7.67 (1H, s).

LRMS (ESI) m/z 452 [M+H]$^+$.

HRMS (ESI) m/z calcd for C$_{23}$H$_{38}$N$_3$O$_6$: 452.27606 [M+H]$^+$. found: 452.27619.

Example 30

(2S)-5-[({[(Cyclohexylcarbonyl)oxy]methoxy}carbonyl)amino]-2-{[1-(trans-4-methylcyclohexyl)-1H-imidazol-4-yl]methyl}valeric acid

[Step 1] {[(Ethylsulfanyl)carbonyl]oxy}methyl cyclohexanecarboxylate

[Formula 145]

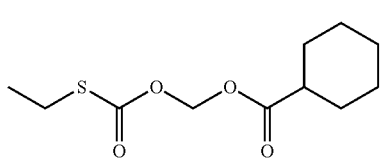

The title compound (4.1 g) was obtained from cyclohexanecarboxylic acid (5.2 g) and the compound (5.0 g) obtained in Step 1 of Example 28 in the same way as in Step 1 of Example 29.

$^1$H-NMR (CDCl$_3$) δ: 1.20-1.31 (3H, m), 1.33 (3H, t, J=7.4 Hz), 1.40-1.50 (2H, m), 1.60-1.67 (1H, m), 1.72-1.79 (2H, m), 1.87-1.95 (2H, m), 2.36 (1H, tt, J=11.3, 3.5 Hz), 2.89 (2H, q, J=7.4 Hz), 5.80 (2H, s).

[Step 2] (2S)-5-[({[(Cyclohexylcarbonyl)oxy]methoxy}carbonyl)amino]-2-{[1-(trans-4-methylcyclohexyl)-1H-imidazol-4-yl]methyl}valeric acid

[Formula 146]

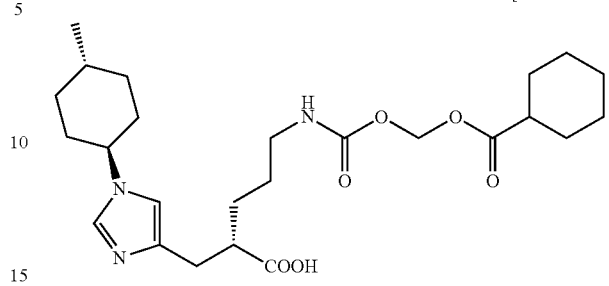

The title compound (281 mg) was obtained as a white solid from the compound (489 mg) obtained in Step 1 of this Example and the compound (400 mg) obtained in Step 4 of Example 15 in the same way as in Steps 3 and 4 of Example 28.

$^1$H-NMR (CDCl$_3$) δ: 0.96 (3H, d, J=6.3 Hz), 1.07-1.18 (2H, m), 1.19-1.33 (3H, m), 1.39-1.50 (4H, m), 1.58-1.78 (8H, m), 1.85-1.94 (4H, m), 2.08-2.14 (2H, m), 2.35 (1H, tt, J=11.3, 3.9 Hz), 2.67-2.74 (1H, m), 2.76-2.90 (2H, m), 3.17-3.22 (2H, m), 3.87 (1H, tt, J=12.1, 3.9 Hz), 5.17 (1H, br s), 5.71 (2H, s), 6.76 (1H, s), 7.68 (1H, s).

LRMS (ESI) m/z 478 [M+H]$^+$.

HRMS (ESI) m/z calcd for C$_{25}$H$_{40}$N$_3$O$_6$: 478.29171 [M+H]$^+$. found: 478.29145.

Example 31

(2S)-5-({[(Acetyloxy)methoxy]carbonyl}amino)-2-{[1-(trans-4-methylcyclohexyl)-1H-imidazol-4-yl]methyl}valeric acid

[Step 1] {[(Ethylsulfanyl)carbonyl]oxy}methyl acetate

[Formula 147]

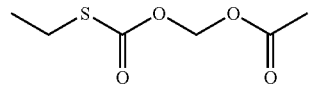

The title compound (0.86 g) was obtained from acetic acid (0.78 g) and the compound (1.6 g) obtained in Step 1 of Example 28 in the same way as in Step 1 of Example 29.

$^1$H-NMR (CDCl$_3$) δ: 1.34 (3H, t, J=7.4 Hz), 2.14 (3H, s), 2.91 (2H, q, J=7.4 Hz), 5.81 (2H, s).

[Step 2]

(2S)-5-({[(Acetyloxy)methoxy]carbonyl}amino)-2-{[1-(trans-4-methylcyclohexyl)-1H-imidazol-4-yl]methyl}valeric acid

[Formula 148]

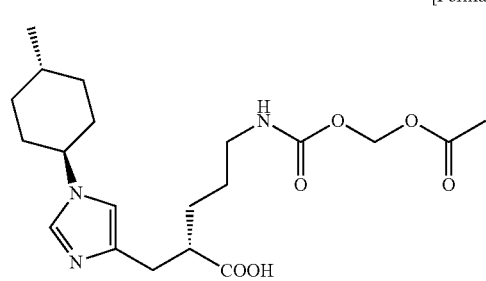

The title compound (201 mg) was obtained from the compound (177 mg) obtained in Step 1 of this Example and the compound (200 mg) obtained in Step 4 of Example 15 in the same way as in Steps 3 and 4 of Example 28.

$^1$H-NMR (CDCl$_3$) δ: 0.96 (3H, d, J=6.6 Hz), 1.07-1.18 (2H, m), 1.42-1.52 (2H, m), 1.59-1.80 (5H, m), 1.85-1.91 (2H, m), 2.09-2.14 (2H, m), 2.11 (3H, s), 2.68-2.75 (1H, m), 2.77-2.92 (2H, m), 3.18-3.23 (2H, m), 3.88 (1H, tt, J=12.1, 3.9 Hz), 5.26-5.30 (1H, br m), 5.70 (2H, s), 6.78 (1H, s), 7.78 (1H, s).

LRMS (ESI) m/z 410 [M+H]$^+$.

HRMS (ESI) m/z calcd for C$_{20}$H$_{32}$N$_3$O$_6$: 410.22911 [M+H]$^+$. found: 410.22892.

Example 32

(2S)-5-({[(1R)-1-(Isobutyloxy)ethoxy]carbonyl}amino)-2-{[1-(trans-4-methylcyclohexyl)-1H-imidazol-4-yl]methyl}valeric acid

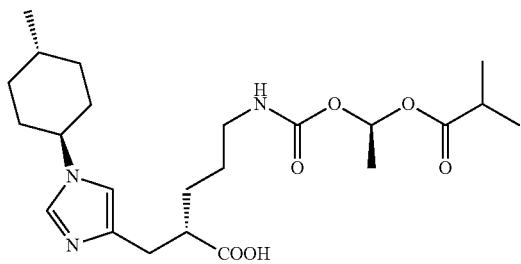

[Formula 149]

To a solution of the compound (0.75 g) obtained in Step 4 of Example 15 in water (3.13 mL), a solution of (1R)-1-({[(2,5-dioxopyrrolidin-1-yl)oxy]carbonyl}oxy)ethyl 2-methylpropionate (0.70 g) in acetonitrile (12.55 mL) was added, and the mixture was stirred at room temperature for 20 hours. To the mixture, water and ethyl acetate were added, and the organic layer was separated and dried over anhydrous magnesium sulfate. Hexane was added thereto, and the precipitated solid was collected by filtration and dried under reduced pressure to obtain the title compound (0.15 g). Analysis conditions: Daicel Chiralpak (registered trademark) AD-H, 4.6 mm×250 mm (5 μm), eluting solvent: hexane/isopropanol (containing 0.5 v % trifluoroacetic acid and 0.5 v % diethylamine)=85/15 (1 mL/min). Retention time: 9.4 min. (isomer A; not observed), 11.4 min. (isomer B; not observed), 13.6 min. (title compound), 15.8 min. (isomer C; not observed).

MS (FAB) m/z 452 [M+H]$^+$.

HRMS (ESI): m/z calcd for C$_{23}$H$_{38}$N$_3$O$_6$: 452.27606 [M+H]$^+$. found: 452.27582.

Example 33

5-Amino-2-{[1-(3,3-dimethylcyclohexyl)-1H-imidazol-4-yl]methyl}valeric acid

[Step 1] Ethyl (2E)-5-[(tert-butoxycarbonyl)amino]-2-{[1-(3,3-dimethylcyclohexyl)-1H-imidazol-4-yl]methylene}valerate

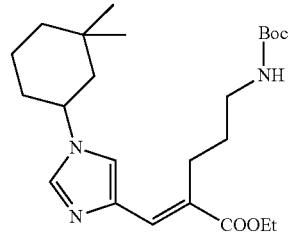

[Formula 150]

To a solution of the compound (553 mg) obtained in Reference Example 14 in tetrahydrofuran (15 mL), lithium chloride (61 mg) was added at room temperature, and the mixture was stirred for 5 minutes. To this reaction solution, 1,8-diazabicyclo[5.4.0]undec-7-ene (217 μL) was added under ice cooling, and the mixture was stirred for 20 minutes. The compound (250 mg) obtained in Reference Example 15 was further added thereto under ice cooling, and the mixture was then stirred overnight. To the reaction solution, aqueous ammonium chloride was added, followed by extraction with ethyl acetate. The organic layer was dried over anhydrous sodium sulfate and filtered, and the solvent was distilled off under reduced pressure. The obtained residue was purified by silica gel column chromatography (eluting solvent: hexane/ethyl acetate=3/7-1/1) to obtain the title compound (347 mg).

$^1$H-NMR (CDCl$_3$) δ: 1.02 (6H, s), 1.18-1.24 (1H, m), 1.32 (3H, t, J=7.0 Hz), 1.45-1.63 (16H, m), 1.72-1.82 (4H, m), 2.10-2.15 (1H, m), 2.95 (2H, t, J=7.2 Hz), 3.11-3.16 (2H, m), 4.05-4.12 (1H, m), 7.04 (1H, br s), 7.15 (1H, s), 7.47 (1H, s), 7.58 (1H, s).

[Step 2] Ethyl 5-[(tert-butoxycarbonyl)amino]-2-{[1-(3,3-dimethylcyclohexyl)-1H-imidazol-4-yl]methyl}valerate

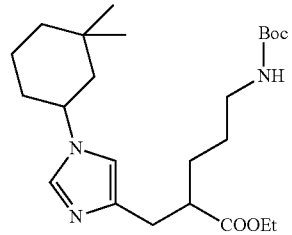

[Formula 151]

The compound (347 mg) obtained in Step 1 of this Example was dissolved in ethanol (10 mL). To the solution, 10% palladium-carbon catalyst (hydrated, 170 mg) was added, and the mixture was stirred at room temperature for 7 hours under a hydrogen atmosphere. The catalyst was filtered off, and the solvent in the filtrate was distilled off under reduced pressure. The obtained residue was purified by silica gel column chromatography (eluting solvent: hexane/ethyl acetate=1/1-ethyl acetate) to obtain the title compound (337 mg).

¹H-NMR (CDCl₃) δ: 0.99 (6H, s), 1.14-1.22 (4H, m), 1.41-1.77 (19H, m), 2.04-2.09 (1H, m), 2.68 (1H, dd, J=13.9, 6.5 Hz), 2.73-2.80 (1H, m), 2.88 (1H, dd, J=13.7, 7.4 Hz), 3.04-3.15 (2H, m), 4.00 (1H, tt, J=12.1, 3.8 Hz), 4.10 (2H, q, J=7.0 Hz), 4.73 (1H, br s), 6.67 (OH, s), 7.41 (1H, s).

[Step 3] 5-Amino-2-{[1-(3,3-dimethylcyclohexyl)-1H-imidazol-4-yl]methyl}valeric acid

[Formula 152]

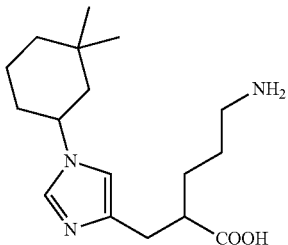

To the compound obtained in Step 2 of this Example, 5 N hydrochloric acid (10 mL) was added, and the mixture was heated to reflux for 6 hours. After standing to cool, the solvent was distilled off under reduced pressure. The obtained residue was dissolved in deionized water. To the solution, PoraPak Rxn CX (ion-exchange resin, 2.5 g) was added. The resin was washed with deionized water, followed by elution with a 2.8% ammonia/methanol solution (a solution of 28% ammonia water diluted 10-fold with methanol). The eluate was concentrated to obtain the title compound (158 mg).

¹H-NMR (CD₃OD) δ: 0.99 (3H, s), 1.02 (3H, s), 1.21-1.28 (1H, m), 1.40-1.44 (1H, m), 1.50-1.78 (9H, m), 2.00-2.05 (1H, m), 2.47-2.58 (2H, m), 2.84-2.94 (2.33H, m), 3.55 (0.66H, t, J=7.1 Hz), 4.13-4.20 (1H, m), 6.94 (0.66H, s), 6.96 (0.33H, s), 7.58 (0.66H, s), 7.62 (0.33H, s).

Example 34

(2R,4S)-5-Amino-4-methyl-2-{[1-(trans-4-methylcyclohexyl)-1H-imidazol-4-yl]methyl}valeric acid and (2S,4S)-5-amino-4-methyl-2-{[1-(trans-4-methylcyclohexyl)-1H-imidazol-4-yl]methyl}valeric acid

[Step 1] (3E,5S)-5-Methyl-3-{[1-(trans-4-methylcyclohexyl)-1H-imidazol-4-yl]methylene}piperidin-2-one

[Formula 153]

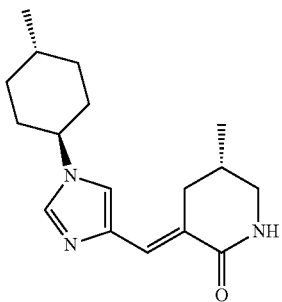

Benzyl (5S)-5-methyl-2-oxopiperidine-1-carboxylate (Org. Lett, 2009, Vol. 11, p. 5410) (1.0 g) was dissolved in tetrahydrofuran (20 mL). To the solution, lithium hexamethyldisilazide (LHMDS, 1 N tetrahydrofuran solution, 4.04 mL) was added dropwise at −78° C., and the mixture was stirred for 20 minutes. Subsequently, a solution of the compound (519 mg) obtained in Step 3 of Reference Example 4 in tetrahydrofuran (5 mL) was added dropwise thereto at −78° C., and the mixture was stirred overnight. To the reaction solution, water was added, and organic matter was extracted with ethyl acetate. The organic layer was dried over anhydrous sodium sulfate and then filtered, and the solvent was distilled off under reduced pressure to obtain a crude product. This crude product was purified by silica gel column chromatography (eluting solvent: ethyl acetate-ethyl acetate/methanol=92/8) to obtain the title compound (612 mg).

¹H-NMR (CDCl₃) δ: 0.96 (3H, d, J=6.7 Hz), 1.09 (3H, d, J=6.7 Hz), 1.10-1.17 (2H, m), 1.42-1.52 (1H, m), 1.64-1.73 (2H, m), 1.84-1.91 (2H, m), 2.07-2.14 (3H, m), 2.47 (1H, ddd, J=16.5, 11.1, 2.5 Hz), 3.06-3.12 (1H, m), 3.31-3.36 (1H, m), 3.55-3.61 (1H, m), 3.88 (1H, tt, J=12.1, 3.9 Hz), 5.78 (1H, br s), 7.12 (1H, s), 7.57 (1H, s), 7.59 (1H, s).

[Step 2] tert-Butyl (3E,5S)-5-methyl-3-{[1-(trans-4-methylcyclohexyl)-1H-imidazol-4-yl]methylene}-2-oxopiperidine-1-carboxylate

[Formula 154]

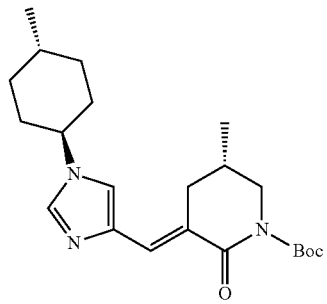

To a solution of the compound (612 mg) obtained in Step 1 of this Example in tetrahydrofuran (18 mL), a 1.57 M solution of n-BuLi in hexane (1.49 mL) was added at −78° C., and the mixture was stirred for 45 minutes. Subsequently, di-tert-butyl dicarbonate (605 mg) was added thereto at −78° C., and the mixture was gradually heated and then stirred overnight. To the reaction solution, water was added, followed by extraction with ethyl acetate. The organic layer was washed with saturated sodium chloride solution, then dried over anhydrous sodium sulfate, and filtered, and the solvent was distilled off under reduced pressure. The obtained residue was purified by silica gel column chromatography (eluting solvent: hexane/ethyl acetate=7/3-3/7) to obtain the title compound (833 mg).

¹H-NMR (CDCl₃) δ: 0.96 (3H, d, J=6.7 Hz), 1.11 (3H, d, J=6.7 Hz), 1.11-1.18 (2H, m), 1.42-1.52 (1H, m), 1.55 (9H, s), 1.63-1.73 (2H, m), 1.84-1.91 (2H, m), 2.05-2.14 (3H, m), 2.44 (1H, ddd, J=16.8, 11.0, 2.3 Hz), 3.21 (1H, dd, J=12.5, 10.2 Hz), 3.41-3.47 (1H, m), 3.85-3.93 (2H, m), 7.15 (1H, s), 7.60 (1H, s), 7.68 (1H, s).

[Step 3] tert-Butyl (5S)-5-methyl-3-{[1-(trans-4-methylcyclohexyl)-1H-imidazol-4-yl]methyl}-2-oxopiperidine-1-carboxylate

[Formula 155]

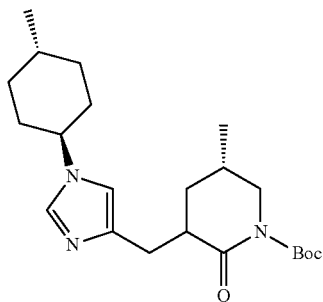

The compound (830 mg) obtained in Step 2 of this Example was dissolved in ethanol (25 mL). To the solution, 10% palladium-carbon catalyst (hydrated, 207 mg) was added, and the mixture was stirred for 13 hours under a hydrogen atmosphere. The catalyst was filtered off, and the solvent in the filtrate was distilled off under reduced pressure. The obtained residue was purified by silica gel column chromatography (eluting solvent: hexane/ethyl acetate=1/1-ethyl acetate) to obtain the title compound (788 mg).

$^1$H-NMR (CDCl$_3$) δ: 0.94 (3H, d, J=6.7 Hz), 0.96 (2H, d, J=6.7 Hz), 0.99 (1H, d, J=6.7 Hz), 1.03-1.23 (3H, m), 1.40-1.48 (1H, m), 1.52 (6H, s), 1.53 (3H, s), 1.55-1.68 (3H, m), 1.81-1.87 (2H, m), 1.96-2.10 (3H, m), 2.60-2.91 (2H, m), 3.04-3.20 (2H, m), 3.65-3.97 (2H, m), 6.73 (0.7H, s), 6.76 (0.3H, s), 7.41 (1.0H, s).

[Step 4] tert-Butyl (3R,5S)-5-methyl-3-{[1-(trans-4-methylcyclohexyl)-1H-imidazol-4-yl]methyl}-2-oxopiperidine-1-carboxylate and tert-butyl (3S,5S)-5-methyl-3-{[1-(trans-4-methylcyclohexyl)-1H-imidazol-4-yl]methyl}-2-oxopiperidine-1-carboxylate

[Formula 156]

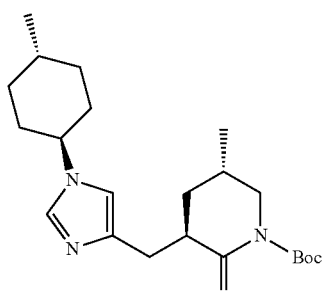
1st

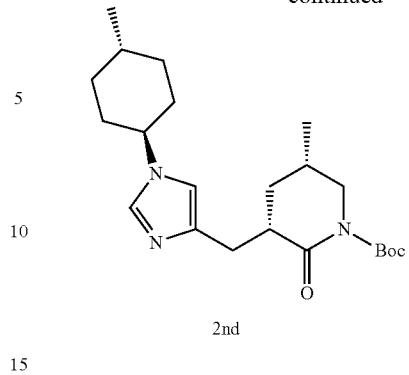
2nd

The compound (788 mg) obtained in Step 3 of this Example was diastereomerically resolved by high-performance liquid chromatography using CHIRALPAK AD-H semi-prep column (2.0 cm×25.0 cm). Flow rate: 10 mL/min, eluting solvent: hexane/isopropanol=88/12, detection wavelength: 210 nm. Column temperature: 25° C.

The solvent in the resolved solutions was distilled off under reduced pressure to respectively obtain both diastereomers ((3R,5S)-form: 72 mg and (3S,5S)-form: 371 mg). Both the diastereomers were confirmed by analytical high-performance liquid chromatography to be optically pure. Column: CHIRALPAK AD (0.46 cm×15.0 cm), flow rate: 1.3 mL/min, eluting solvent: hexane/isopropanol=80/20-20/80, detection wavelength: 210 nm, retention time: (3R,5S)-form (4.6 min.), (3S,5S)-form (5.2 min.).

[Step 5] (2R,4S)-5-Amino-4-methyl-2-{[1-(trans-4-methylcyclohexyl)-1H-imidazol-4-yl]methyl}valeric acid

[Formula 157]

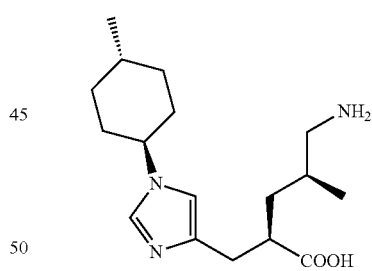

The title compound (25 mg) was obtained from tert-butyl (3R,5S)-5-methyl-3-{[1-(trans-4-methylcyclohexyl)-1H-imidazol-4-yl]methyl}-2-oxopiperidine-1-carboxylate (72 mg) obtained in Step 4 of this Example in the same way as in Step 3 of Example 33.

$^1$H-NMR (CD$_3$OD) δ: 0.95 (3H, d, J=6.8 Hz), 0.97 (3H, d, J=6.8 Hz), 1.10-1.19 (2H, m), 1.37-1.50 (2H, m), 1.64-1.75 (3H, m), 1.81-1.92 (3H, m), 2.00-2.05 (2H, m), 2.51 (1H, dd, J=14.2, 6.3 Hz), 2.54-2.60 (1H, m), 2.71 (1H, dd, J=12.7, 6.3 Hz), 2.92-2.85 (2H, m), 3.93 (1H, tt, J=12.2, 3.9 Hz), 6.93 (1H, s), 7.56 (1H, s).

HRMS (ESI): m/z calcd for C$_{17}$H$_{29}$N$_3$Na$_1$O$_2$: 330.21575 [M+H]$^+$. found: 330.21629.

[Step 6] (2S,4S)-5-Amino-4-methyl-2-{[1-(trans-4-methylcyclohexyl)-1H-imidazol-4-yl]methyl}valeric acid

[Formula 158]

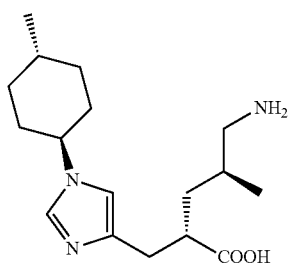

The title compound (212 mg) was obtained from tert-butyl (3S,5S)-5-methyl-3-{[1-(trans-4-methylcyclohexyl)-1H-imidazol-4-yl]methyl}-2-oxopiperidine-1-carboxylate (371 mg) obtained in Step 4 of this Example in the same way as in Step 3 of Example 33.

$^1$H-NMR (CD$_3$OD) δ: 0.95 (3H, d, J=6.8 Hz), 0.98 (3H, d, J=6.8 Hz), 1.10-1.19 (2H, m), 1.22-1.29 (1H, m), 1.43-1.51 (1H, m), 1.64-1.85 (6H, m), 2.01-2.05 (2H, m), 2.53 (1H, dd, J=13.9, 6.6 Hz), 2.55-2.61 (1H, m), 2.77 (2H, d, J=6.8 Hz), 2.88 (1H, dd, J=13.9, 7.1 Hz), 3.93 (1H, tt, J=12.0, 3.9 Hz), 6.94 (1H, s), 7.54 (1H, s).

HRMS (ESI): m/z calcd for C$_{17}$H$_{30}$N$_3$O$_2$: 308.23380 [M+H]$^+$. found: 308.23370.

Example 35

(2R,4R)-5-Amino-4-methyl-2-{[1-(trans-4-methylcyclohexyl)-1H-imidazol-4-yl]methyl}valeric acid and (2S,4R)-5-amino-4-methyl-2-{[1-(trans-4-methylcyclohexyl)-1H-imidazol-4-yl]methyl}valeric acid

[Step 1] (3E,5R)-5-Methyl-3-{[1-(trans-4-methylcyclohexyl)-1H-imidazol-4-yl]methylene}-piperidin-2-one

[Formula 159]

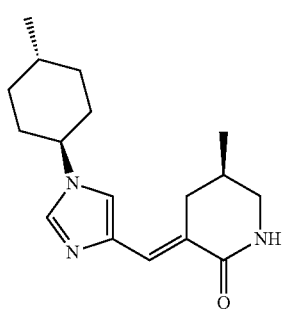

Benzyl (5R)-5-methyl-2-oxopiperidine-1-carboxylate (Org. Lett, 2009, Vol. 11, p. 5410) (772 mg) was dissolved in tetrahydrofuran (15 mL). To the solution, lithium hexamethyldisilazide (LHMDS, 1 N tetrahydrofuran solution, 3.12 mL) was added dropwise at −78° C., and the mixture was stirred for 1 hour. Subsequently, a solution of 1-(trans-4-methylcyclohexyl)-1H-imidazole-4-carbaldehyde (600 mg) in tetrahydrofuran (5 mL) was added dropwise thereto at −78° C., and the mixture was stirred at 0° C. for 3 hours. To the reaction solution, aqueous ammonium chloride was added, and organic matter was extracted with ethyl acetate. The organic layer was dried over anhydrous sodium sulfate and then filtered, and the solvent was distilled off under reduced pressure to obtain a crude product. This crude product was purified by silica gel column chromatography (eluting solvent: ethyl acetate-ethyl acetate/methanol=92/8) to obtain the title compound (500 mg).

[Step 2] tert-Butyl (3E,5R)-5-methyl-3-{[1-(trans-4-methylcyclohexyl)-1H-imidazol-4-yl]methylene}-2-oxopiperidine-1-carboxylate

[Formula 160]

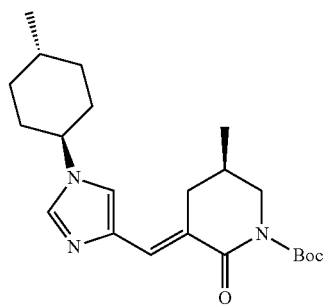

The title compound (492 mg) was obtained from the compound (500 mg) obtained in Step 1 of this Example in the same way as in Step 2 of Example 34.

[Step 3] tert-Butyl (5R)-5-methyl-3-{[1-(trans-4-methylcyclohexyl)-1H-imidazol-4-yl]methyl}-2-oxopiperidine-1-carboxylate

[Formula 161]

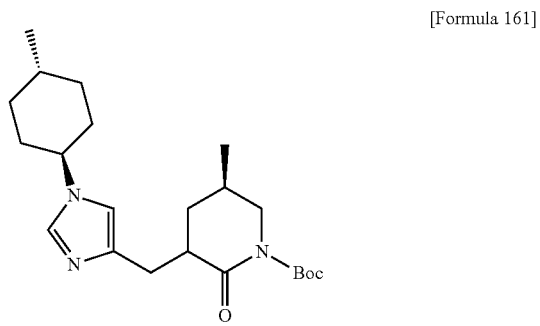 [SMILES: C[C@@H]1CC(Cc2cn([C@H]3CC[C@H](C)CC3)cn2)C(=O)N(C(=O)OC(C)(C)C)C1]

The title compound (460 mg) was obtained from the compound (490 mg) obtained in Step 2 of this Example in the same way as in Step 3 of Example 34.

[Step 4] tert-Butyl (3R,5R)-5-methyl-3-{[1-(trans-4-methylcyclohexyl)-1H-imidazol-4-yl]methyl}-2-oxopiperidine-1-carboxylate and tert-butyl (3S,5R)-5-methyl-3-{[1-(trans-4-methylcyclohexyl)-1H-imidazol-4-yl]methyl}-2-oxopiperidine-1-carboxylate

[Formula 162]

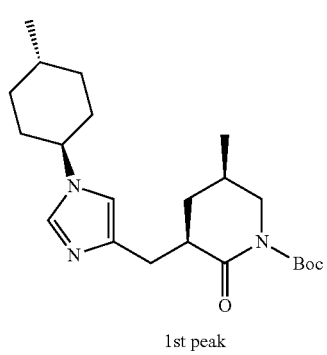

1st peak

-continued

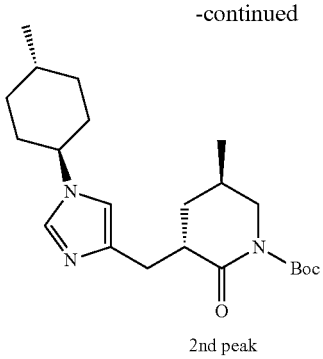

2nd peak

The compound (460 mg) obtained in Step 3 of this Example was diastereomerically resolved by high-performance liquid chromatography using CHIRALPAK AD-H semi-prep column (2.0 cm×25.0 cm). Flow rate: 10 mL/min, eluting solvent: hexane/isopropanol=90/10, detection wavelength: 210 nm. Column temperature: 25° C.

The solvent in the resolved solutions was distilled off under reduced pressure to respectively obtain both diastereomers ((3R,5R)-form: 298 mg and (3S,5R)-form: 109 mg). Both the diastereomers were confirmed by analytical high-performance liquid chromatography to be optically pure. Column: CHIRALPAK AD (0.46 cm×15.0 cm), flow rate: 1 mL/min, eluting solvent: hexane/isopropanol=80/20, detection wavelength: 210 nm, retention time: (3R,5R)-form (5.8 min.), (3S,5R)-form (7.6 min.).

[Step 5] (2R,4R)-5-Amino-4-methyl-2-{[1-(trans-4-methylcyclohexyl)-1H-imidazol-4-yl]methyl}valeric acid

[Formula 163]

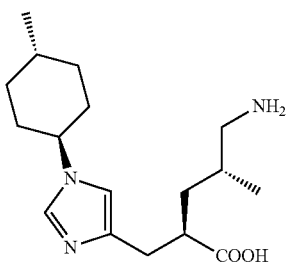

The title compound (134 mg) was obtained from tert-butyl (3R,5R)-5-methyl-3-{[1-(trans-4-methylcyclohexyl)-1H-imidazol-4-yl]methyl}-2-oxopiperidine-1-carboxylate (298 mg) obtained in Step 4 this Example in the same way as in Step 3 of Example 33.

$^1$H-NMR (CD$_3$OD) δ: 0.95 (3H, d, J=6.7 Hz), 0.98 (3H, d, J=6.7 Hz), 1.09-1.27 (3H, m), 1.43-1.52 (1H, m), 1.63-1.86 (6H, m), 2.00-2.06 (2H, m), 2.53 (1H, dd, J=13.5, 6.5 Hz), 2.56-2.62 (1H, m), 2.77 (2H, d, J=7.0 Hz), 2.88 (1H, dd, J=13.9, 6.8 Hz), 3.93 (1H, tt, J=12.1, 3.9 Hz), 6.95 (1H, s), 7.55 (1H, s).

[Step 6] (2S,4R)-5-Amino-4-methyl-2-{[1-(trans-4-methylcyclohexyl)-1H-imidazol-4-yl]methyl}valeric acid

[Formula 164]

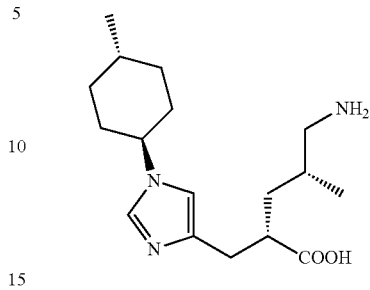

The title compound (12 mg) was obtained from tert-butyl (3S,5R)-5-methyl-3-{[1-(trans-4-methylcyclohexyl)-1H-imidazol-4-yl]methyl}-2-oxopiperidine-1-carboxylate (109 mg) obtained in Step 4 of this Example in the same way as in Step 3 of Example 33.

$^1$H-NMR (CD$_3$OD) δ: 0.95 (3H, d, J=6.7 Hz), 0.97 (3H, d, J=7.0 Hz), 1.09-1.19 (2H, m), 1.36-1.51 (2H, m), 1.63-1.77 (3H, m), 1.80-1.91 (3H, m), 2.00-2.05 (3H, m), 2.51 (1H, dd, J=13.9, 5.7 Hz), 2.54-2.61 (1H, m), 2.71 (1H, dd, J=12.9, 6.3 Hz), 2.84-2.93 (2H, m), 3.93 (1H, tt, J=12.5, 3.5 Hz), 6.93 (1H, s), 7.57 (1H, s).

Example 36

4-(Aminomethyl)-2-{[1-(trans-4-methylcyclohexyl)-1H-imidazol-4-yl]methyl}hexanoic acid

[Step 1] Ethyl 4-{[(tert-butoxycarbonyl)amino]methyl}-2-{[1-(trans-4-methylcyclohexyl)-1H-imidazol-4-yl]methyl}hex-2-enoate

[Formula 165]

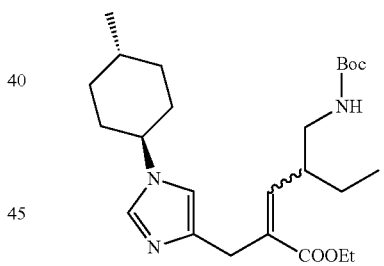

The compound (148 mg) obtained in Step 1 of Example 26 was dissolved in tetrahydrofuran (2 mL). To the solution, lithium hexamethyldisilazide (LHMDS, 1 N tetrahydrofuran solution, 561 μL) was added dropwise at −78° C., and the mixture was stirred for 1 hour. Subsequently, a solution of the compound (113 mg) obtained in Reference Example 16 in tetrahydrofuran (1 mL) was added dropwise thereto at −78° C., and the mixture was stirred at −78° C. for 3 hours. To the reaction solution, aqueous ammonium chloride was added, and organic matter was extracted with ethyl acetate. The organic layer was dried over anhydrous sodium sulfate and then filtered, and the solvent was distilled off under reduced pressure to obtain a crude product. This crude product was dissolved in methylene chloride (5 mL). To the solution, methanesulfonyl chloride (87 μL) and triethylamine (235 μL) were added at room temperature, and the mixture was stirred for 3 hours. 1,8-diazabicyclo[5.4.0]undec-7-ene (251 μL) was added thereto at room temperature, and the mixture was stirred overnight. To the reaction solution, methylene chloride was added, and the organic layer was washed with water and saturated sodium chloride solution, then dried over anhydrous sodium sulfate, and filtered, and the solvent was distilled off under reduced pressure. The obtained residue was purified by thin-layer silica gel column chromatography (developing solvent: methylene chloride/methanol=95/5) to obtain the title compound (81 mg).

$^1$H-NMR (CDCl$_3$) δ: 0.89 (3H, t, J=7.4 Hz), 0.94 (3H, d, J=6.7 Hz), 1.05-1.16 (2H, m), 1.26 (3H, t, J=7.0 Hz), 1.33-1.40 (2H, m), 1.44 (9H, s), 1.55-1.63 (3H, m), 1.80-1.87 (2H, m), 2.04-2.09 (2H, m), 2.85-2.94 (1H, m), 3.04-3.11 (1H, m), 3.32-3.37 (1H, m), 3.49 (1H, d, J=14.1 Hz), 3.61 (1H, d, J=14.5 Hz), 3.73-3.81 (1H, m), 4.05-4.19 (2H, m), 6.57 (0.5H, s), 6.59 (0.5H, s), 6.76 (1H, s), 7.39 (1H, s), 8.13 (1H, br s).

[Step 2] Ethyl 4-{[(tert-butoxycarbonyl)amino]methyl}-2-{[1-(trans-4-methylcyclohexyl)-1H-imidazol-4-yl]methyl}hexanoate

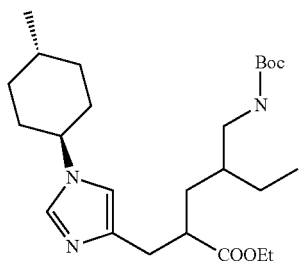

[Formula 166]

The title compound (47 mg) was obtained from the compound (80 mg) obtained in Step 1 of this Example in the same way as in Step 3 of Example 34.

$^1$H-NMR (CDCl$_3$) δ: 0.83 (1H, t, J=7.4 Hz), 0.88 (2H, t, J=7.4 Hz), 0.95 (3H, d, J=6.3 Hz), 1.04-1.15 (2H, m), 1.19 (1H, t, J=7.0 Hz), 1.20 (1H, t, J=7.0 Hz), 1.25-1.34 (3H, m), 1.42-1.48 (11H, m), 1.58-1.68 (3H, m), 1.81-1.86 (2H, m), 2.03-2.09 (2H, m), 2.63-2.72 (1H, m), 2.82-2.99 (2H, m), 3.05-3.18 (2H, m), 3.75-3.83 (1H, m), 4.09 (1H, q, J=7.0 Hz), 4.10 (1H, q, J=7.0 Hz), 5.46 (1H, br s), 6.68 (1H, s), 7.42 (1H, s).

[Step 3] 4-(Aminomethyl)-2-{[1-(trans-4-methylcyclohexyl)-1H-imidazol-4-yl]methyl}hexanoic acid hydrochloride

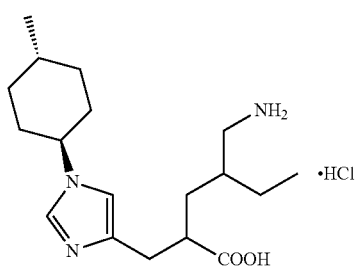

[Formula 167]

To the compound (47 mg) obtained in Step 2 of this Example, 5 N hydrochloric acid (2 mL) was added, and the mixture was heated to reflux for 5 hours. After standing to cool, the solvent was distilled off under reduced pressure. The obtained residue was dissolved in deionized water. Insoluble matter was filtered off through a membrane filter, and the solvent was distilled off again to obtain the title compound (37 mg) of interest.

$^1$H-NMR (CD$_3$OD) δ: 0.90-0.98 (6H, m), 1.16-1.24 (2H, m), 1.36-1.57 (4H, m), 1.74-1.92 (6H, m), 2.12-2.16 (2H, m), 2.85-3.03 (5H, m), 4.21-4.27 (1H, m), 7.55 (0.5H, s), 7.56 (0.5H, s), 8.90 (0.5H, s), 8.92 (0.5H, s).

HRMS (ESI): m/z calcd for C$_{18}$H$_{32}$N$_3$O$_2$: 322.24945 [M+H]$^+$.. found: 322.24948.

Example 37

5-Amino-2-{[1-(cis-4-hydroxycyclohexyl)-1H-imidazol-4-yl]methyl}valeric acid

[Step 1] Ethyl (2E)-5-[(tert-butoxycarbonyl)amino]-2-{[1-(cis-4-{[tert-butyl(diphenyl)silyl]oxy}cyclohexyl)-1H-imidazol-4-yl]methylene}valerate

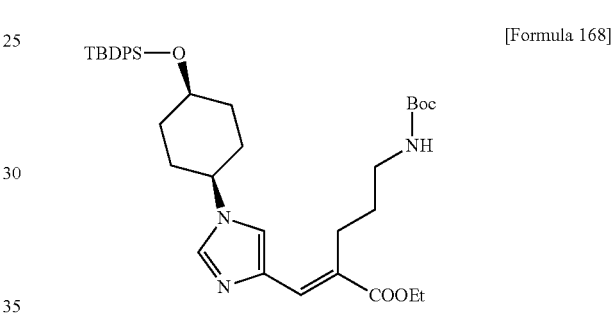

[Formula 168]

The title compound (375 mg) was obtained using the compound (307 mg) obtained in Reference Example 17 and the compound obtained in Reference Example 14 in the same way as in Step 1 of Example 33.

$^1$H-NMR (CDCl$_3$) δ: 1.10 (9H, s), 1.33 (3H, t, J=7.1 Hz), 1.41-1.46 (2H, m), 1.48 (9H, s), 1.74-1.91 (6H, m), 2.22-2.31 (2H, m), 2.98 (2H, t, J=7.3 Hz), 3.14-3.17 (2H, m), 3.89-3.95 (1H, m), 4.06-4.09 (1H, m), 4.24 (2H, q, J=7.0 Hz), 7.19 (1H, s), 7.37-7.41 (4H, m), 7.43-7.46 (2H, m), 7.49 (1H, s), 7.64-7.67 (5H, m).

[Step 2] Ethyl (2E)-5-[(tert-butoxycarbonyl)amino]-2-{[1-(cis-4-hydroxycyclohexyl)-1H-imidazol-4-yl]methylene}valerate

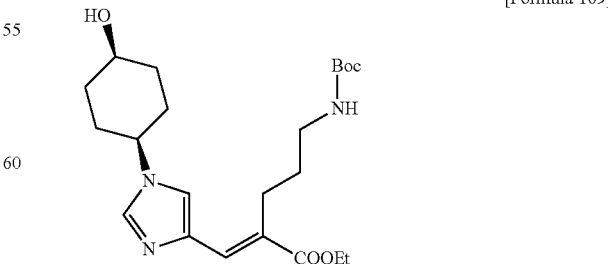

[Formula 169]

The compound obtained in Step 1 of this Example was dissolved in tetrahydrofuran (10 mL). To the solution, a solution of tetrabutyl ammonium fluoride in tetrahydrofuran (1.0 M, 682 µL) was added at room temperature, and the mixture was stirred overnight. A solution of tetrabutyl ammonium fluoride in tetrahydrofuran (1.0 M, 204 µL) was further added thereto at room temperature, and the mixture was stirred for 4 days. The solvent in the reaction solution was distilled off under reduced pressure, and the obtained residue was purified by silica gel column chromatography (eluting solvent: hexane/ethyl acetate=1/1-ethyl acetate) to obtain the title compound (220 mg).

¹H-NMR (CDCl₃) δ: 1.32 (3H, t, J=7.3 Hz), 1.47 (9H, s), 1.66-1.78 (4H, m), 1.88-1.98 (4H, m), 2.12-2.20 (2H, m), 2.93 (2H, t, J=7.3 Hz), 3.12-3.16 (2H, m), 3.93-4.00 (1H, m), 4.12-4.15 (1H, m), 4.23 (2H, q, J=7.2 Hz), 6.94 (1H, br s), 7.21 (1H, s), 7.49 (1H, s), 7.61 (1H, s).

[Step 3] Ethyl 5-[(tert-butoxycarbonyl)amino]-2-{[1-(cis-4-hydroxycyclohexyl)-1H-imidazol-4-yl] methyl}valerate

[Formula 170]

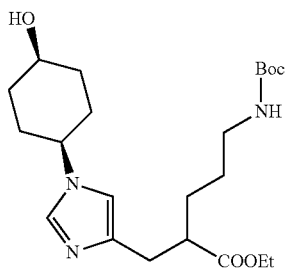

The title compound (51 mg) was obtained from the compound (50 mg) obtained in Step 2 of this Example in the same way as in Step 2 of Example 33.

¹H-NMR (CDCl₃) δ: 1.20 (3H, t, J=7.4 Hz), 1.43 (9H, s), 1.48-1.71 (6H, m), 1.83-1.94 (4H, m), 2.05-2.15 (2H, m), 2.69 (1H, dd, J=13.9, 6.5 Hz), 2.74-2.81 (1H, m), 2.89 (1H, dd, J=13.7, 7.4 Hz), 3.05-3.14 (2H, m), 3.83-3.90 (1H, m), 4.07-4.13 (3H, m), 4.74 (1H, br s), 6.72 (1H, s), 7.45 (1H, s).

[Step 4] 5-Amino-2-{[1-(cis-4-hydroxycyclohexyl)-1H-imidazol-4-yl]methyl}valeric acid

[Formula 171]

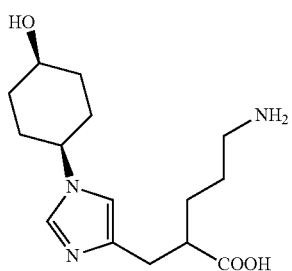

The title compound (26 mg) was obtained from the compound (51 mg) obtained in Step 3 of this Example in the same way as in Step 3 of Example 33.

¹H-NMR (CD₃OD) δ: 1.61-1.89 (10H, m), 2.04-2.12 (2H, m), 2.48-2.59 (2H, m), 2.85-2.92 (3H, m), 3.96-4.02 (2H, m), 6.96 (1H, s), 7.59 (1H, s).

Example 38

5-Amino-2-({1-[trans-4-(pyridin-4-yloxy)cyclohexyl]-1H-imidazol-4-yl}methyl)valeric acid

[Step 1] Ethyl (2E)-5-[(tert-butoxycarbonyl)amino]-2-({1-[trans-4-(pyridin-4-yloxy)cyclohexyl]-1H-imidazol-4-yl}methylene)valerate

[Formula 172]

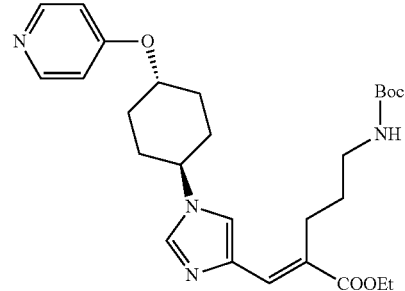

The compound (170 mg) obtained in Step 2 of Example 37 was dissolved in tetrahydrofuran (6 mL). To the solution, triphenylphosphine (137 mg), 4-hydroxypyridine (50 mg), and a 40% solution of diisopropyl azodicarboxylate in toluene (276 µL) were added, and the mixture was stirred at 55° C. for 5.5 hours. The solvent in the reaction solution was distilled off under reduced pressure, and the obtained residue was purified by silica gel column chromatography (eluting solvent: hexane/ethyl acetate=7/3-ethyl acetate) to obtain the title compound (51 mg).

¹H-NMR (CDCl₃) δ: 1.33 (3H, t, J=7.0 Hz), 1.48 (9H, s), 1.68-1.79 (4H, m), 1.84-1.93 (2H, m), 2.25-2.36 (4H, m), 2.90-2.95 (2H, m), 3.12-3.17 (2H, m), 4.04-4.09 (1H, m), 4.24 (2H, q, J=7.2 Hz), 4.39-4.45 (1H, m), 6.78-6.82 (3H, m), 7.19 (1H, s), 7.49 (1H, s), 7.62 (1H, s), 8.44 (2H, dd, J=5.1, 1.6 Hz).

[Step 2] Ethyl 5-[(tert-butoxycarbonyl)amino]-2-({1-[trans-4-(pyridin-4-yloxy)cyclohexyl]-1H-imidazol-4-yl}methyl)valerate

[Formula 173]

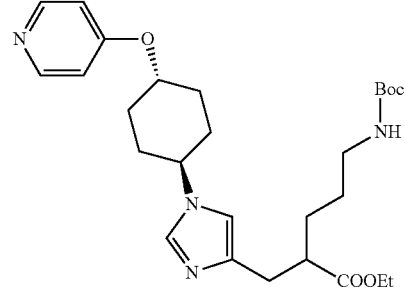

The title compound (45 mg) was obtained from the compound (50 mg) obtained in Step 1 of this Example in the same way as in Step 2 of Example 33.

$^1$H-NMR (CDCl$_3$) δ: 1.20 (3H, t, J=7.0 Hz), 1.44 (9H, s), 1.51-1.70 (6H, m), 1.77-1.87 (2H, m), 2.20-2.32 (4H, m), 2.69 (1H, dd, J=13.7, 6.7 Hz), 2.74-2.81 (1H, m), 2.90 (1H, dd, J=13.7, 7.4 Hz), 3.06-3.14 (2H, m), 3.97 (1H, tt, J=11.7, 3.9 Hz), 4.10 (3H, q, J=7.0 Hz), 4.38 (1H, tt, J=11.0, 3.9 Hz), 4.70 (1H, br s), 6.70 (1H, s), 6.80 (2H, dd, J=4.7, 1.6 Hz), 7.45 (1H, s), 8.43 (2H, dd, J=4.7, 1.6 Hz).

[Step 3] 5-Amino-2-({1-[trans-4-(pyridin-4-yloxy)cyclohexyl]-1H-imidazol-4-yl}methyl)valeric acid hydrochloride

[Formula 174]

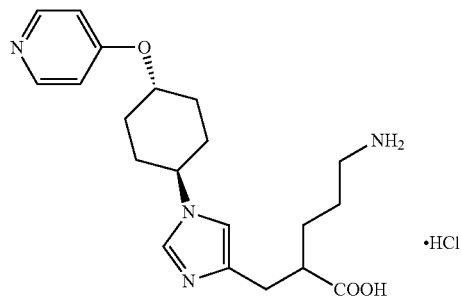

The title compound (32 mg) was obtained from the compound (45 mg) obtained in Step 2 of this Example in the same way as in Step 3 of Example 36.

$^1$H-NMR (CD$_3$OD) δ: 1.69-1.89 (6H, m), 2.06-2.17 (2H, m), 2.28-2.42 (4H, m), 2.79-2.85 (1H, m), 2.90-2.99 (3H, m), 3.04 (2H, dd, J=15.3, 9.0 Hz), 4.47 (1H, tt, J=12.1, 3.9 Hz), 4.96 (1H, tt, J=11.3, 4.3 Hz), 7.60-7.64 (3H, m), 8.63-8.65 (2H, m), 8.96-8.97 (1H, m).

Example 39

5-Amino-2-{[1-(cis-4-methylcyclohexyl)-1H-imidazol-4-yl]methyl}valeric acid

[Step 1] Methyl (2E)-5-[(tert-butoxycarbonyl)amino]-2-{[1-(cis-4-methylcyclohexyl)-1H-imidazol-4-yl]methylene}valerate

[Formula 175]

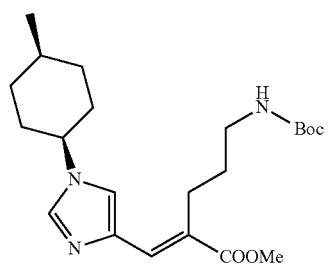

The title compound (1.42 g) was obtained from the compound (0.79 g) obtained in Reference Example 18 in the same way as in Step 1 of Example 3.

$^1$H-NMR (CDCl$_3$) δ: 1.00 (3H, d, J=7.0 Hz), 1.44-1.53 (3H, m), 1.48 (9H, s), 1.63-1.80 (4H, m), 1.85-2.04 (5H, m), 2.98 (2H, t, J=7.2 Hz), 3.13-3.17 (2H, m), 3.78 (3H, s), 4.00-4.06 (1H, m), 7.19 (1H, s), 7.48 (1H, s), 7.65 (1H, s).

[Step 2] Methyl 5-[(tert-butoxycarbonyl)amino]-2-{[1-(cis-4-methylcyclohexyl)-1H-imidazol-4-yl]methyl}valerate

[Formula 176]

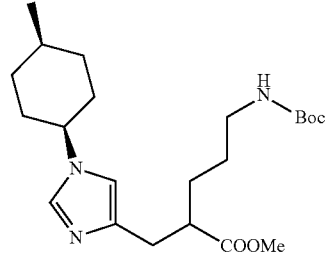

The title compound (1.11 g) was obtained from the compound (1.42 g) obtained in Step 1 of this Example in the same way as in Step 2 of Example 33.

$^1$H-NMR (CDCl$_3$) δ: 0.98 (3H, d, J=6.7 Hz), 1.44 (9H, s), 1.44-1.69 (7H, m), 1.81-1.88 (4H, m), 1.92-2.01 (2H, m), 2.72 (1H, dd, J=13.7, 5.9 Hz), 2.78-2.85 (1H, m), 2.90 (1H, dd, J=13.7, 7.8 Hz), 3.05-3.15 (2H, m), 3.64 (3H, s), 3.90-3.96 (1H, m), 4.76 (1H, brs), 6.72 (1H, s), 7.50 (1H, s).

[Step 3] 5-Amino-2-{[1-(cis-4-methylcyclohexyl)-1H-imidazol-4-yl]methyl}valeric acid

[Formula 177]

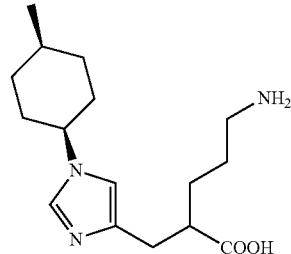

The title compound (0.39 g) was obtained from the compound (1.11 g) obtained in Step 2 of this Example in the same way as in Step 3 of Example 33.

$^1$H-NMR (CD$_3$OD) δ: 1.02 (3H, d, J=7.3 Hz), 1.46-1.55 (3H, m), 1.58-1.72 (5H, m), 1.80-1.87 (3H, m), 1.98-2.06 (2H, m), 2.47-2.58 (2H, m), 2.85-2.94 (3H, m), 3.99-4.04 (1H, m), 6.98 (1H, s), 7.59 (1H, s).

HRMS (ESI) m/z calcd C$_{16}$H$_{28}$N$_3$O$_2$: 294.21815 [M+H]$^+$. found: 294.21739.

Example 40

(2S)-5-Amino-2-{[1-(trans-4-methylcyclohexyl)-1H-imidazol-4-yl]methyl}valeric acid p-toluenesulfonate anhydrate

[Formula 178]

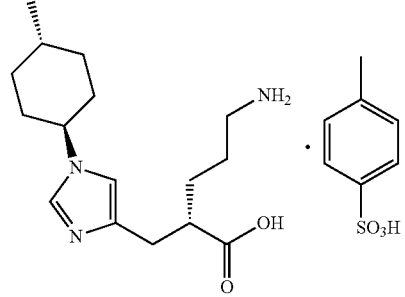

The compound (2.04 g) obtained in Step 4 of Example 15 was suspended in tetrahydrofuran (15 mL), and this suspension was stirred. p-Toluenesulfonate monohydrate (1.32 g) was added thereto, and the mixture was stirred at room temperature for 1 day. The precipitated crystals were collected by filtration under reduced pressure and dried in air for 1 day to obtain the title compound (3.01 g).

$^1$H-NMR (CD$_3$OD) δ: 0.95 (3H, d, J=6.5 Hz), 1.11-1.21 (2H, m), 1.43-1.79 (7H, m), 1.83-1.89 (2H, m), 2.05-2.10 (2H, m), 2.37 (3H, s), 2.57-2.64 (1H, m), 2.70 (1H, dd, J=14.5, 5.5 Hz), 2.85-2.95 (3H, m), 4.07 (1H, tt, J=11.7, 3.9 Hz), 7.18 (1H, s), 7.23 (2H, d, J=7.8 Hz), 7.70 (2H, d, J=8.2 Hz), 8.22 (1H, s).

Anal.: C$_{16}$H$_{27}$N$_3$O$_2$·C$_7$H$_8$O$_3$S,
Theoretical: C, 59.33; H, 7.58; N, 9.02; O, 17.18; S, 6.89.
Found: C, 59.09; H, 7.53; N, 8.92; O, 17.22; S, 6.78.

Results of powder X-ray diffraction of the obtained title compound are shown in FIG. 1 and Table 1, and its results of thermal analysis (TG/DTA) are shown in FIG. 2. In this thermal analysis (TG/DTA), measurement was performed at a heating rate of 10° C./min. under a stream of 200 mL/min. dry nitrogen.

TABLE 1

Powder X-ray diffraction of compound of Example 40

| Diffraction peak 2θ (°) | Interplanar spacing d (Å) | Relative intensity (%) |
|---|---|---|
| 3.7 | 23.9 | 100 |
| 7.4 | 11.9 | 39.0 |
| 11.4 | 7.8 | 12.2 |
| 17.6 | 5.0 | 14.3 |
| 19.0 | 4.7 | 12.4 |
| 19.9 | 4.5 | 63.6 |
| 20.7 | 4.3 | 22.1 |
| 22.9 | 3.9 | 14.0 |
| 24.9 | 3.6 | 17.6 |
| 27.8 | 3.2 | 11.0 |

Example 41

(2S)-5-Amino-2-{[1-(trans-4-methylcyclohexyl)-1H-imidazol-4-yl]methyl}valeric acid p-toluenesulfonate monohydrate

[Formula 179]

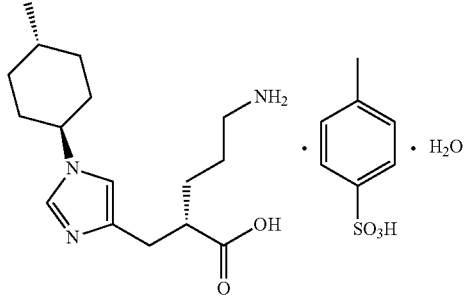

To the compound (101.6 mg) obtained in Example 40, 6% hydrated tetrahydrofuran (600 μL) was added, and the compound was dissolved by heating at 60° C. The solution was left at room temperature for 1 day, and the precipitated crystals were collected by filtration and dried in air for 1 day to obtain the title compound (79.3 mg).

Anal.: C$_{16}$H$_{27}$N$_3$O$_2$·C$_7$H$_8$O$_3$S·1H$_2$O,
Theoretical: C, 57.12; H, 7.71; N, 8.69; O, 19.85; S, 6.63.
Found: C, 56.90; H, 7.69; N, 8.67; O, 19.81; S, 6.42.

Results of powder X-ray diffraction of the obtained title compound are shown in FIG. 3 and Table 2, and its results of thermal analysis (TG/DTA) are shown in FIG. 4. In this thermal analysis (TG/DTA), measurement was performed at a heating rate of 10° C./min. under a stream of 200 mL/min. dry nitrogen.

TABLE 2

Powder X-ray diffraction of compound of Example 41

| Diffraction peak 2θ (°) | Interplanar spacing d (Å) | Relative intensity (%) |
|---|---|---|
| 3.9 | 22.9 | 73.9 |
| 6.7 | 13.1 | 21.8 |
| 7.7 | 11.5 | 35.3 |
| 10.4 | 8.5 | 20.7 |
| 11.5 | 7.7 | 21.4 |
| 13.8 | 6.4 | 23.7 |
| 14.2 | 6.3 | 26.9 |
| 14.6 | 6.1 | 31.2 |
| 15.5 | 5.7 | 35.7 |
| 16.4 | 5.4 | 40.4 |
| 17.6 | 5.0 | 61.9 |
| 18.1 | 4.9 | 48.0 |
| 18.8 | 4.7 | 100 |
| 19.6 | 4.5 | 38.1 |
| 20.8 | 4.3 | 41.1 |
| 21.1 | 4.2 | 45.3 |
| 22.2 | 4.0 | 51.5 |
| 24.3 | 3.7 | 29.1 |

Test Example 1

Determination of TAFIa Enzyme Inhibitory Activity (1) Activation of TAFI

HEPES buffered saline (20 mM HEPES, 150 mM NaCl, pH 7.4; hereinafter, referred to as HBS) was used in the preparation of a reaction solution. To 12 μL of a 250 μg/mL TAFI solution, 30 μL of an HBS solution containing 4 U/mL human thrombin, 12 U/mL rabbit lung thrombomodulin, and 12 mM CaCl$_2$ was added, and the mixture was gently stirred. Then, TAFI was activated at room temperature. Ten minutes later, thrombin was neutralized by the addition of 10 μL of 100 μM PPACK (thrombin inhibitor) to terminate the activation of TAFI. The formed TAFIa was stored in ice and diluted immediately before use in determination with 2050 μL of an HBS solution containing BSA (bovine serum albumin) adjusted to 0.1% in terms of the final concentration.

(2) Determination of TAFIa Inhibitory Activity

A test substance was dissolved in HBS to prepare a 10-fold dilution series of evaluation concentrations. 80 μl, of the TAFIa solution and 10 μL of the test substance were added to each well of a 96-well plate and mixed by shaking for 10 minutes. 10 μL, of furylacryloyl-alanyl-lysine (FAAK) adjusted to 5 mg/mL was added to each well, and the change in the absorbance of this mixed solution at 330 nm was read for 30 minutes to determine the degradation rate of the substrate.

(3) Calculation of Inhibitory Activity IC$_{50}$

The degradation rate of the substrate in each well was applied to a standard curve prepared using the dilution series of the TAFIa solution to calculate TAFIa activity. The 50% inhibitory concentration (IC$_{50}$) was calculated based on the correlation between the concentration of the test compound and the TAFIa activity. Compound A (compound of Example 7 in the pamphlet of International Publication No. WO 2002/014285) was used as a control. The results are shown in Table 3.

TABLE 3

TAFIa enzyme inhibitory activity

| Example No. | TAFIa $IC_{50}$ (μM) |
|---|---|
| 1 | 0.021 |
| 2 | 0.0083 |
| 3 | 0.0088 |
| 4 | 0.014 |
| 5 | 0.036 |
| 6 | 0.021 |
| 7 | 0.026 |
| 8 | 0.019 |
| 9 | 0.018 |
| 10 | 0.021 |
| 11 | 0.014 |
| 12 | 0.025 |
| 13 | 0.012 |
| 14 | 0.013 |
| 15(2R form) | >0.10 |
| 15(2S form) | 0.0078 |
| 24 | 0.0081 |
| 25 | 0.0070 |
| 26 | 0.021 |
| 33 | 0.0075 |
| 34(2R,4S form) | 0.034 |
| 34(2S,4S form) | 0.0054 |
| 35(2R,4R form) | >0.10 |
| 35(2S,4R form) | 0.0051 |
| 36 | 0.010 |
| 37 | 0.019 |
| 38 | 0.0098 |
| 39 | 0.0093 |
| 40 | 0.0026 |
| Compound A | 0.034 |

The compound of the present invention exhibits excellent TAFIa inhibitory activity and is useful as a pharmaceutical drug for the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis.

Test Example 2

Evaluation of Fibrinolysis Enhancing Activity by Measurement of Time of Plasma Clot Lysis To a 96-well plate, 20 μL/well HBS, 50 μL/well normal human plasma, 10 μL/well compound solution (the compound solution was prepared by dissolving the compound in HBS, followed by serial dilution with this buffer), and 10 μL/well tPA (Activacin (Kyowa Hakko Kirin Co., Ltd.) was adjusted to 600,000 U/mL with a lysis solution included therein, followed by dilution with HBS) were added, and the mixture was stirred. Then, 10 μL/well reaction solution A (13.8 U/mL human thrombin, 170 mM $CaCl_2$, and 0.9 U/mL thrombomodulin) was added thereto, and the mixture was stirred again. The absorbance at 405 nm was measured using a plate reader at 30-second intervals, with the temperature kept at 37° C. to measure the extent of coagulation. In change in absorbance, a point in time when each well exhibited absorbance closest to an average (ABS-ave: [(ABS-max)−(ABS-min)]/2) of the maximum absorbance (ABS-max) and the minimum absorbance (ABS-min) in the fibrinolysis process was defined as 1/2 lysis time (1/2 LT) and used as the fibrinolytic activity of each well. A concentration that achieves 50% of 1/2 LT was calculated as $EC_{50}$ from the relationship between the concentration of the test substance and 1/2 LT. Compound A (compound of Example 7 in the pamphlet of International Publication No. WO 2002/014285) was used as a control. The results are shown in Table 4.

TABLE 4

Fibrinolysis enhancing activity

| Example | Plasma clot lysis $EC_{50}$ (nM) |
|---|---|
| 15 (2S form) | 12 |
| Compound A | 65 |

The compound of the present invention exhibits excellent fibrinolysis enhancing activity and is useful as a pharmaceutical drug for the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis.

Test Example 3

Evaluation of Fibrinolysis Enhancing Activity in Rat Models of Thromboembolism

Wistar rats (purchased from Japan SLC, Inc.) were used. At any point in time, a test substance prepared with a 0.5% methylcellulose solution was orally administered thereto or a test substance prepared with saline was intravenously administered thereto. Forty minutes or four hours later, a PT reagent (Thromboplastin C plus, Sysmex Corp.) adjusted to 2.25 U/mL with saline was continuously injected (16.8 mL/kg/hr× 20 min) from the jugular veins under thiopental anesthesia. An excessive-dose TAFIa inhibitor-administered group was selected as a positive control group. Forty five minutes after the beginning of the PT reagent treatment, blood was collected from the jugular veins using citric acid to obtain plasma. The amount of D-dimer contained in the plasma was measured using a coagulation analyzer ACL-9000 or ACL-TOP500CTS. Its ratio to the average value of the positive control group was calculated, and $ED_{50}$ was calculated as a dose increasing D-dimer by 50%.

The compound of the present invention exhibits excellent fibrinolysis promoting activity in vivo and is useful as a pharmaceutical drug for the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis.

Preparation Example 1

Hard Capsule

Each of standard hard gelatin capsule shells separable to two parts is filled with 100 mg of the compound of Example 1 in a powder form, 150 mg of lactose, 50 mg of cellulose, and 6 mg of magnesium stearate to prepare unit capsules, which are then washed and then dried.

Preparation Example 2

Soft Capsule

A mixture of the compound of Example 2 contained in a digestible oil substance, for example, soybean oil, cottonseed oil, or olive oil, is prepared and injected into gelatin using a positive displacement pump to obtain soft capsules containing 100 mg of the active ingredient. These soft capsules are washed and then dried.

Preparation Example 3

Tablet

Each tablet is prepared according to a conventional method using 100 mg of the compound of Example 3, 0.2 mg of colloidal silicon dioxide, 5 mg of magnesium stearate, 275 mg of microcrystalline cellulose, 11 mg of starch, and 98.8 mg of lactose.

If desired, a coating is applied to the tablet.

Preparation Example 4

Suspension 5 mL of a suspension is produced to contain 100 mg of the compound of Example 4 in a fine powder form, 100 mg of sodium carboxy methylcellulose, 5 mg of sodium benzoate, 1.0 g of a sorbitol solution (Japanese Pharmacopoeia), and 0.025 mL of vanillin.

Preparation Example 5

Cream 100 mg of the compound of Example 5 in a fine powder form is mixed into 5 g of a cream containing 40% white petrolatum, 3% microcrystalline wax, 10% lanoline, 5% Span-20, 0.3% Tween-20, and 41.7% water to produce a cream.

Preparation Example 6

Injection 1.5% by weight of the compound of Example 6 is stirred in 10% by weight of propylene glycol, subsequently adjusted to a given volume with injectable water, and then sterilized to prepare an injection.

INDUSTRIAL APPLICABILITY

A cycloalkyl-substituted imidazole derivative of the present invention represented by the general formula (I) or a pharmacologically acceptable salt thereof has excellent TAFIa enzyme inhibitory activity and is useful as a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, pulmonary fibrosis, or the like, or as a therapeutic drug for a thromboembolism-derived disease.

The invention claimed is:

1. A compound represented by the general formula (I):

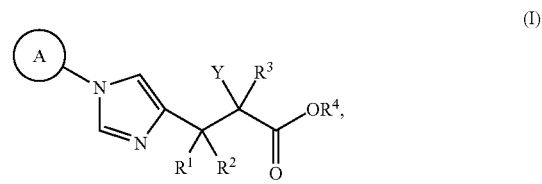

or a pharmacologically acceptable salt thereof;

wherein A is a C3 to C12 cycloalkyl group substituted by one or two identical or different C1 to C6 alkyl groups;

$R^1$, $R^2$, and $R^3$ are each independently a hydrogen atom, a fluoro group, or a C1 to C6 alkyl group;

$R^4$ is a hydrogen atom or a prodrug group; and

Y is a group selected from:

—$CH_2$—$CHR^5$—$CH_2$—$NHR^6$, where $R^5$ is a hydrogen atom, a C1 to C6 alkyl group, or a C1 to C6 alkoxy group, and $R^6$ is a hydrogen atom or a prodrug group;

—O—$CHR^7$—$CH_2$—$NHR^8$, wherein $R^7$ is a hydrogen atom, a C1 to C6 alkyl group, or a C1 to C6 alkoxy group, and $R^8$ is a hydrogen atom or a prodrug group; or

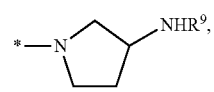

wherein $R^9$ is a hydrogen atom or a prodrug group, and * is the position for substitution.

2. The compound of claim 1 or a pharmacologically acceptable salt thereof, wherein A is a C3 to C12 cycloalkyl group substituted by a methyl group or an ethyl group.

3. The compound of claim 1 or a pharmacologically acceptable salt thereof, wherein A is a cyclohexyl group substituted by one or two identical or different C1 to C6 alkyl groups.

4. The compound of claim 1 or a pharmacologically acceptable salt thereof, wherein A is a cyclohexyl group substituted by a methyl group or an ethyl group.

5. The compound of claim 1 or a pharmacologically acceptable salt thereof, wherein A is group selected from

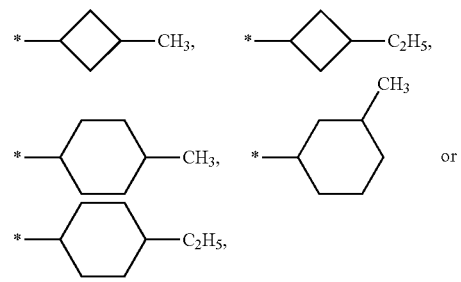

wherein * represents the position for substitution.

6. The compound of claim 1 or a pharmacologically acceptable salt thereof, wherein A is the group:

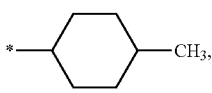 [SMILES: *C1CCC(C)CC1]

wherein * represents the position for substitution.

7. The compound of claim 1 or a pharmacologically acceptable salt thereof, wherein A is the group:

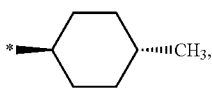

wherein * represents the position for substitution.

8. The compound of claim 1 or a pharmacologically acceptable salt thereof, wherein Y is the group —$CH_2$—$CHR^5$—$CH_2$—$NHR^6$, wherein $R^5$ represents a hydrogen atom, a C1 to C6 alkyl group, or a C1 to C6 alkoxy group, and $R^6$ represents a hydrogen atom or a prodrug group.

9. The compound of claim 8 or a pharmacologically acceptable salt thereof, wherein $R^5$ is a hydrogen atom.

10. The compound of claim 8 or a pharmacologically acceptable salt thereof, wherein $R^6$ is a hydrogen atom.

11. The compound of claim 1 or a pharmacologically acceptable salt thereof, wherein Y is the group:

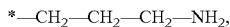

wherein * represents the position for substitution.

12. The compound of claim 1 or a pharmacologically acceptable salt thereof, wherein all of $R^1$, $R^2$, and $R^3$ are a hydrogen atom.

13. The compound of claim 1 or a pharmacologically acceptable salt thereof, wherein $R^4$ is a hydrogen atom.

14. The compound (2S)-5-amino-2-{[1-(trans-4-methyl-cyclohexyl)-1H-imidazol-4-yl]methyl}valeric acid or a pharmacologically acceptable salt thereof.

15. The pharmacologically acceptable salt of the compound of claim 1, wherein the pharmacologically acceptable salt is p-toluenesulfonate or benzenesulfonate.

16. The compound (2S)-5-amino-2-{[1-(trans-4-methyl-cyclohexyl)-1H-imidazol-4-yl]methyl}valeric acid.

17. The compound (2S)-5-amino-2-{[1-(trans-4-methyl-cyclohexyl)-1H-imidazol-4-yl]methyl}valeric acid p-toluenesulfonate.

18. The compound (2S)-5-amino-2-{[1-(trans-4-methyl-cyclohexyl)-1H-imidazol-4-yl]methyl}valeric acid p-toluenesulfonate anhydrate.

19. The compound (2S)-5-amino-2-{[1-(trans-4-methyl-cyclohexyl)-1H-imidazol-4-yl]methyl}valeric acid p-toluenesulfonate anhydrate or claim 18, which is in crystalline form exhibiting main peaks at interplanar spacings d of 23.9, 11.9, 4.5, 4.3, and 3.6 angstroms in powder X-ray diffraction obtained by copper Kα radiation.

20. The compound (2S)-5-amino-2-{[1-(trans-4-methyl-cyclohexyl)-1H-imidazol-4-yl]methyl}valeric acid p-toluenesulfonate monohydrate.

21. The compound (2S)-5-amino-2-{[1-(trans-4-methyl-cyclohexyl)-1H-imidazol-4-yl]methyl}valeric acid p-toluenesulfonate monohydrate of claim 20, which is in crystalline form exhibiting main peaks at interplanar spacings d of 22.9, 5.0, 4.9, 4.7, and 4.0 angstroms in powder X-ray diffraction obtained by copper Kα radiation.

* * * * *

UNITED STATES PATENT AND TRADEMARK OFFICE
CERTIFICATE OF CORRECTION

PATENT NO. : 8,609,710 B2
APPLICATION NO. : 13/550366
DATED : December 17, 2013
INVENTOR(S) : Tsutomu Nagata et al.

It is certified that error appears in the above-identified patent and that said Letters Patent is hereby corrected as shown below:

In item (75) the Inventors section on the Title page, delete "Ichikawa" as Inventor Tsutomu Nagata's city of residence and insert -- Tokyo --.

In item (75) the Inventors section on the Title page, delete "Shinagawa" as Inventor Masahiro Inoue's city of residence and insert -- Tokyo --.

In item (75) the Inventors section on the Title page, delete "Itabashi" as Inventor Yuka Ashida's city of residence and insert -- Tokyo --.

In item (75) the Inventors section on the Title page, delete "Shinagawa" as Inventor Kengo Noguchi's city of residence and insert -- Tokyo --.

In item (75) the Inventors section on the Title page, delete "Toshima" as Inventor Makoto Ono's city of residence and insert -- Tokyo --.

In the Claims

In claim 1, at column 126, at line 14, delete "or a pharmacologically acceptable salt thereof;" and insert -- or a pharmacologically acceptable salt thereof, --.

In claim 1, at column 126, at line 22, delete "-$CH_2$-$CHR^5$-$CH_2$-$NHR^6$, where $R^5$ is a hydrogen" and insert -- -$CH_2$-$CHR^5$-$CH_2$-$NHR^6$, wherein $R^5$ is a hydrogen --.

In claim 5, at column 126, at line 52, delete "acceptable salt thereof, wherein A is group selected from" and insert -- acceptable salt thereof, wherein A is a group selected from --.

In claim 19, at column 128, at line 21, delete "enesulfonate anhydrate or claim 18, which is in crystalline" and insert -- enesulfonate anhydrate of claim 18, which is in crystalline --.

Signed and Sealed this
Twenty-second Day of April, 2014

Michelle K. Lee
*Deputy Director of the United States Patent and Trademark Office*